United States Patent
Mahadevan et al.

(10) Patent No.: US 10,626,423 B2
(45) Date of Patent: Apr. 21, 2020

(54) METHODS AND MICROORGANISMS FOR THE PRODUCTION OF 1,3-BUTANEDIOL

(71) Applicant: THE GOVERNING COUNCIL OF THE UNIVERSITY OF TORONTO, Toronto (CA)

(72) Inventors: Radhakrishnan Mahadevan, Toronto (CA); Alexander Yakunin, Toronto (CA); Pratish Gawand, Toronto (CA); Kayla Nemr, Toronto (CA)

(73) Assignee: THE GOVERNING COUNCIL OF THE UNIVERSITY OF TORONTO, Toronto, Ontario (CA)

( * ) Notice: Subject to any disclaimer, the term of this patent is extended or adjusted under 35 U.S.C. 154(b) by 0 days.

(21) Appl. No.: 15/746,241

(22) PCT Filed: Jul. 21, 2016

(86) PCT No.: PCT/CA2016/050858
§ 371 (c)(1),
(2) Date: Jan. 19, 2018

(87) PCT Pub. No.: WO2017/011915
PCT Pub. Date: Jan. 26, 2017

(65) Prior Publication Data
US 2018/0340193 A1 Nov. 29, 2018

Related U.S. Application Data

(60) Provisional application No. 62/195,011, filed on Jul. 21, 2015.

(51) Int. Cl.
*C12P 7/18* (2006.01)
*C12P 7/24* (2006.01)
*C12N 9/04* (2006.01)
*C12N 15/52* (2006.01)
*C12N 9/88* (2006.01)

(52) U.S. Cl.
CPC .............. *C12P 7/18* (2013.01); *C12N 9/0006* (2013.01); *C12N 9/88* (2013.01); *C12N 15/52* (2013.01); *C12P 7/24* (2013.01); *C12Y 101/01001* (2013.01); *C12Y 401/02004* (2013.01)

(58) Field of Classification Search
CPC ........ C12N 9/88; C12N 15/52; C12N 9/0006; C12P 7/18; C12P 7/24; C12Y 101/01001; C12Y 401/02004
See application file for complete search history.

(56) References Cited

U.S. PATENT DOCUMENTS 9,017,983 B2 * 4/2015 Burgard ............... C12N 15/52
435/243

FOREIGN PATENT DOCUMENTS

| GB | 1417268.8 | * 11/2014 | ............... C12N 9/88 |
|---|---|---|---|
| WO | 2010/127319 A2 | 11/2010 | |
| WO | 2016/050842 A1 | 4/2016 | |
| WO | 2017/011915 A1 | 1/2017 | |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Torrelo et al., Biocataysis. Catal Lett., 2015, vol. 145: 309-345. (Year: 2015).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Chen, X., et al., "Metabolic engineering of *Escherichia coli*: A sustainable industrial platform for bio-based chemical production," Biotechnology Advances, vol. 31; Issue 8; 1200-1223 (2013).
International Search Report and Written Opinion of the International Searching Authority for International Application No. PCT/CA2016/050858, entitled: "Methods and Microorganisms for the Production of 1,3-Butanediol," dated Oct. 21, 2016.
Kataoka, N., et al., "Improvement of (R)-1,3-butanediol production by engineered *Escherichia coli*," Journal of Bioscience and Bioengineering, vol. 115; Issue 5; 475-480 (2013).
Supplementary European Search Report, EP Application No. 16826969.4; Date of Completion: Jan. 9, 2019.

(Continued)

*Primary Examiner* — Ganapathirama Raghu
(74) *Attorney, Agent, or Firm* — Hamilton, Brook, Smith & Reynolds, P.C.

(57) ABSTRACT

A non-naturally occurring microorganism having a 1,3-BDO pathway is provided. The microorganism expresses at least one of the following 1,3-BDO pathway enzymes: an aldolase that catalyzes condensation of two acetaldehydes to produce 3-hydroxybutanal; and an aldo-ketoreductase, oxidoreductase, aldehyde reductase or alcohol dehydrogenase that reduces 3-hydroxybutanal to 1,3-BDO. The organism may further express one or more enzymes for producing acetaldehyde. A biosynthetic process involves condensing two acetaldehyde molecules to 3-hydroxybutanal using an enzyme from class aldolases; and selectively reducing 3-hydroxybutanal to 1,3-BDO using an enzyme belonging to the class aldo-ketoreductase, oxidoreductase, aldehyde reductase or alcohol dehydrogenase. The process can further include producing acetaldehyde by a biosynthetic method.

23 Claims, 8 Drawing Sheets
Specification includes a Sequence Listing.

(56) References Cited

OTHER PUBLICATIONS

Fei, et al., "Improving the acetaldehyde tolerance of DERAsep by enhancing the rigidity of its protein structure", Journal of Molecular Catalysis B: Enzymatic, vol. 116, Mar. 30, 2015, pp. 148-152.
Fesko, et al., "Biocatalytic methods for C—C bond formation", Chemcatchem, vol. 5, 2013, pp. 1248-1272.
Sakuraba et al., "Sequential aldol condensation catalyzed by hyperthermophilic 2-deoxy-D-ribose-5-phosphate aldolase", Applied and Enviornmental Microbiology, vol. 73, 2007, pp. 7427-7434.
Jennewein et al., "Directed evolution of an industrial biocatalyst: 2-deoxy-D-ribose 5-phosphate aldolase", Biotechnology Journal, vol. 1, 2006, pp. 537-548.

* cited by examiner

Figure 4

```
                           1         10        20        30        40        50        60
                           |         |         |         |         |         |         |
SEQ ID NO: 43   APE2437    ------------------------------------------------------MREASDY-
SEQ ID NO: 44   BCE1975    ----------------------------MNIAKLIDHTILKANTTKEDVMKVIEEAKEY-
SEQ ID NO: 45   LMO1995    ----------------------------MTIAKMIDHTALKPDTTKEQILTLTKEAREY-
SEQ ID NO: 46   BSU3938    ----------------------------MSLANIIDHTALKPHTQKADILKLIEEAKTY-
SEQ ID NO: 47   BH1352     MS--------------------------RSIAQMIDHTLLKPNTTEDQIVKLCEEAKEY-
SEQ ID NO: 48   SP0843     ----------------------------MKLNKYIDHTLLKQDAKKKQIDSLLSEAREY-
SEQ ID NO: 49   SA0138     ----------------------------MKFEKYIDHTLLKPESTRTQIDQIIDEAKAY-
SEQ ID NO: 50   SA2137     ----------------------------MNSAKLIDHTLLKPESTRTQIDQIIDEAKAY-
SEQ ID NO: 51   DRD1181    ----------------------------MSLASYIDHTLLKATATLADIRTLCEEAREH-
SEQ ID NO: 52   LB1413     MTLTT---------------------EQLARYIDHTNLKADATEADIKQTCDEARKF-
SEQ ID NO: 53   TM1559     MIEYRIEEAVARYREFYEFKPVRESAGIEDVKSAIEHTNLKPFATPDDIKKLCLEAREN-
SEQ ID NO: 54   MTH0818    MVKMNVETR-----------------EELASLIDHTNVRADATENDIERLCREAVSY-
SEQ ID NO: 55   HL1382     ------MDR-----------------ETLAARIDHTVLGPTTTRADVLSVVDDAEAH-
SEQ ID NO: 56   TA0684     MKYSI---------------------EQVMRLVDHSGLKPYLTEKDIARLIEEAKDM-
SEQ ID NO: 57   EC1535     MTDLKASS------------------LRALRLMDLTTLNDDDTDEKVIALCHQAKTPV

SEQ ID NO: 43   APE2437    -GFRCAVLTPVYTVKISGLA--EKL-GVKLCSVIGFPLGQAPLEVKLVEAQTVLEAGATE
SEQ ID NO: 44   BCE1975    -KFASVCINPTWVKLAAEEL--AGH-DVDVCTVIGFPLGASTTETKAFETKDAIAKGATE
SEQ ID NO: 45   LMO1995    -GFASVCVNPTWVKLSAEQL--AGA-ESVVCTVIGFPLGANTPEVKAFEVKRDAIQNGAKE
SEQ ID NO: 46   BSU3938    -KFASVCVNPTWVELAAKEL--KGT-GVDVCTVIGFPLGANTTETKAFETKDAISKGATE
SEQ ID NO: 47   BH1352     -SFASVCVNPTWVALAAQLL--KDAPDVKVCTVIGFPLGATTPEVKAFETTNAIENGATE
SEQ ID NO: 48   SP0843     -DFASVCVNPTWVEHAKRGL--EGT-DVKVCTVVGFPLGATTSAVKAFETKEAIQNGADE
SEQ ID NO: 49   SA0138     -NFKSVCVNPTHVKYAAERL--ADS-EVLVCTVIGFPLGASTTATKAFETEDAIQNGADE
SEQ ID NO: 50   SA2137     -HFKSVCVNPTHVKYAAERL--ADS-EVLVCTVIGFPLGASTTATKAFETEDAIQNGADE
SEQ ID NO: 51   DRD1181    -SFYAVCINPVFIPHARAWL--EGS-DVKVATVCGFPLGAISSEQKALEARLSAETGADE
SEQ ID NO: 52   LB1413     -NTASVCVNSYWIPFVTEQL--KGT-DVNPIAVVGFPLGAMATESEIFEATTAIDQGAEE
SEQ ID NO: 53   TM1559     -RFHGVCVNPCYVKLAREEL--EGT-DVKVVTVVGFPLGANETRTKAHEAIFAVESGADE
SEQ ID NO: 54   MTH0818    -GFRCAVVTPTNVRLAAELL--EGT-DVTVCSVVGFPAGVSTPRVKALEASEAVENGAGE
SEQ ID NO: 55   HL1382     -GM-NVCIPPCYVADARDHA--SA--DRTIATVIGFPHGTQATSVKVAAAEHAHADGADE
SEQ ID NO: 56   TA0684     -GNYAVCIEPIYGKFAKEYLDEKRY-KVKLDVTIDFPFGSLATSSRRKIIEDS--DYADE
SEQ ID NO: 57   EC1535     GNTAAICIYPRFIPIARKTLKEQGTPEIRIATVTNFPHGNDDIDIALAETRAAIAYGADE

SEQ ID NO: 43   APE2437    IDVVPHLSL----GPEAVYREVSGIVKLAKSYGAVVKVILEAPLWDDKTLSL-LVDSSRR
SEQ ID NO: 44   BCE1975    VDMVINVGALKDGDDELVEKDIYEVVQAARGK-ALVKVIIETCLLTDEEKVR-ACELSVK
SEQ ID NO: 45   LMO1995    VDMVINIGALKDKDDELVERDIRAVVDAKGK-ALVKVIIETCLLTDEEKVR-ACEIAVK
SEQ ID NO: 46   BSU3938    VDMVINIAALKDKEDDVVEADIRGVVEAVGK-ALVKVIIETCLLTDEEKER-ACRLAVS
SEQ ID NO: 47   BH1352     VDMVINIGALKDKQYELVGRDIQAVVKAAEGK-ALTKVIIETSLLTEEEKRA-ACELAVK
SEQ ID NO: 48   SP0843     IDMVINVGALKSGNLALVESDIRAVVEASGDK--LVKVIIEACLLTDQERVV-VCQLAQK
SEQ ID NO: 49   SA0138     IDMVINIGALKDGRFDDVQQDIEAVVKAAKGH--TVKVIIETVLLDHDEIVK-ASELTKA
SEQ ID NO: 50   SA2137     IDMVINIGALKDGRFDDVQQDIEAVVKAAKGH--TVKVIIETVLLDHDEIVK-ASELTKV
SEQ ID NO: 51   DRD1181    IDMVIHIGSALAGDWDAVEADVRAVRRAVPEQ--VLKVIIETCYLTDEQKRL-ATEVAVQ
SEQ ID NO: 52   LB1413     IDMVLNVGELKGGNDEKVLADIQGLADAVHAKGKILKVILENALLTKDEIVR-ACQLSEK
SEQ ID NO: 53   TM1559     IDMVINVGMLKAREWEYVYEDIRSVVESVRGK--VVKVIIETCYLDTEEKIA-ACVISKL
SEQ ID NO: 54   MTH0818    VDMVMNIGAMKSGNRELVYRDISGVVDAAGVP---VKVILETAYLTDREKVE-ACLISKE
SEQ ID NO: 55   HL1382     IDLVIPIGLRKGGDHEAVTAEIAAVNDATPLP---VKVIIETPVLTDAERHA-ACEAAAD
SEQ ID NO: 56   TA0684     VDIVVPMGYVKSHRWDYVDQDLTDVVKIAKDHDLVIKIITEDGYLTQDEKDR-LYRSVIR
SEQ ID NO: 57   EC1535     VDVVFPYRALMAGNEQVGFDLVKACKEACAAANVLLKVIIETGELKDEALIRKASEISIK

SEQ ID NO: 43   APE2437    AGADIVKTSTGVYT----------KGGDPVTVFRLASLAKPLG----MGVKASGGIRSGI
SEQ ID NO: 44   BCE1975    AGADFVKTSTGFST----------GGATAEDIALMRKT---VGPN--VGVKASGGVRTRE
SEQ ID NO: 45   LMO1995    AGTDFVKTSTGFST----------GGATAEDIALMRKT---VGPN--IGVKASGGVRTKE
SEQ ID NO: 46   BSU3938    AGADFVKTSTGFST----------GGATKEDIALMRKT---VGPD--IGVKASGGVRTKE
SEQ ID NO: 47   BH1352     AGADFVKTSTGFSG----------GGATAEDIALMRKV---VGPN--LGVKASGGVRDLS
SEQ ID NO: 48   SP0843     AGADFVKTSTGFST----------GGATIADVTLMRET---VGSD--MGVKAAGGARSYA
SEQ ID NO: 49   SA0138     AGADFVKTSTGFAG----------GGATAEDVKLMKDT---VGAD--VEVKASGGVRNLE
SEQ ID NO: 50   SA2137     AGADFVKTSTGFAG----------GGATAEDVKLMKDT---VGAD--VEVKASGGVRNLE
SEQ ID NO: 51   DRD1181    GGADFVKTSTGFGT----------GGATVDDVRLMAEV---IGGR--AGIKAAGGVRTPA
SEQ ID NO: 52   LB1413     AGADFVKTSTGFST----------SGAKVEDVKLMRET---VGDR--LGVKASGGIHSRE
SEQ ID NO: 53   TM1559     AGAHFVKTSTGFGT----------GGATAEDVHLMKWI---VGDE--MGVKASGGIRTFE
SEQ ID NO: 54   MTH0818    AGAAFVKTSTAYGG----------LAGATVEDVMLMRKT---VGDE--MGVKASGGIRTLE
SEQ ID NO: 55   HL1382     ADAAMVKTATGFTD----------GGATVPDVSLMSEY---------LPVKASGGVGTYA
SEQ ID NO: 56   TA0684     AKPDFIKTSTGFANKDYCASLGNAAGATPDNVSLMSRIAEELGSD--IGIKAAGGIHTYR
SEQ ID NO: 57   EC1535     AGADFIKTSTGKVA----------VNATPESARIMMEVIRDMGVERTVGRKPAGGVRTAE

SEQ ID NO: 43   APE2437    DAVLAVGA-----GAD-------IIGTS----SAVRVLESFKSLV----
SEQ ID NO: 44   BCE1975    DAEKMVAA-----GAS-------RVGAS----ASVAIVLNDAKGATDNY
SEQ ID NO: 45   LMO1995    DVERMIEA-----GAT-------RIGAS----AGVAIVSGEKPARPDNY
SEQ ID NO: 46   BSU3938    DVDTMVEA-----GAS-------RIGAS----AGVSIVKGENASGGDNY
SEQ ID NO: 47   BH1352     DAKAMIDA-----GAT-------RIGAS----AGVAIVNGERSEG--SY
SEQ ID NO: 48   SP0843     DALAFVEA-----GAT-------RIGTS----AGVAILKGELADG--DY
SEQ ID NO: 49   SA0138     DFNKMVEA-----GAT-------RIGAS----AGVQIMQGLEADS--DY
SEQ ID NO: 50   SA2137     DFNKMVEA-----GAT-------RIGAS----AGVQIMQGLEADS--DY
SEQ ID NO: 51   DRD1181    DAQAMIEA-----GAT-------RLGTS----GGVGLVSGGENGA--GY
SEQ ID NO: 52   LB1413     EALAMIDA-----GAS-------RMGVS----ATVAILTGDDSHAKAGY
SEQ ID NO: 53   TM1559     DAVRMIMY-----GAD-------RIGTS----SGVKIVQGGEERY--GG
SEQ ID NO: 54   MTH0818    TALAMIDA-----GAT-------RIGTS----TGVQIIEGWR------
SEQ ID NO: 55   HL1382     DAAAMFDA-----GAV-------RIGAS----SGVDIVASFAE------
SEQ ID NO: 56   TA0684     EIESIIDA-----AKRPIDPERLRIGMS----GTGKVFEEMRKIKK---
SEQ ID NO: 57   EC1535     DAQKYLAIADELFGAIWADARHYRFGASSLLASLLKALGHGDGKSASSY
```

Figure 5

```
                          1         10        20        30        40        50        60
                          |         |         |         |         |         |         |
SEQ ID NO: 43 APE2437     ------------------------------------------------------MREASDY-
SEQ ID NO: 44 BCE1975     -------------------------MNIAKLIDHTILKANTTKEDVMKVIEEAKEY-
SEQ ID NO: 45 LMO1995     -------------------------MTIAKMIDHTALKPDTTKEQILTLTKEAREY-
SEQ ID NO: 46 BSU3938     -------------------------MSLANIIDHTALKPHTQKADILKLIEEAKTY-
SEQ ID NO: 47 BH1352      MS-----------------------RSIAQMIDHTLLKPNTTEDQIVKLCEEAKEY-
SEQ ID NO: 48 SP0843      -------------------------MKLNKYIDHTLLKQDAKKKQIDSLLSEAREY-
SEQ ID NO: 49 SA0138      -------------------------MKFEKYIDHTLLKPESTRTQIDQIIDEAKAY-
SEQ ID NO: 50 SA2137      -------------------------MNSAKLIDHTLLKPESTRTQIDQIIDEAKAY-
SEQ ID NO: 51 DRD1181     -------------------------MSLASYIDHTLLKATATLADIRTLCEEAREH-
SEQ ID NO: 52 LB1413      MTLTT--------------------EQLAKYIDHTNLKADATEADIKQTCDEAKKF-
SEQ ID NO: 53 TM1559      MIEYRIEEAVAKYREFYEFKPVRESAGIEDVKSAIEHTNLKPFATPDDIKKLCLEAREN-
SEQ ID NO: 54 MTH0818     MVKMNVETR----------------EELASLIDHTNVRADATENDIERLCREAVSY-
SEQ ID NO: 55 HL1382      ------MDR----------------ETLAARIDHTVLGPTTTRADVLSVVDDAEAH-
SEQ ID NO: 56 TA0684      MKYSI--------------------EQVMRLVDHSGLKPYLTEKDIARLIEEAKDM-
SEQ ID NO: 57 EC1535      MTDLKASS-----------------LRALKLMDLTTENDDDTDEKVIALCHQAKTPV

SEQ ID NO: 43 APE2437     -GFRCAVETPVYTVKISGLA--EKL-GVKLCSVIGFPLGQAPLEVKLVEAQTVLEAGATE
SEQ ID NO: 44 BCE1975     -KFASVCINPTWVKLAAEEL--AGH-DVDVCTVIGFPLGASTTETKAFETKDAIAKGATE
SEQ ID NO: 45 LMO1995     -GFASVCVNPTWVKLSAEQL--AGA-ESVVCTVIGFPLGANTPEVKAFEVKDAIQNGAKE
SEQ ID NO: 46 BSU3938     -KFASVCVNPTWVELAAKEL--KGT-GVDVCTVIGFPLGANTTETKAFETKDAISKGATE
SEQ ID NO: 47 BH1352      -SFASVCVNPTWVALAAQLL--KDAPDVKVCTVIGFPLGATTPEVKAFETTNAIENGATE
SEQ ID NO: 48 SP0843      -DFASVCVNPTWVEHAKKGL--EGT-DVKVCTVVGFPLGATTSAVKAFETKEAIQNGADE
SEQ ID NO: 49 SA0138      -NFKSVCVNPTHVKYAAERL--ADS-EVLVCTVIGFPLGASTTATKAFETEDAIQNGADE
SEQ ID NO: 50 SA2137      -HFKSVCVNPTHVKYAAERL--ADS-EVLVCTVIGFPLGASTTATKAFETEDAIQNGADE
SEQ ID NO: 51 DRD1181     -SFYAVCINPVFIPHARAWL--EGS-DVKATVCGFPLGAISSEQKALEARLSAETGADE
SEQ ID NO: 52 LB1413      -NTASVCVNSYWIPFVTEQL--KGT-DVNPIAVVGFPLGAMATESEIFEATTAIDQGAEE
SEQ ID NO: 53 TM1559      -RFHGVCVNPCYVKLAREEL--EGT-DVKVVTVVGFPLGANETRTKAHEAIFAVESGADE
SEQ ID NO: 54 MTH0818     -GFRCAVVTPTNVRLAAELL--EGT-DVTVCSVVGFPAGVSTPRVKALEASEAVENGAGE
SEQ ID NO: 55 HL1382      -GM-NVCIPPCYVADARDHA--SA--DRTIATVIGFPHGTQATSVKVAAAEHAHADGADE
SEQ ID NO: 56 TA0684      -GNYAVCIEPIYGKFAKEYLDEKRY-KVKLDVTIDFPFGSLATSSRKKIIEDS--DYADE
SEQ ID NO: 57 EC1535      GNTAAICIYPRFIPIARKTLKEQGTPEIRIATVTNFPHGNDDIDIALAETRAAIAYGADE

SEQ ID NO: 43 APE2437     LDVVPHLSL----GPEAVYREVSGIVKLAKSYGAVVKVILEAPLWDDKTLSL-LVDSSRR
SEQ ID NO: 44 BCE1975     VDMVINVGALKDGDDELVEKDIYEVVQAAKGK-ALVKVIIETCLLTDEEKVR-ACELSVK
SEQ ID NO: 45 LMO1995     VDMVINIGALKDKDDELVERDIRAVVDVAKGK-ALVKVIIETCLLTDEEKVR-ACEIAVK
SEQ ID NO: 46 BSU3938     VDMVINIAALKDKEDDVVEADIRGVVEAVAGK-ALVKVIIETCLLTDEEKER-ACRLAVS
SEQ ID NO: 47 BH1352      VDMVINIGALKDKQYELVGRDIQAVVKAAEK-ALTKVIIETSLLTEEEKKA-ACELAVK
SEQ ID NO: 48 SP0843      IDMVINVGALKSGNLALVESDIRAVVEASGDK--LVKVIIEACLLTDQEKVV-VCQLAQK
SEQ ID NO: 49 SA0138      IDMVINIGALKDGRFDDVQQDIEAVVKAAKGH--TVKVIIETVLLDHDEIVK-ASELTKA
SEQ ID NO: 50 SA2137      IDMVINIGALKDGRFDDVQQDIEAVVKAAKGH--TVKVIIETVLLDHDEIVK-ASELTKV
SEQ ID NO: 51 DRD1181     IDMVIHIGSALAGDWDAVEADVRAVRRAVPEQ--VLKVIIETCYLTDEQKRL-ATEVAVQ
SEQ ID NO: 52 LB1413      IDMVLNVGELKGGNDEKVLADIQGLADAVHAKGKILKVILENALLTKDEIVR-ACQLSEK
SEQ ID NO: 53 TM1559      IDMVINVGMLKAKEWEYVYEDIRSVVESVKGK--VVKVIIETCYLDTEEKIA-ACVISKL
SEQ ID NO: 54 MTH0818     VDMVMNIGAMKSGNRELVYRDISGVVDAAGVP---VKVILETAYLTDKEKVE-ACLISKE
SEQ ID NO: 55 HL1382      LDLVIPIGRLKGGDHEAVTAEIAAVNDATPLP---VKVIIETPVLTDAEKHA-ACEAAAD
SEQ ID NO: 56 TA0684      VDIVVPMGYVKSHRWDVDQDLTDVVKIAKDHDLVIKIITEDGYLTQDEKDR-LYRSVIR
SEQ ID NO: 57 EC1535      VDVVFPYRALMAGNEQVGFDLVKACKEACAAANVLLKVIIETGELKDEALIRKASEISIK

SEQ ID NO: 43 APE2437     AGADIVKTSTGVYT----------KGGDPVTVFRIASLAKPLG----MGVKASGGIRSGI
SEQ ID NO: 44 BCE1975     AGADFVKTSTGFST----------GGATAEDIALMRKT---VGPN--VGVKASGGVRTRE
SEQ ID NO: 45 LMO1995     AGTDFVKTSTGFST----------GGATAEDIALMRKT---VGPN--IGVKASGGVRTKE
SEQ ID NO: 46 BSU3938     AGADFVKTSTGFST----------GGATKEDIALMRKT---VGPD--IGVKASGGVRTKE
SEQ ID NO: 47 BH1352      AGADFVKTSTGFSG----------GGATAEDIALMRKV---VGPN--LGVKASGGVRDLS
SEQ ID NO: 48 SP0843      AGADFVKTSTGFST----------GGATIADVTLMRET---VGSD--MGVKAAGGARSYA
SEQ ID NO: 49 SA0138      AGADFVKTSTGFAG----------GGATAEDVKLMKDT---VGAD--VEVKASGGVRNLE
SEQ ID NO: 50 SA2137      AGADFVKTSTGFAG----------GGATAEDVKLMKDT---VGAD--VEVKASGGVRNLE
SEQ ID NO: 51 DRD1181     GGADFVKTSTGFGT----------GGATVDDVRLMAEV---IGGR--AGLKAAGGVRTPA
SEQ ID NO: 52 LB1413      AGADFVKTSTGFST----------SGAKVEDVKLMRET---VGDR--LGVKASGGIHSRE
SEQ ID NO: 53 TM1559      AGAHFVKTSTGFGT----------GGATAEDVHLMKWI---VGDE--MGVKASGGIRTFE
SEQ ID NO: 54 MTH0818     AGAAFVKTSTAYGG----------LAGATVEDVHLMKWI---VGDE--MGVKASGGIRDLE
SEQ ID NO: 55 HL1382      ADAAMVKTATGFTD----------GGATVPDVSLMSEY---------LPVKASGGVGTYA
SEQ ID NO: 56 TA0684      AKPDFIKTSTGFANKDYCASLGNAAGATPDNVSLMSRIAEELGSD--IGIKAAGGIHTYR
SEQ ID NO: 57 EC1535      AGADFIKTSTGKVA----------VNATPESARIMMEVIRDMGVEKTVGFKPAGGVRTAE

SEQ ID NO: 43 APE2437     DAVLAVGA-----GAD-------IIGTS----SAVKVLESFKSLV----
SEQ ID NO: 44 BCE1975     DAEKMVAA-----GAS-------RVGAS----ASVAIVLNDAKGATDNY
SEQ ID NO: 45 LMO1995     DVEKMIEA-----GAT-------RIGAS----AGVAIVSGEKPAKPDNY
SEQ ID NO: 46 BSU3938     DVDTMVEA-----GAS-------RIGAS----AGVSIVKGENASGGDNY
SEQ ID NO: 47 BH1352      DAKAMIDA-----GAT-------RIGAS----AGVAIVNGERSEG--SY
SEQ ID NO: 48 SP0843      DALAFVEA-----GAT-------RIGTS----AGVAILKGELADG--DY
SEQ ID NO: 49 SA0138      DFNKMVEA-----GAT-------RIGAS----AGVQIMQGLEADS--DY
SEQ ID NO: 50 SA2137      DFNKMVEA-----GAT-------RIGAS----AGVQIMQGLEADS--DY
SEQ ID NO: 51 DRD1181     DAQAMIEA-----GAT-------RLGTS----GGVGLVSGGENGA--GY
SEQ ID NO: 52 LB1413      EALAMIDA-----GAS-------RMGVS----ATVAILTGDDSHAKAGY
SEQ ID NO: 53 TM1559      DAVKMIMY-----GAD-------RIGTS----SGVKIVQGGEERY--GG
SEQ ID NO: 54 MTH0818     TALAMIDA-----GAD-------RIGTS----TGVQIIEGWR------
SEQ ID NO: 55 HL1382      DAAAMFDA-----GAV-------RIGAS----SGVDIVASFAE------
SEQ ID NO: 56 TA0684      EIESIIDA-----AKRPIDPEKLRIGMS----GTGKVFEEMKKIKK---
SEQ ID NO: 57 EC1535      DAQKYLAIADELFGADWADARHYRFGASSLLASLLKALGHGDGKSASSY
```

Figure 6

```
Score = 1027.0, Identities = 202/333 (60%), Positives = 249/333 (74%), Gaps = 6/333 (1%)

SEQ ID NO: 58 BSU0953    1  MEYTSIADTGIEA--SRIGLGTWAIGGMWGTDEKTSIETIRAALDQGITLIDTAPAYG   58
                             M  SI   GI+    SRIGLGTWAIGG MWG D+ TS+EIIR A++ GI LIDTAP YG
SEQ ID NO: 59 PA1127     1  MSVESIRIEGIDTPVSRIGLGTWAIGGMWGGADERTSVETIRRAVESGINLIDTAPVYG  60

SEQ ID NO: 58 BSU0953   59  FGQSEEIVGKAIKEYGHRDQVILATKTALDWHGWQLFRHANRARIVEEVENSLKRLQTDY 118
                            FG SEE+VGKA++  G RD+ ++AIK AL+W +  + R+A+ ARI  EVE+SL+RL+TD
SEQ ID NO: 59 PA1127    61  FGHSEEVVGKALQ--GLRDKAVIATKAALEWSDAGIHRNASAARIRREVEDSLRRLKTDR 118

SEQ ID NO: 58 BSU0953  119  IDLYQVHNFDPLVPIEETAEVMKELYDAGKIRAIGVSNFSIEQMDTFRAVAPLHTIQPPY 178
                            IDLYQ+HNFDPLV  EETA  ++  L   GKI AIGVSN+S EQMD FR  APL ++QPPY
SEQ ID NO: 59 PA1127   119  IDLYQIHNFDPLVAHEETAGELERLRRDGKILAIGVSNYSPEQMDGFRQFAPLASVQPPY 178

SEQ ID NO: 58 BSU0953  179  NLFEREMEESVLPYAKDNKITTLIYPSLQRDLLTGRMTEEYTFEGCDLRWHDPKFQKPRF 238
                            NLFER ++  VLPYA+ N I  L  YG+LQRGLL+ Q+M  E   F+G DLR  DPK FQ+PRF
SEQ ID NO: 59 PA1127   179  NLFERAIDADVLPYAERNGIVVLAYGALQRGLLSQRMNAETRFDGCDLRKSDPKFQQPRF 238

SEQ ID NO: 58 BSU0953  239  KEYLSAVNQLDKLAKTRYGKSVIRLAVRWILDQPGADIALAGRRFPQQLEALSEITGWTL 298
                             +YL++V QL++LA+ RYGKSV+ LA+RWILD+ G  +AL  + P QL +++ GW L
SEQ ID NO: 59 PA1127   239  AQYLAAVAQLEELAEERYGKSVLALAIRWILDR-GPTVALAGRRTPEQLNGIADAFGWRL 297

SEQ ID NO: 58 BSU0953  299  NSEDQKDINTILENTISDPVGPEFMAPPIREEI 331
                             +  E   I  IL  TI DPVGPEFMAPP+R
SEQ ID NO: 59 PA1127   298  DDEAMARIERILAETIQDPVGPEFMAPPSRNA- 329
```

Figure 7

```
KDC (SEQ ID NO: 28)  -MTTVGDYLLDRLHELGIEEIFGVPGDYNLQFLDQIISPEDKWIGNANELNASYMADGY  59
PDC (SEQ ID NO: 26)  MSYTVGTYLAERLVQIGLKHHFAVAGDYNLVLLDNLLLNKNMEQVYCCNELNCGFSAEGY  60
BFD (SEQ ID NO: 27)  -MASVHGTTYELLRRQGIDTVFGNPGSNELPFLKDFP---EDFRYILALQEACVVGIADGY  57
                      *   *    *    *    *    *    *   *         *   *

KDC (SEQ ID NO: 28)  ARTKKAAAFLTTFGVG-ELSAINGLAGSYAENLPVVEIVGSPTSKVQNDGKFVHHTLADG  118
PDC (SEQ ID NO: 26)  ARAKGAAAAVVTSYG-ALSAFDAIGGAYAENLPVILISGAPNNNDHRAGHVLHHALGKT  119
BFD (SEQ ID NO: 27)  AQGSRKPAFINLHSAAGTGNAMGALGHAKTHGRPLIVTAGQQTRAMIGVEALLTNVDAAN  117
                       *      *          *            *   *

KDC (SEQ ID NO: 28)  DFRHFMKMHEPVT-AAPTLLTAEKATTEIDRVLSQLIKERK-PVYINLPVDVAAAPAEKP  176
PDC (SEQ ID NO: 26)  DYNYQLEMAKNITAAAEAIYTPEEAPAKIDHVIKTALRERKP-PVYLEIACNIASMPCAAP  178
BFD (SEQ ID NO: 27)  --------LPRPLVKNSYPDASAASVPHAMSDAISHAMSAPQGPVYLSVPYDVWDKDADFQ  170
                              *      *      *     *   *  *

KDC (SEQ ID NO: 28)  ---ALSLEHESSTTNTTEQVILSKIEESLKNAQKPVVIAGHEVISPGLEKTVTQFVSETKL  234
PDC (SEQ ID NO: 26)  GPASALFNDEASDEASLNAAVEETLKFIANRDKVAVLVGSRLRAAGAEEAAVKFADALGG  238
BFD (SEQ ID NO: 27)  -SMRLFDRHVSSSVRLNDQDLDILVKRLNGASNPAIVLGPDVDAANANADCVRLAERLKA  229
                         *          *       *      *      *    *

KDC (SEQ ID NO: 28)  PITTLNFG-KSAVDESLPSFLGIYNGKLGEISLKNFVESADFIIMLGVELTDSSTGAFTH  293
PDC (SEQ ID NO: 26)  AVATKAAA-KSFFPEENPRYIGTSWGEVSYPGVEKTMKEADAVIALAPVFNDYSTTGWTD  297
BFD (SEQ ID NO: 27)  PVWVAPSAPRCPFPTRHPCFRGLMP---AGIAAISQLLEGHDVVLVIGAPVFRYHQYDPGQ  287
                       *           *   *         *    *

KDC (SEQ ID NO: 28)  HLDENKMISLN------IDEGIIFNKVVEDFDFRAVVSSLSELKG-IEYEGQYIDRQYEEFI  348
PDC (SEQ ID NO: 26)  IPDPKELVLAEPRSVVVNGIRFPSVHLRDYLTRLAQKVSKKTGALDFFKSLNAGELRKAA  357
BFD (SEQ ID NO: 27)  YLRPGTRLISVTCDPLEAARAPMGDAIVADIGAMASALARLVE---ESSRQLPTAAPEPAK  345
                                  *            *     *    *

KDC (SEQ ID NO: 28)  PS--SAPLSQDRLRQAVESLTQSNETIVAEQGTSFFGASTIFLKSNSRFIGQPLMGSIGY  406
PDC (SEQ ID NO: 26)  PADPSAPLVNAEIARQVEALLTPPTTVIAETGDSWFNAQRMKLPNGARVEYEMQWGHIGW  417
BFD (SEQ ID NO: 27)  VDQDAGRLHPETVFDTLNDMAPENAIYLSESTSFTAQGWQRINMRNPGSYYPCAAGGELGF  405
                       *        *     *           *   *    *   *

KDC (SEQ ID NO: 28)  TFPRALGSQIADKESRHLLFIGDGSLQLTVQELGLSIPEKLNPICFIINNDGY----TVE  462
PDC (SEQ ID NO: 26)  SVPAAFGYAVGAPERRNILMVGDGSFQLTAQEVAQMVRLKLPVIIFLINNYGY----TIE  473
BFD (SEQ ID NO: 27)  ALPAAIGVQLAEPERQVIAVIGDGSANYSISALWTAACYNIPTIFVIMNNGTYGALRWFA  465
                      **  *    *     *     *****    *      * **   *

KDC (SEQ ID NO: 28)  REIRGPTQSYRDIPMNRYSRLFETFG-----ATEDRVVSRIYRTENEPVSVMKEAQADVNR  518
PDC (SEQ ID NO: 26)  VMTHDG--PYNNIKNWDYAGLMEVFNGNGGYDSGAGKGLKAKTGGELAEAIKVALANTDG  531
BFD (SEQ ID NO: 27)  GVLEAENVPGLDVPGIDFRALAKGYG--------VQAIKADNLEQLKGSLQEALSAKG-  515
                         *    *  *  *        *          *   *    *  *

KDC (SEQ ID NO: 28)  MYWIELVLEKEDAPFLLFKDMGELFAEQNK------- 547
PDC (SEQ ID NO: 26)  PTLIECFIGREDCTEELVKWGKRVAAANSRKPVNKLL 568
BFD (SEQ ID NO: 27)  -----PVLIEVSFVSPVK------------------- 528
                         *    *
```

METHODS AND MICROORGANISMS FOR THE PRODUCTION OF 1,3-BUTANEDIOL

RELATED APPLICATION(S)

This application is the U.S. National Stage of International Application No. PCT/CA2016/050858, filed Jul. 21, 2016, which designates the U.S., published in English, and claims the benefit of U.S. Provisional Application No. 62/195,011, filed Jul. 21, 2015. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 55331001001SubstituteSequenceListing.txt; created Sep. 26, 2019, 96 KB in size.

The present application includes as part of its description a sequence listing that includes 59 sequences and this sequence listing is incorporated into the present application in its entirety.

TECHNICAL FIELD

This disclosure relates to biosynthetic processes for producing organic compounds, including 1,3-butanediol (1,3-BDO).

BACKGROUND OF THE ART 1,3-butanediol may be used as a precursor to 1,3-butadiene, a common commodity chemical with an annual global market of around 22 billion USD. 1,3-butadiene is an important building block used to produce rubber, latex, resins, and plastics. Currently, 1,3-butadiene is produced using petroleum-based processes. Recently, large interest has been focused on producing 1,3-butanediol using a biotechnological route, mainly due to the opportunity to produce 1,3-butadiene catalytically from 1,3-butanediol. In addition to being a precursor to 1,3-butadiene, 1,3-butanediol finds applications in cosmetic and pharmaceutical products. The enantiopure form of 1,3-butanediol, such as (R)-1,3-butanediol, can be used to synthesize high-value compounds such as pheromones, fragrances, and insecticides. Techniques for 1,3-butanediol production continue to be sought.

SUMMARY

In one aspect, there is provided a non-naturally occurring microorganism having a 1,3-BDO pathway. The microorganism includes at least one of the following 1,3-BDO pathway enzymes: an aldolase that catalyzes condensation of two acetaldehydes to produce 3-hydroxybutanal; and an aldo-ketoreductase, oxidoreductase, aldehyde reductase or alcohol dehydrogenase that reduces 3-hydroxybutanal to 1,3-BDO. The microorganism has at least one exogenous nucleic acid encoding an enzyme from said 1,3-BDO pathway.

In one embodiment, the non-naturally occurring microorganism includes at least one modification to an endogenous nucleic acid encoding an enzyme from the 1,3-BDO pathway or affecting the expression of an enzyme from this 1,3-BDO pathway.

In one embodiment, the microorganism has an exogenous nucleic acid that encodes the aldolase. In one embodiment, the exogenous nucleic acid comprises a nucleotide sequence of SEQ ID NO: 1, 2, 3, 4, 5, 6, 7, 8, 9, or 10. In one embodiment, the aldolase is deoxyribose-5-phosphate aldolase (DERA). In one embodiment, the aldolase comprises an amino acid sequence of SEQ ID NO: 15, 16, 17, 18, 19, 20, 21, 22, 23, or 24 or active fragment or homologue thereof. In one embodiment, the aldolase enzyme includes the following conserved amino acid residues in the active site of the enzyme: lysine167, lysine 201, aspartic acid 16 and aspartic acid 102, where the number associated with each residue refers to the residue number in the amino acid sequence of *E. coli* DERA of the SEQ ID NO. 20.

In one embodiment, the microorganism includes an exogenous nucleic acid that encodes the aldo-ketoreductase, oxidoreductase, aldehyde reductase or alcohol dehydrogenase. In one embodiment, the microorganism expresses an aldo-keto reductase comprising an amino acid sequence of SEQ ID NO: 25 or active fragment or homologue thereof. In one embodiment, the aldo-ketoreductase, oxidoreductase, aldehyde reductase or alcohol dehydrogenase includes the following conserved residues in the NADP binding pocket and active site: Arg214, Arg227, Arg281, Gln285, Gly279, Arg208 where the second number refers to the amino acid residue in the amino acid sequence of SEQ ID 25. In one embodiment, the exogenous nucleic acid comprises a nucleotide sequence of SEQ ID NO. 11.

In one embodiment, the non-naturally occurring microorganism further includes: a decarboxylase capable of the decarboxylation of pyruvate to yield acetaldehyde and carbon dioxide In various embodiments, the decarboxylase comprises a pyruvate decarboxylase (PDC), which may comprise an amino acid sequence of SEQ ID NO: 26 or an active fragment or homologue thereof; benzoylformate decarboxylase (BFD), which may comprises an amino acid sequence or SEQ ID NO: 27 or active fragment or homologue thereof; or alpha-detoacid decarboxylase (KDC), which may comprise an amino acid sequence of SEQ ID NO: 28 or active fragment or homologue thereof. The microorganism may alternatively or further express an enzyme identified in Table 3.

In one embodiment, one or more genes encoding an enzyme that utilizes pyruvate are deleted from the non-naturally occurring microorganism as compared to wild-type. In one embodiment, one or more genes encoding an alcohol dehydrogenase, a lactate dehydrogenase, or a pyruvate formate lyase are deleted from the non-naturally occurring microorganism as compared to wild-type.

Also provided is a method for producing 1,3-BDO that includes culturing a microorganism as described herein under conditions and for a sufficient period to time to produce 1,3-BDO. In one embodiment, the method is performed in a substantially anaerobic culture medium.

Also provided is a biosynthetic process that includes: condensing two acetaldehyde molecules to 3-hydroxybutanal using an enzyme from class aldolases; and selectively reducing 3-hydroxybutanal to 1,3-BDO using an enzyme belonging to the class aldo-ketoreductase, oxidoreductase, aldehyde reductase or alcohol dehydrogenase. In one embodiment, the process further includes producing acetaldehyde by a biosynthetic method. In one embodiment, the process further includes decarboxylating a pyruvate to obtain the acetaldehyde.

Also provided is a method of producing enantiopure (R)-1,3-BDO comprising culturing a non-naturally occurring microorganism as described herein or performing the biosynthetic process as described herein.

BRIEF DESCRIPTION OF THE DRAWINGS

FIG. 4 schematically shows a multiple sequence alignment of fifteen DERA (deoxyribose-5-phosphate aldolase) enzymes using MAFFT. A BLOSUM62 matrix was used. Five residues that lie in the phosphate-binding pocket of DERA are highlighted by the boxes and are based on comparison to TM1559 and EC1535. These residues are conserved to those found in DERA from *Thermotoga maritima* (TM1559), but differ to DERA from *Escherichia coli* (EC1535).

FIG. 5 schematically shows a multiple sequence alignment of fifteen DERA enzymes using MAFFT. A BLOSUM62 matrix was used. Four residues that lie in the active site and that play a role in forming the required Schiff-based intermediate with the donor acetaldehyde are highlighted by the boxes and are based on comparison to TM1559 and EC1535. These residues are strictly conserved in all DERA enzymes (except for D16 (number refers to EC1535 sequence) which is conserved in all sequences except for TM1559 which has a glycine residue).

FIG. 6 schematically shows a multiple sequence alignment of aldo-keto reductases.

FIG. 7 schematically shows a multiple sequence alignment of three decarboxylases.

DETAILED DESCRIPTION

Figure 1:
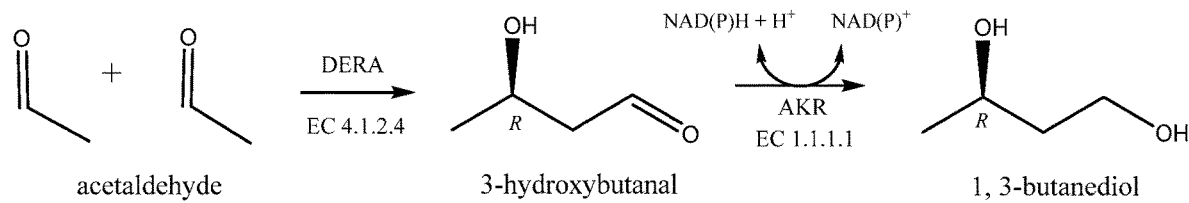
FIG. 1 shows a schematic of the conversion of acetaldehyde to 1,3-BDO according to one aspect of the present invention.

The present disclosure describes non-naturally occurring microorganisms that are engineered by expressing genes encoding enzymes involved in a novel biochemical pathway for conversion of acetaldehyde to 1,3-butanediol (1,3-BDO). The present disclosure also describes additional genetic modifications that can be used to improve the performance of the 1,3-BDO production pathway. The genetic modifications can be towards optimizing the expression system or to the non-natural organism for improvement of production metrics including yield, titre, and productivity. Additionally, genetic modifications can be aimed at improving the non-natural microorganism's characteristics including but not limited to tolerance to inhibitors found in the feedstocks, product tolerance, osmotolerance, and efficient product secretion.

Definitions

As used herein, the terms 1,3-BDO is used to refer to 1,3-butanediol, which is also known as butylene glycol, 1,3-butylene glycol, butane-1,3-diol, 1,3-dihydroxybutane, and in enantiopure form either as (R)-1,3-butanediol or (S)-1,3-butanediol.

As used herein, the terms 3-HB and 3HB have been used interchangeably to refer to 3-hydroxybutanal, which is also known as 3-hydroxybutaraldehyde, hydroxybutyraldehyde, and in enantiopure form as (R)-3-hydroxybutanal or (S)-3-hydroxybutanal.

As used herein, the term DERA refers to the enzyme deoxyribose-5-phosphate aldolase belonging to the class aldolases, the term AKR refers to the class aldo-ketoreductase, the term ADH refers to the enzyme alcohol dehydrogenase, the term PDC refers to the enzyme pyruvate decarboxylase, the term BFD refers to the enzyme benzoylformate decarboxylase, and the term KDC refers to the enzyme alpha-ketoacid decarboxylase.

As used herein "enzyme" includes proteins produced by a cell capable of catalyzing biochemical reactions. Further, unless context dictates otherwise, as used herein "enzyme" includes protein fragments that retain the relevant catalytic activity, and may include artificial enzymes synthesized to retain the relevant catalytic activity.

The expression "derived from" in relation to an enzyme or (poly)peptide denotes that the enzyme or poly(peptide) was isolated from a (micro)organism or that it includes all or a biologically active part of the amino acid sequence of an enzyme or (poly)peptide isolated or characterized from such a (micro)organism.

As used herein, the term "microorganism" is intended to mean any organism that exists as a microscopic cell and encompasses prokaryotic or eukaryotic cells or organisms having a microscopic size and includes bacteria, archaea and eubacteria of all species as well as eukaryotic microorganisms such as yeast and fungi. The term also includes cell cultures of any species (including e.g. plant and mammalian cells) that can be cultured for the production of a biochemical.

As used herein, the term "non-naturally occurring" when used in reference to a microorganism refers to a microorganism that has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon.

The term "endogenous" refers to a referenced molecule or activity that originates in a host microorganism. Similarly, the term when used in reference to expression of an encoding nucleic acid refers to expression of an encoding nucleic acid contained within the microorganism.

As used herein the term "exogenous" refers to molecules or activity that is introduced into a host microorganism. The molecule can be introduced, for example, by introduction of an encoding nucleic acid into the host genetic material such as by integration into a host chromosome or as non-chromosomal genetic material such as a plasmid. In reference to expression of an encoding nucleic acid the term refers to introduction of the encoding nucleic acid in an expressible form into the microorganism. When used in reference to a biosynthetic activity, the term refers to an activity that is introduced into a reference host organism. The source can be, for example, an encoding nucleic acid that expresses the activity following introduction into the host microorganism.

As used herein, "homologue" refers to a protein that is functionally equivalent i.e. has the same enzymatic activity as an enzyme having an amino acid sequence of the specified sequence identification number, but may have a limited number of amino acid substitutions, deletions, insertions or additions in the amino acid sequence. In order to maintain the function of the protein, the substitutions may be conservative substitutions, replacing an amino acid with one having similar properties.

In various aspects, a homologue of each enzyme refers to a protein which has an identity of at least 25%, at least 50%, at least 60%, at least 70%, at least 80%, at least 85%, at least 90%, at least 95% or at least 99% with the amino acid sequence of SEQ ID NO corresponding to the enzyme and retains enzymatic activity. Algorithms for determining sequence identity are publicly available and include e.g. BLAST available through the National Center for Biotechnology Information (NCBI). One skilled in the art can determine if the sequences are similar to a degree that indicates homology and thus similar or identical function.

A person skilled in the art can obtain a polynucleotide encoding a homologue of each enzyme by appropriately introducing substitution, deletion, insertion, and/or addition to the DNA of the enzyme which is composed of a nucleotide sequence disclosed herein, using methods such as site-specific mutagenesis (Nucleic Acid Res. 10, pp. 6487 (1982), Methods in Enzymol. 100, pp. 448 (1983), Molecular Cloning 2nd Edt., Cold Spring Harbor Laboratory Press (1989), PCR A Practical Approach IRL Press pp. 200 (1991)). The polynucleotide encoding a homologue of each enzyme can be introduced and expressed in a host to obtain the homologue.

Each of the enzymes described herein can be attached to an additional amino acid sequence as long as it retains an activity functionally equivalent to that of the enzyme. As mentioned above, it is understood that each enzyme or a homologue thereof may be a (poly)peptide fragment as long as it retains an activity functionally equivalent to that of the enzyme.

The term "heterologous" refers to a molecule or activity derived from a source other than the referenced species whereas "homologous" refers to a molecule or activity derived from the host microbial organism. Accordingly, exogenous expression of an encoding nucleic acid of the invention can use either or both a heterologous or homologous encoding nucleic acid.

As used herein, the term "operably linked" refers to a linkage between one or more expression control sequences and the coding region in a polynucleotide to be expressed in such a way that expression is achieved under conditions compatible with the expression control sequence.

1,3-BDO is used as an intermediate in the manufacture of polyester plasticizers and also finds use as solvent for flavors in food industry and in cosmetic industry applications. Additionally, optically pure (R)-1,3-BDO is used in synthesis of various optically active compounds such as pheromones, fragrances, and insecticides, and is an intermediate for synthesis of penems and carbepenems antibiotics [Zheng, R.-C., Ge, Z., Qiu, Z.-K., Wang, Y.-S. & Zheng, Y.-G. Asymmetric synthesis of (R)-1,3-butanediol from 4-hydroxy-2-butanone by a newly isolated strain *Candida krusei* ZJB-09162. *Applied microbiology and biotechnology* 94, 969-76 (2012)].

1,3-BDO may be produced using biotechnological route, mainly due to the opportunity for production of 1,3-butadiene catalytically from 1,3-BDO [Burgard, A. P., Burk, M. J. & Pharkya, P. Methods and organisms for converting synthesis gas or other gaseous carbon sources and methanol to 1 3 butanediol. (2011)]. 1,3-butadiene is a building block chemical with a potential market of over $22 billion USD, and may be used to manufacture rubber, latex and resins, and articles including one or more of these, for examples tires. Non-limiting examples of products produced using 1,3-BDO as a component or intermediate include organic solvents, polyurethane resins, polyester resins, and hypoglycaemic agents. Accordingly, in some embodiments, there is provided organic solvents, polyurethane resins, polyester resins, and hypoglycaemic agents having 1,3-BDO prepared according to processes described herein as a component or produced using 1,3-BDO prepared according to processes described herein as an intermediate.

In one aspect, there is provided a novel pathway for producing 1,3-BDO using enzymatic transformation using acetaldehyde as a precursor.

In one aspect, a pathway is disclosed that comprises: condensation of two acetaldehyde molecules to 3-hydroxybutanal using an enzyme from class aldolases; and selective reduction of 3-hydroxybutanal to 1,3-BDO using an enzyme belonging to the class aldo-ketoreductase/oxidoreductase/aldehyde reductase/alcohol dehydrogenase (EC 1.1.1.a). FIG. 1 shows the schematic of this pathway.

In another aspect, a pathway is disclosed that comprises: the production of acetaldehyde according to one or more of the pathways described below; condensation of two acetaldehyde molecules to 3-hydroxybutanal using an enzyme from class aldolases; and selective reduction of 3-hydroxybutanal to 1,3-BDO using an enzyme belonging to the class aldo-ketoreductase/oxidoreductase/aldehyde reductase/alcohol dehydrogenase (EC 1.1.1.a). See FIG. 2.

In some embodiments, the intermediate 3-hydroxybutanal produced from the novel pathway is in enantiomeric excess.

In some embodiments, the enantiomer of 3-hydroxybutanal produced in excess is (R)-3-hydroxybutanal.

In some embodiments, 1,3-BDO produced from the novel pathway is in enantiomeric excess.

In some embodiments, the enantiomer of 1,3-BDO produced in excess is (R)-1,3-BDO.

Figure 3:
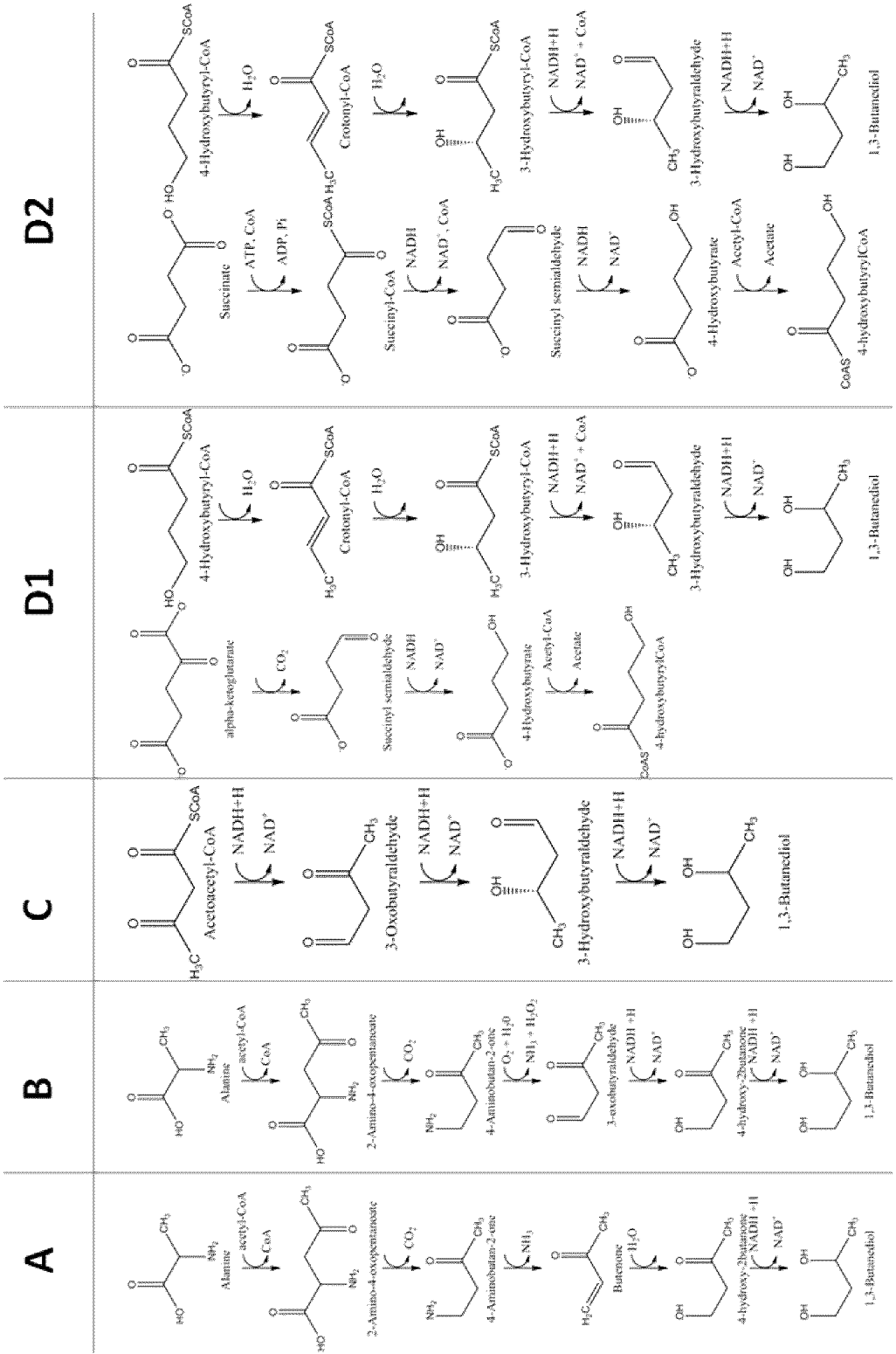
FIG. 3 schematically shows five published pathways for producing 1,3-BDO using fermentation.

In contrast to published multistep pathways, which require at least 4-5 steps, each catalyzed by a heterologous enzyme for the production of 1,3-BDO (FIG. 3 shows examples of such pathways), this pathway is shorter, requiring only two simple enzyme-catalyzed steps for the synthesis of 1,3-BDO. Further, most of the previously described pathways use precursors that are difficult to synthesize such as alanine, 4-hydroxybutyryl-CoA etc. The precursor acetaldehyde is advantageous in that it is simple to achieve high flux towards, as it is already present in the central carbon metabolism of both *Escherichia coli* and *Saccharomyces cerevisiae*.

In one aspect, a process is disclosed comprising, consisting of, or consisting essentially of condensing two aldehyde molecules using an aldolase enzyme as described herein.

The aldolases catalyze aldol condensation by stereocontrolled addition of a nucleophilic donor onto an electrophilic aldehyde acceptor. Due to the mechanistic requirements aldolases are quite specific for the nucleophilic donor component but show large flexibility in the acceptor range. Hence aldolases are categorized based on their nucleophilic donors. Different classes of aldolases are 1) acetaldehyde-dependent aldolase, 2) pyruvate/phosphoenolpyruvate-dependent aldolases, 3) dihydroxyacetone phosphate/dihydroxyacetone-dependent aldolases, and 4) glycine dependent aldolases.

In some embodiments, aldolases may be acetaldehyde dependent aldolases.

In some embodiments, the aldehydes may be donors or acceptors.

In some embodiments, the donors may include acetaldehyde (ethanal), propanal, 2-methylpropanal, methylglyoxal, lactaldehyde, glycolaldehyde, or acrolein.

In some embodiments, the donors may be non-aldehydes including pyruvate, propanone (acetone), glyoxylic acid, or 3-propenol.

In some embodiments, the acceptors may include one or more of acetaldehyde (ethanal), propanal, butanal, isobutanal, 2-methyl-1-butanal, 3-methyl-1-butanal, pentanal, hexanal, 3-methyl-1-pentanal, 4-methyl-1-pentanal, succinate semialdehyde, lactaldehyde, glycoldehyde, glyceraldehyde, 2-phenylacetaldehyde, cinnamaldehyde, glyoxal, glyoxylic acid, methyl glyoxal, acrolein, succindialdehyde, glutaraldehyde, adipaldehyde, malondialdehyde, malonic semialdehyde (3-oxopropionic acid), muconate semialdehyde, or 2-hydroxymuconate semialdehyde.

As described above, the condensation of two acetaldehyde molecules to 3-hydroxybutanal may be performed using an enzyme from class aldolases. In one embodiment, the enzyme from the class aldolases is a deoxyribose-5-phosphate aldolase (DERA) (EC 4.1.2.4.).

In some embodiments, DERA enzymes can be described as class I aldolases that form covalent Schiff base intermediates. In all studied structures, DERA adopts the classical eight-bladed TIM barrel fold. The oligomerisation state of DERA seems to depend on the temperature of the organism. For example, DERA from *E. coli* is a homodimer, whereas DERA from *Thermotoga maritima* is a homotetramer. The degree of oligomerization does not seem to affect catalysis but may affect stability under various conditions.

In one aspect, DERAs as described herein are derived from microorganisms of the genus *Bacillus*, *Escherichia*, *Thermotoga*, *Deinococcus*, *Listeria*, *Staphylococcus*, *Streptococcus*, and *Methanothermobacter*. In certain embodiments, the DERA is derived from *Bacillus halodurans*, *Bacillus cereus*, *Bacillus subtilis*, *Escherichia coli*, *Thermotoga maritima*, *Deinococcus radiodurans*, *Listeria monocytogenes*, *Staphylococcus aureus*, *Streptococcus pneumonia*, and *Methanothermobacter thermautotrophicus*. In one aspect, a DERA as used in a process described herein comprises an amino acid sequence of SEQ ID NO: 15, 16, 17, 18, 19, 20, 21, 22, 23, or 24 or active fragment or homologue thereof.

In some embodiments, the DERA is an enzyme comprising an amino acid sequence encoded by a DNA which comprises the nucleotide sequence of SEQ ID NO: 1, 2, 3, 4, 5, 6, 7, 8, 9, or 10.

In one aspect, the aldolase enzyme comprises the following conserved amino acid residues in the active site of the enzyme: lysine167, lysine 201, aspartic acid 16 and aspartic acid 102, where the number associated with each residue refers to the residue number in the amino acid sequence of *E. coli* DERA of the SEQ ID NO. 20 and corresponding codons in the nucleotide sequence of SEQ ID NO 2. FIG. 4 shows a multiple sequence alignment of the various DERA enzymes and highlights in boxes the key conserved residues described above, while FIG. 5 highlights the conserved residues in some DERA enzymes that may confer optimal acetaldehyde aldol condensation when compared to *E. coli* DERA.

In one aspect, enzymes belong to the Pfam database [Finn R. D. et al., Pfam: the protein families database Nucl. Acids Res. (1 Jan. 2014) 42 (D1): D222-D230] group PF01791 (DeoC/LacD family aldolase) include deoxyribose-5-phosphate aldolases, which also belong to the InterPro family IPR002915, IPR013785, IPR011343, and IPR028581. One skilled in the art can obtain protein sequences that belong to the InterPro and Pfam family of proteins such that they are homologues of DERA described herein.

The reduction of 3-hydroxybutanaldehyde to 1,3-BDO may be carried out by using appropriate alcohol dehydrogenase (ADH), aldo-ketoreductases, oxidoreductase, or aldehyde reductase using a reducing equivalent as cofactor, which in one embodiment, may be NADH or NADPH. In one embodiment, the ADH, AKR, oxidoreductase, or aldehyde reductase, however, is substantially specific towards 3-hydroxybutyraldehyde and does not act on acetaldehyde, thereby substantially avoiding or eliminating the production of ethanol as a side product.

In some embodiments, sources of encoding nucleic acids for the pathway enzymes described herein are not particularly restricted and may include any species where the encoded gene product can catalyze the relevant reaction. The enzymes may be derived from but not limited to the following species: *Agrobacterium tumefaciens*, *Bacillus cereus*, *Bacillus halodurans*, *Bacillus subtilis*, *Helicobacter pylori*, *Lactobacillus brevis*, *Pseudomonas aeruginosa*, *Pseudomonas putida*, *Pseudomonas synringae*, *Rhodopseudomonas palustris*, *Salmonella typhimurium*, *Saccharomyces cerevisiae*, *Clostridium acetobutylicum*. TABLE 1 includes exemplary aldo-keto reductase enzymes.

TABLE 1

| PROTEIN | GENEBANK ID | GI NUMBER | ORGANISM |
|---|---|---|---|
| AKR11B | CAB12792.1 | 2633288 | *Bacillus subtilis* |
| PA1127 | NP_249818.1 | 15596324 | *Pseudomonas aeruginosa* |
| AKR | WP_010898315 | 499200775 | *Bacillus halodurans* |
| AKR | NP_790200 | 28867581 | *Pseudomonas syringae* |

In one aspect, enzymes described herein can belong to the InterPro superfamily family IPR023210, IPR001395, IPR018170, and IPR020471, which describes the aldo-keto reductase family of enzymes that possess a beta-alpha-beta fold which comprises a parallel 8 beta/alpha barrel which contains the NADP-binding motif.

In one aspect, there is provided an alcohol dehydrogenase, aldo-keto reductases (AKR), oxidoreductase, or aldehyde reductase capable of selectively reducing 3-hydroxybutanal to 1,3-BDO. In one aspect, the source of this enzyme is not particularly restricted.

In one aspect, the enzymes described herein comprises the following conserved residues in the NADP binding pocket and active site: Arg214, Arg227, Arg281, Gln285, Gly279, Arg208 where the second number refers to the amino acid residue in the amino acid sequence of SEQ ID 25. The described key residues conserved among two exemplary aldo-keto reductases are shown in a multiple sequence alignment in FIG. 6.

In one aspect, aldo-keto reductases (AKRs) as described herein are derived from microoganisms of the genus *Pseudomonas*. In one aspect, an AKR as provided herein is derived from *Pseudomonas aeruginosa*. In one aspect, an AKR as used in a process described herein comprises an amino acid sequence of SEQ ID NO: 25 or active fragment or homologue thereof.

In some embodiments, the AKR is an enzyme comprising an amino acid sequence encoded by a DNA which comprises the nucleotide sequence of SEQ ID NO. 11.

The starting metabolite of the two-step pathway is acetaldehyde which is a common central metabolite, or may be produced by decarboxylation of pyruvate.

In some embodiments, acetaldehyde is produced by the decarboxylation of pyruvate by pyruvate decarboxylase (PDC) (EC 4.1.1.1) to yield acetaldehyde and carbon dioxide. PDC from *S. cerevisiae* has a broad substrate range for aliphatic 2-keto acids. It has been extensively studied, engineered and expressed in *E. coli* [Candy, J. M., Duggleby, R. G., & Mattick, J. S. (1991). Expression of active yeast pyruvate decarboxylase in. Journal of General Microbiology, (137), 5-9; Killenberg-Jabs, M., König, S., Hohmann, S., & Hübner, G. (1996). Purification and characterisation of the pyruvate decarboxylase from a haploid strain of *S. cerevisiae*. Biological Chemistry Hoppe-Seyler, 377(5), 313-7. PDC from *Zymomonas mobilis* also has a broad substrate range for 2-keto acids, and has been extensively studied and expressed in *Escherichia coli* [Pohl, M., Siegert, P., Mesch, K., Bruhn, H., & Grotzinger, J. (1998). Active site mutants of pyruvate decarboxylase from *Zymomonas mobilis*. Eur. J. Biochem., 257, 538-546; Candy, J. M., Koga, J., Nixon, P. F., & Duggleby, R. G. (1996). The role of residues glutamate-50 and phenylalanine-496 in *Zymomonas mobilis* pyruvate decarboxylase. The Biochemical Journal, 315, Pt 3, 745-51. Conway, T., Osman, Y. a, Konnan, J. I., Hoffmann, E. M., & Ingram, L. O. (1987). Promoter and nucleotide sequences of the *Zymomonas mobilis* pyruvate decarboxylase. Journal of Bacteriology, 169(3), 949-54. Siegert, P., Mesch, K., & Bruhn, H. (1998). Active site mutants of pyruvate decarboxylase from *Zymomonas mobilis*. Eur. J. Biochem., 257, 538-546.]. The sequence identifiers for the exemplary PDC described herein can be found in the TABLE 2 and searched for using the GenBank accession number.

TABLE 2

| PROTEIN | GENEBANK ID | GI NUMBER | ORGANISM |
|---|---|---|---|
| PDC | WP_011241152 | 499560369 | *Zymomonas mobilis* |
| PDC | P06169.7 | 30923172 | *Saccharomyces cerevisiae* |
| PDC | AEE86169 | 332660769 | *Arabidopsis thaliana* |
| PDC | KLA18896 | 821638028 | *Bacillus cereus* |

In one aspect, PDCs as described herein are derived from microorganisms of the genus *Zymomonas*. In one aspect the PDC is derived from *Zymomonas mobilis*. In one aspect, a PDC as used in a process described herein comprises an amino acid sequence of SEQ ID NO: 26 or active fragment or homologue thereof.

In one embodiment, the PDC is an enzyme comprising an amino acid sequence encoded by a DNA which comprises the nucleotide sequence of SEQ ID NO: 12.

Pyruvate decarboxylase that have also been shown to act on pyruvate for the production of acetaldehyde include but not limited to benzoylformate decarboxylase (BFD) (EC 4.1.1.7) derived from *Pseudomonas putida* and branched chain alpha-ketoacid decarboxylase (KDC) derived from *Lactococcus lactis* [Gocke, D., Graf, T., Brosi, H., Frindi-Wosch, I., Walter, L., Müller, M., & Pohl, M. (2009). Comparative characterisation of thiamine diphosphate-dependent decarboxylases. Journal of Molecular Catalysis B: Enzymatic, 61(1-2), 30-35]. In addition, mutants of PDC and BFD have been generated by site-directed mutagenesis including but not limited to: PDC I472A, PDC I476F, PDC I472A/I476F, BFD A460I, BFD F464I, and BFD A460I/F464I, have also shown activity on pyruvate towards acetaldehyde formation [Siegert, P., McLeish, M. J., Baumann, M., Iding, H., Kneen, M. M., Kenyon, G. L., & Pohl, M. (2005). Exchanging the substrate specificities of pyruvate decarboxylase from *Zymomonas mobilis* and benzoylformate decarboxylase from *Pseudomonas putida*. Protein Engineering, Design & Selection: PEDS, 18(7), 345-57].

In one embodiment, the BFD described herein comprises an amino acid sequence of SEQ ID NO: 27 or active fragment or homologue thereof, and that of the KDC of SEQ ID NO: 28 or active fragment or homologue thereof.

In one embodiment, the BFD is an enzyme comprising an amino acid sequence encoded by a DNA which comprises the nucleotide sequence of SEQ ID NO: 13.

In one embodiment, the KDC is an enzyme comprising an amino acid sequence encoded by a DNA which comprises the nucleotide sequence of SEQ ID NO: 14.

In other embodiments, homologues of enzymes described herein may be used in processes as described herein. FIG. 7 shows a multiple sequence alignment of PDC, BFD, and KDC described herein and highlights the protein domains required for the decarboxylation activity.

While in certain embodiments, acetaldehyde is obtained by the decarboxylation of pyruvate by PDC, in other embodiments, acetaldehyde is (alternatively or additionally) obtained by one or more of the reaction pathways identified in TABLE 3 below.

TABLE 3

| KEGG REACTION ID | ENZYME NAME | EC NUMBER | REACTION |
|---|---|---|---|
| R00025 | ethylnitronate:oxygen 2-oxidoreductase (nitrite-forming) | 1.13.12.16 | Ethylnitronate + Oxygen + Reduced FMN <=> Acetaldehyde + Nitrite + FMN + H2O |
| R00224 | pyruvate carboxy-lyase (acetaldehyde-forming) | 4.1.1.1 | Pyruvate <=> Acetaldehyde + CO2 |
| R00228 | acetaldehyde:NAD+ oxidoreductase (CoA-acetylating) | 1.2.1.10 | Acetaldehyde + CoA + NAD+ <=> Acetyl-CoA + NADH + H+ |
| R00326 | acetaldehyde:acceptor oxidoreductase | 1.2.99.6 | Acetaldehyde + Acceptor + H2O <=> Acetate + Reduced acceptor |
| R00710 | Acetaldehyde:NAD+ oxidoreductase | 1.2.1.3, 1.2.1.5 | Acetaldehyde + NAD+ + H2O <=> Acetate + NADH + H+ |
| R00711 | Acetaldehyde:NADP+ oxidoreductase | 1.2.1.4, 1.2.1.5, 1.2.1.- | Acetaldehyde + NADP+ + H2O <=> Acetate + NADPH + H+ |

TABLE 3-continued

| KEGG REACTION ID | ENZYME NAME | EC NUMBER | REACTION |
|---|---|---|---|
| R00746 | Ethanol:NADP+ oxidoreductase | 1.1.1.2, 1.1.1.71 | Ethanol + NADP+ <=> Acetaldehyde + NADPH + H+ |
| R00747 | 2-Phosphonoacetaldehyde phosphonohydrolase | 3.11.1.1 | Phosphonoacetaldehyde + H2O <=> Acetaldehyde + Orthophosphate |
| R00748 | ethanolamine-phosphate phosphate-lyase (deaminating; acetaldehyde-forming) | 4.2.3.2 | Ethanolamine phosphate + H2O <=> Acetaldehyde + Ammonia + Orthophosphate |
| R00749 | ethanolamine ammonia-lyase (acetaldehyde-forming) | 4.3.1.7 | Ethanolamine <=> Acetaldehyde + Ammonia |
| R00750 | 4-hydroxy-2-oxopentanoate pyruvate-lyase (acetaldehyde-forming) | 4.1.3.39 | Acetaldehyde + Pyruvate <=> 4-Hydroxy-2-oxopentanoate |
| R00751 | L-threonine acetaldehyde-lyase (glycine-forming) | 4.1.2.5 | L-Threonine <=> Glycine + Acetaldehyde |
| R00753 | (S)-lactate acetaldehyde-lyase (formate-forming) | 4.1.2.36 | (S)-Lactate <=> Formate + Acetaldehyde |
| R00754 | ethanol:NAD+ oxidoreductase | 1.1.1.1, 1.1.1.71 | Ethanol + NAD+ <=> Acetaldehyde + NADH + H+ |
| R00755 | Pyruvate decarboxylase, TPP dependent reaction | 4.1.1.1 | Acetaldehyde + Thiamin diphosphate <=> 2-(alpha-Hydroxyethyl)thiamine diphosphate |
| R00799 | Nitroethane:oxygen oxidoreductase | 1.7.3.1 | Nitrite + Acetaldehyde + Hydrogen peroxide <=> Nitroethane + Oxygen + H2O |
| R01019 | acetaldehyde:pyrroloquinoline-quinone oxidoreductase | 1.2.99.3 | PQQ + Acetaldehyde + H2O <=> PQQH2 + Acetate |
| R01066 | 2-deoxy-D-ribose-5-phosphate acetaldehyde-lyase (D-glyceraldehyde-3-phosphate-forming) | 4.1.2.4 | 2-Deoxy-D-ribose 5-phosphate <=> D-Glyceraldehyde 3-phosphate + Acetaldehyde |
| R01410 | | | Hydrogen cyanide + Acetaldehyde + Ammonia <=> alpha-Aminopropiononitrile + H2O |
| R01841 | 17alpha-Hydroxyprogesterone acetaldehyde-lyase | 4.1.2.30 | 17alpha-Hydroxyprogesterone <=> Androstenedione + Acetaldehyde |
| R02345 | 3-Hydroxybutan-2-one:D-ribose-5-phosphate aldehydetransferase | 2.2.1.4 | Acetoin + D-Ribose 5-phosphate <=> Acetaldehyde + 1-Deoxy-D-altro-heptulose 7-phosphate |
| R03723 | 24R,24(1)R)-fucosterol-epoxide acetaldehyde-lyase (desmosterol-forming) | 4.1.2.33 | ((24R,24(1)R)-Fucosterol epoxide <=> Desmosterol + Acetaldehyde |
| R05198 | ethanol:cytochrome c oxidoreductase | 1.1.2.8 | Ethanol + 2 Ferricytochrome c <=> 2 Ferrocytochrome c + Acetaldehyde + 2 H+ |
| R05380 | acetaldehyde hydro-lyase | 4.2.1.112 | Acetaldehyde <=> Acetylene + H2O |
| R05381 | diethanolamine ethanolamine-lyase (acetaldehyde-forming) | 4.3.3.- | Ethanolamine + Acetaldehyde <=> Diethanolamine |
| R05382 | triethanolamine diethanolamine-lyase (acetaldehyde-forming) | 4.3.3.- | Triethanolamine <=> Diethanolamine + Acetaldehyde |
| R05565 | | 1.14.15.- | 2 Atrazine + Oxygen <=> 2 Deethylatrazine + 2 Acetaldehyde |
| R05567 | | 1.14.15.- | 2 Deisopropylatrazine + Oxygen <=> 2 Deisopropyldeethylatrazine + 2 Acetaldehyde |
| R05811 | | 2.1.1.- | Cobalt-precorrin 5 + S-Adenosyl-L-methionine + H2O <=> Cobalt-precorrin 6 + S-Adenosyl-L-homocysteine + Acetaldehyde |
| R06171 | L-allo-threonine acetaldehyde-lyase (glycine-forming) | 4.1.2.5, 4.1.2.49 | L-Allothreonine <=> Glycine + Acetaldehyde |
| R06973 | | 4.1.1.- | 3-Oxopropanoate <=> Acetaldehyde + CO2 |
| R07247 | fluoroacetaldehyde:L-threonine aldehydetransferase | 2.2.1.8 | L-Threonine + Fluoroacetaldehyde <=> Acetaldehyde + 4-Fluoro-L-threonine |
| R07772 | cobalt-precorrin 5A acylhydrolase | 3.7.1.12 | Cobalt-precorrin 5A + H2O <=> Cobalt-precorrin 5B + Acetaldehyde |
| R08195 | D-threonine acetaldehyde-lyase (glycine-forming) | 4.1.2.42 | D-Threonine <=> Glycine + Acetaldehyde |
| R08196 | | | D-Allothreonine <=> Glycine + Acetaldehyde |
| R08516 | 17alpha-Hydroxypregnenolone acetaldehyde-lyase | 4.1.2.30 | 17alpha-Hydroxypregnenolone <=> Dehydroepiandrosterone + Acetaldehyde |
| R09127 | ethanol:cytochrome c oxidoreductase | 1.1.2.7 | Ethanol + 2 Ferricytochrome cL <=> Acetaldehyde + 2 Ferrocytochrome cL + 2 H+ |

TABLE 3-continued

| KEGG REACTION ID | ENZYME NAME | EC NUMBER | REACTION |
|---|---|---|---|
| R09156 | chloroethane, donor:oxygen oxidoreductase (dechlorinating, acetaldehyde-forming) | 1.13.12.-, 1.14.99.39 | Chloroethane + Oxygen + Reduced acceptor <=> Acetaldehyde + Hydrochloric acid + Acceptor + H2O |
| R09479 | ethanol:quinone oxidoreductase | 1.1.5.5 | Ethanol + Ubiquinone <=> Acetaldehyde + Ubiquinol |
| R09524 | acetyl-CoA:acetoin O-acetyltransferase | 2.3.1.190 | Acetoin + CoA + NAD+ <=> Acetaldehyde + Acetyl-CoA + NADH + H+ |
| R09552 | ethanol:N,N-dimethyl-4-nitrosoaniline oxidoreductase | 1.1.99.36 | Ethanol + N,N-Dimethyl-4-nitrosoaniline <=> Acetaldehyde + 4-(Hydroxylamino)-N,N-dimethylaniline |
| R09959 | 7,8-dihydroneopterin 3'-triphosphate acetaldehyde-lyase (6-carboxy-5,6,7,8-tetrahydropterin and triphosphate-forming) | 4.1.2.50 | 7.8-Dihydroneopterin 3'-triphosphate + H2O <=> 6-Carboxy-5,6,7,8-tetrahydropterin + Acetaldehyde + Triphosphate |
| R10285 | choline trimethylamine-lyase (acetaldehyde-forming) | 4.3.99.4 | Choline <=> Trimethylamine + Acetaldehyde + H+ |

The reaction IDs refer to Kyoto Encyclopedia of Genes and Genomes (KEGG) Database (http://www.genome.jp/kegg/) as of 13$^{th}$ May 2015.

In one embodiment, the processes as described herein are carried out with live cells. In other embodiments, the processes are carried out in vitro with lysed cells or with partially or substantially completely purified enzyme. In one embodiment, the processes are carried out with permeabilized cells. In other embodiments, methods are carried out in vitro and the enzyme is immobilized. Means and methods for immobilizing enzymes on different supports are well-known to the person skilled in the art.

Microorganisms expressing enzyme(s) as described herein may be provided in various forms, including live forms e.g. in in an aqueous solution or in culture medium or in "resting" forms such as in a freeze-dried or tablet form.

In one embodiment, the method is carried out in culture, with one or more host microorganisms, producing the pathway enzyme(s).

In one embodiment, there is provided a microorganism which is genetically modified so as to contain a nucleic acid molecule encoding an aldolase as described herein capable of condensing two acetaldehyde molecules.

In one embodiment, there is provided a non-naturally occurring microorganism having a 1,3-BDO pathway, wherein the microorganism comprises the following 1,3-BDO pathway enzymes: an aldolase that catalyzes condensation of two acetaldehydes to produce 3-hydroxybutanaldehyde; and an aldo-ketoreductase, oxidoreductase, aldehyde reductase or alcohol dehydrogenase that reduces 3-hydroxybutanaldehyde to 1,3-BDO; wherein the microorganism includes at least one exogenous nucleic acid encoding an enzyme from said 1,3-BDO pathway. In one embodiment, the microorganism further includes a PDC for decarboxylation of pyruvate to yield acetaldehyde and carbon dioxide. In one embodiment, the microorganism expresses an enzyme identified in Table 3 or an active fragment or homologue thereof for producing acetaldehyde. In one embodiment, more than one or all the nucleic acids are exogenous to the host microorganism.

In one embodiment, a microorganism used in a method according to one embodiment is a microorganism which is genetically modified so as to contain a nucleic acid molecule encoding an aldolase capable of condensing two acetaldehyde molecules to 3-hydroxybutanal. In one embodiment, the microogansim is genetically modified to contain a nucleic acid encoding a ketoreductase capable of reducing 3-hydroxybutanal to 1,3-BDO. In one embodiment, the microorganism is genetically modified to contain a nucleic acid encoding a PDC capable of decarboxylating pyruvate to yield acetaldehyde and carbon dioxide.

When reference is made to more than one exogenous nucleic acid being included in a microorganism, it is to be understood that this refers to the referenced encoding nucleic acids or biochemical activities and not the number of separate nucleic acids introduced into the host organism. As will be understood by those of skill in the art, such exogenous nucleic acids may be introduced into the host organism on separate nucleic acid molecules, on polycistronic nucleic acid molecules, or a combination thereof. For example, where two or more exogenous nucleic acids encoding different enzymatic activities are introduced into a host organism, the two or more exogenous nucleic acids can be introduced as a single nucleic acid, for example, on a single plasmid, on separate plasmids, can be integrated into the host chromosome at a single site or multiple sites, and still be considered as two or more exogenous nucleic acids.

As will be apparent to persons of skill in the art, depending on the host microorganism selected, nucleic acids for some or all of the 1,3-BDO pathway enzymes described can be introduced into the host organism. If the host microorganism endogenously expresses one or more of the pathway genes then it may not be necessary to introduce these genes, but only those nucleic acids encoding enzyme(s) in the pathway for which the microorganism is deficient. As will be apparent to persons of skill in the art, where a host microorganism is selected that expresses one or more of the pathway genes, the microorganism may be engineered such that the gene encoding the enzyme is overexpressed and/or genes encoding enzymes or proteins of competing pathways may be deleted.

As will be apparent to persons of skill in the art, the host microorganism can be engineered to increase co-factor pools of NADH and/or NADPH to improve metabolic flux towards 1,3-BDO. In one embodiment, if E. coli is to be used as the host organism, glucosephosphate isomerase (pgi) gene can be deleted to divert flux towards the pentose phosphate pathway to increase NADPH pools. Other strategies might involve switching the endogenous NADH-dependent glyceraldehyde-3-phosphate dehydrogenase (GAPDH) to the host E. coli strain with an exogenous NADPH-dependent glyceraldehyde-3-phosphate dehydrogenase derived from *Clostridium acetobutylicum*. In another method, an NADH kinase (Pos5P) can be introduced from *S. cerevisiae* into the host *E. coli* strain. The latter was successfully used to increase several products that are produced through NADPH-dependent pathways [Lee, W.-H., Kim, M.-D., Jin, Y.-S., & Seo, J.-H. (2013). Engineering of NADPH regenerators in *Escherichia coli* for enhanced biotransformation. *Applied Microbiology and Biotechnology*. 97(7):2761-72].

Figure 2:
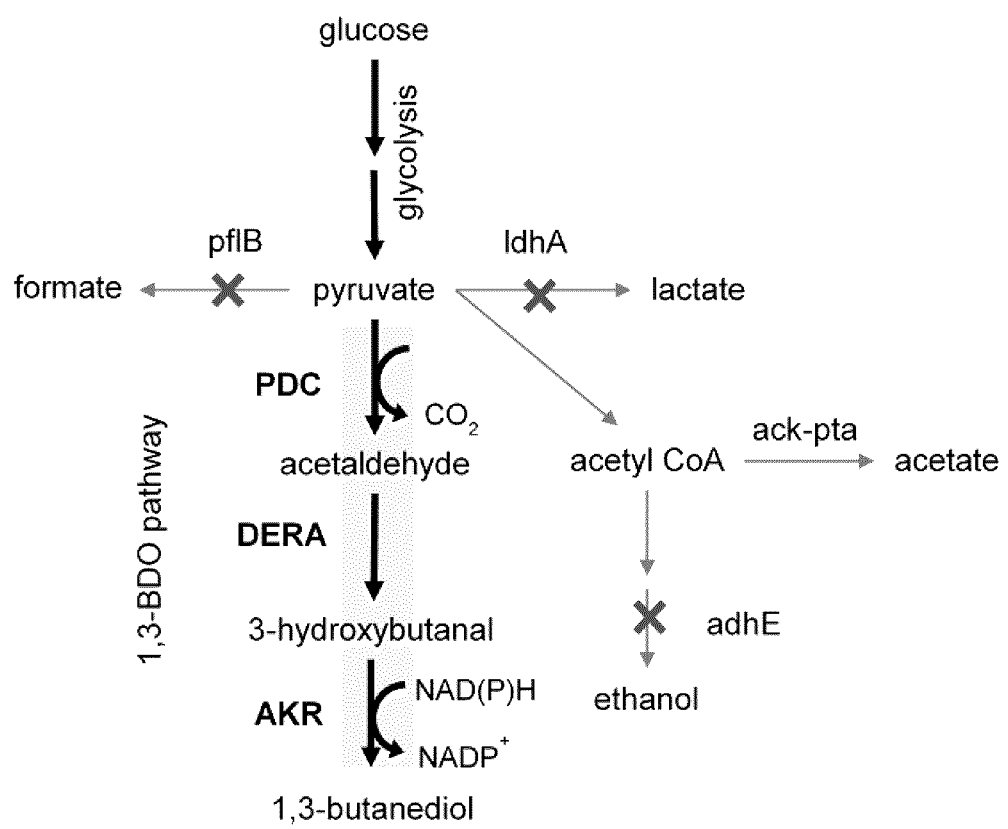
FIG. 2 shows the synthetic pathway for 1,3-butanediol production using glucose that may be implemented by genetically modified *E. coli*.

As will be apparent to persons of skill in the art, if *E. coli* is chosen as the host organism, NADH pools can be increased by limiting competing pathways though the deletion of genes encoding NADH-dependent enzymes, including but not limited to: alcohol dehydrogenase (adhE), lactate dehydrogenase (IdhA) and pyruvate-formate lyase (pflB) (See FIG. 2).

As will be apparent to persons of skill in the art, bacterial microcompartments (BMC) can be expressed in the host strain in order to increase cofactor pools and pathway metabolite concentrations, or decrease by-product formation from pathway intermediates. In addition, the BMC can reduce the toxic effect of the intermediate aldehydes on the cell and reduce their loss due to their volatile nature [Cai, F., Sutter, M., Bernstein, S. L., Kinney, J. N., & Kerfeld, C. A. (2014). Engineering Bacterial Microcompartment Shells: Chimeric Shell Proteins and Chimeric Carboxysome Shells. ACS Synth Biol. 2015, 4(4):444-53]. Examples of naturally occurring BMC's which have been expressed in *E. coli* include the propanediol utilization BMC (pdu) and ethanolamine utilization BMC (eut) from *Salmonella enterica*. The protein shells for these BMCs can be expressed without the internal pathways which would be replaced with the 1,3-1,3-BDO pathway enzymes.

Host microorganisms can be selected from, and the non-naturally occurring microorganisms generated in, for example, bacteria, yeast, fungus or any of a variety of other microorganisms may be used as a host organism.

In some embodiments, bacterial species may include: *Escherichia coli, Bacillus subtilis, Bacillus licheniformis, Bacillus cereus, Bacillus megaterium, Bacillus brevis, Bacillus pumilus, Corynebacterium glutamicum, Zymomonas mobilis, Clostridium acetobutylicum, Clostridium butylicum, Clostridium kluyveri, Clostridium autoethanogenum, Moorella thermoacetica, Clostridium aceticum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Pseudomonas fluorescens, Pseudomonas putida, Pseudomonas aeruginosa, Pseudomonas carboxidovorans (Oligotropha carboxidovorans), Pseudomonas stutzeri, Klebsiella pneumonia, Klebsiella oxytoca, Anaerobiospirillum succiniciproducens, Actinobacillus succinogenes, Mannheimia succiniciproducens, Rhizobium etli, Gluconobacter oxydans, Lactococcus lactis, Lactobacillus plantarum, Streptomyces coelicolor, Citrobacter freundii, Citrobacter amalonaticus, Acinetobacter calcoaceticus, Acinetobacter baylyi, Thermotoga maritima, Halobacterium salinarum, Serratia marcescens, Rhodospirillum rubrum*, ldeonella sp., *Rhodobacter capsulatus, Methylococcus capsulatus, Methylosinus trichosporium, Methylobacterium extorquens, Methylocystis* GB25, *Methylotrophus capsulatus, Methylomonas* sp. 16a, *Pyrococcus furiosus*.

In some embodiments, yeasts or fungi may include: *Saccharomyces cerevisiae, Schizosaccharomyces pombe, Saccharomycopsis crataegensis, Kluyveromyces lactis, Kluyveromyces marxianus, Aspergillus terreus, Aspergillus niger, Pichia stipitis, Pichia pastoris, Rhizopus arrhizus, Rhizopus oryzae, Yarrowia lipoiytica, Issatchenkia orientalis, Issatchenkia occidentalis, Candida lambica, Candida sorboxylosa, Candida zemplinina, Candida geochares, Pichia membranifaciens, Zygosaccharomyces kombuchaensis, Candida sorbosivorans, Candida vanderwaltii, Candida sorbophila, Zygosaccharomyces bisporus, Zygosaccharomyces lentus, Saccharomyces bayanus, Saccharomyces bulderi, Debaryomyces castellii, Candida boidinii, Candida etchellsii, Pichia jadinii, Pichia anomala, Penicillium chrysogenum*

In some embodiments, cyanobacteria may include: *Acatyochloris marina* MBIC11017, *Anabaena* sp. PCC 7120, *Anabaena variabilis* ATCC 29413, *Agmenellum quadruplicatum, Chlorobium tepidum* TLS, *Cyanothece* sp. ATCC 51142, *Gloeobacter violaceus* PCC 7421, *Microcystis aeruginosa* NIES-843, *Nostoc punctiforme* ATCC 29133, *Prochlorococcus marinus* MED4, *Prochlorococcus marinus* MIT9313, *Prochlorococcus* marinusSS120, *Prochlorococcus marinus* str. AS9601, *Prochlorococcus marinus* str. MIT 9211, *Prochlorococcus marinus* str. MIT 9215, *Prochlorococcus marinus* str. MIT 9301, *Prochlorococcus marinus* str. MIT 9303, *Prochlorococcus marinus* str. MIT 9312, *Prochlorococcus marinus* str. MIT 9515, *Prochlorococcus marinus* str. NATL1A, *Prochlorococcus marinus* str. NATL2A, *Rhodopseudomonas palustris* CGA009, *Synechococcus elongatus* PCC 6301, *Synechococcus elongatus* PCC 7942, *Synechococcus* sp. CC9311, *Synechococcus* sp. CC9605, *Synechococcus* sp. CC9902, *Synechococcus* sp. JA-2-3B, *Synechococcus* sp. JA-3-3Ab, *Synechococcus* sp. PCC 7002, *Synechococcus* sp. RCC307, *Synechococcussp*. WH 7803, *Synechococcus* sp. WH8102, *Synechocystis* sp. PCC 6803, *Thermosynechococcus elongatus* BP-1, *Trichodesmium erythraeum* IMS101.

In some embodiments, algae may include: *Botryococcus braunii, Chlamydomonas reinhardii, Chlorellasp., Crypthecodinium cohnii, Cylindrotheca* sp., *Dunaliella primolecta, Isochrysis* sp., *Monallanthus salina, Nannochlorissp., Nannochloropsis* sp., *Neochloris oleoabundans, Nitzschia* sp., *Phaeodactylum tricornutum, Schizochytrium* sp., *Tetraselmis sueica*.

However, in other embodiments, the host microorganism is not particularly restricted and a person skilled in the art may incorporate the enzymatic activity or activities into any suitable host organism using methods known in the art and/or as described herein.

*E. coli* and *S. cerevisiae* are particularly useful host organisms since they are well characterized microorganisms suitable for genetic engineering. Further, acetaldehyde is a natural metabolite of both *E. coli* and *S. cerevisiae* present in the central carbon metabolism of both species.

A nucleic acid molecule encoding enzymes as described herein can be used alone or as part of a vector. The nucleic acid molecules can include expression control sequences operably linked to the polynucleotide comprised in the nucleic acid molecule. These expression control sequences may be suited to ensure transcription and synthesis of a translatable RNA in bacteria or fungi. Expression refers to the transcription of the heterologous DNA sequence, preferably into a translatable mRNA. Regulatory elements ensuring expression in fungi and bacteria are known to those skilled in the art and encompass promoters, enhancers, termination signals, targeting signals and the like. Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used. Chemically inducible promoters may include but not limited to: IPTG-inducible promoters such as T7 or Ptrc, or tetracycline-inducible promoters such as $P_{LtetO-1}$ of which sequences are known to one skilled in the art.

An overview of different expression systems is for instance contained in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms, including E. coli and S. cerevisiae, are described in the literature known to those of skill in the art. Promoters permitting a particularly high expression of a downstream sequence are for instance the T7 promoter [Studier et al., Methods in Enzymology 185 (1990), 60-89], lacUV5, trp, trp-lacUV5 [DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25], lp1, rac [Boros et al., Gene 42 (1986), 97-100]. Termination signals for transcription are also described in the literature.

Inducible promoters which may provide higher polypeptide yields than constitutive promoters can be used. Suitably, in certain embodiments, a two-stage process may be used: the host cells are first cultured under optimum conditions up to a relatively high cell density; and transcription is then induced.

As will be understood by those of skill in the art, when two or more exogenous encoding nucleic acids are to be co-expressed, both nucleic acids may be inserted, for example, into one expression vector or into separate expression vectors. For single vector expression, the encoding nucleic acids can be operationally linked to a common expression control sequence or linked to different expression control sequences, such as one inducible promoter and one constitutive promoter.

It is to be understood that in one embodiment, a non-naturally occurring microorganism that produces a pathway intermediate or product, may be used in combination with another organism (or other organisms) expressing downstream or upstream pathway enzyme(s) to produce a desired product. For example, a wild-type or engineered organism can be used to produce and accumulate pyruvate, acetaldehyde, and/or 3-hydroxybutyralehdye. These intermediates can then be used as a substrate for another engineered organism expressing one or more of the 1,3-BDO pathway genes to convert to 1,3-BDO.

In other embodiments, a microorganism as provided herein can optionally be engineered to delete one or more byproduct or alternative pathways. Such exemplary pathways are shown with an X in FIG. 2. In one, embodiment, one or more genes encoding an alcohol dehydrogenase, a lactate dehydrogenase or a pyruvate formate lyase are deleted from a host microorganism. In one embodiment, the host microorganism is E. coli and one or all of the genes adhE, ldhA and pflB are deleted. Other genes native to E. coli and homologous to one or more of adhE, ldhA, and pflB can also be deleted. For example, one skilled in the art can identify, through multiple sequence alignment algorithms (such as ClustalW), aldehyde reductases and alcohol dehydrogenase that share similar function to adhE which catalyzes the reduction of acetaldehyde to ethanol. Aldehyde reductases or alcohol dehdyrogenases that are native to E. coli that show activity on acetaldehyde include but not limited to sequence data found in the TABLE 4 below.

TABLE 4

| Gene name | GenBank Accession | GI | Organism |
|---|---|---|---|
| yahK | P75691.1 | 2492774 | Escherichia coli |
| yqhD | Q46856.1 | 3025295 | Escherichia coli |
| yjgB | AAA97166.1 | 537111 | Escherichia coli |
| gldA | BAE77365.1 | 85676115 | Escherichia coli |
| ybbO | BAE76272.1 | 85674632 | Escherichia coli |
| yghA | BAE77062.1 | 85675809 | Escherichia coli |
| adhP | BAA15126.1 | 1742410 | Escherichia coli |
| fucO | BAE76871.1 | 85675618 | Escherichia coli |
| eutG | BAA16331.1 | 1799879 | Escherichia coli |
| yiaY | YP_026233.1 | 49176377 | Escherichia coli |
| eutE | NP_416950.1 | 16130380 | Escherichia coli |
| betA | NP_414845.1 | 16128296 | Escherichia coli |

However, one skilled in the art can also determine the activity of the aldehyde reductases and alcohol dehydrogenases described above on 3-hydroxybutyraldehyde, which is an intermediate in the 1,3-BDO pathway. In one embodiment, one or more of the aldehyde reductases and alcohol dehdyrogenases described herein that show substrate preference and activity towards 3-hydroxybutyraldehyde may be overexpressed in the host organism to improve 1,3-BDO production. One skilled in the art can also perform sequence similarity search to identify homologues derived from other organisms to the native aldehyde reductases and alcohol dehydrogenases in E. coli that show activity on 3-hydroxybutyraldehyde.

In some embodiments, the 1,3-BDO pathway may also produce side products, which may include acetate, ethanol, and acetoin. In certain embodiments, pathways for converting these side products into the acetaldehyde precursor are overexpressed. The following (TABLE 5) are pathways that can convert side-products, acetate, ethanol, and acetoin into acetaldehyde.

TABLE 5

| KEGG REACTION ID | ENZYME NAME | EC NUMBER | REACTION |
|---|---|---|---|
| R00228 | acetaldehyde:NAD+ oxidoreductase (CoA-acetylating) | 1.2.1.10 | Acetaldehyde + CoA + NAD+ <=> Acetyl-CoA + NADH + H+ |
| R00326 | acetaldehyde:acceptor oxidoreductase | 1.2.99.6 | Acetaldehyde + Acceptor + $H_2O$ <=> Acetate + Reduced acceptor |
| R00710 | Acetaldehyde:NAD+ oxidoreductase | 1.2.1.3, 1.2.1.5 | Acetaldehyde + NAD+ + $H_2O$ <=> Acetate + NADH + H+ |
| R00711 | Acetaldehyde:NADP+ oxidoreductase; | 1.2.1.4, 1.2.1.5, 1.2.1.- | Acetaldehyde + NADP+ + $H_2O$ <=> Acetate + NADPH + H+ |
| R00746 | Ethanol:NADP+ oxidoreductase; | 1.1.1.2, 1.1.1.71 | Ethanol + NADP+ <=> Acetaldehyde + NADPH + H+ |
| R01019 | acetaldehyde:pyrrolo-quinoline-quinone oxidoreductase | 1.2.99.3 | PQQ + Acetaldehyde + $H_2O$ <=> $PQQH_2$ + Acetate |
| R02345 | 3-Hydroxybutan-2-one:D-ribose-5-phosphate aldehydetransferase | 2.2.1.4 | Acetoin + D-Ribose 5-phosphate <=> Acetaldehyde + 1-Deoxy-D-altro-heptulose 7-phosphate |
| R05198 | ethanol:cytochrome c oxidoreductase | 1.1.2.8 | Ethanol + 2 Ferricytochrome c <=> 2 Ferrocytochrome c + Acetaldehyde + 2 H+ |
| R09127 | ethanol:cytochrome c oxidoreductase | 1.1.2.7 | Ethanol + 2 Ferricytochrome cL <=> Acetaldehyde + 2 Ferrocytochrome cL + 2 H+ |
| R09479 | ethanol:quinone oxidoreductase | 1.1.5.5 | Ethanol + Ubiquinone <=> Acetaldehyde + Ubiquinol |
| R09524 | acetyl-CoA:acetoin O-acetyltransferase | 2.3.1.190 | Acetoin + CoA + NAD+ <=> Acetaldehyde + Acetyl-CoA + NADH + H+ |
| R09552 | ethanol:N,N-dimethyl-4-nitrosoaniline oxidoreductase | 1.1.99.36 | Ethanol + N,N-Dimethyl-4-nitrosoaniline <=> Acetaldehyde + 4-(Hydroxylamino)-N,N-dimethylaniline |

*The reaction IDs refer to Kyoto Encyclopedia of Genes and Genomes (KEGG) Database (http://www.genome.jp/kegg/) as of 13$^{th}$ May 2015.

In one embodiment, pyruvate used in according to embodiments of the present invention is produced from renewable feedstock (such as glucose). In one embodiment, the host organism is provided with a feedstock of sugars. Such sources include, for example, sugars such as glucose, xylose, arabinose, galactose, mannose, fructose, starch, and combinations thereof. Glucose can be obtained from various carbohydrate-containing sources including conventional biorenewable sources such as corn (maize), wheat, potato, cassava and rice as well as alternative sources such as energy crops, plant biomass, agricultural wastes, forestry residues, sugar processing residues and plant-derived household wastes.

Sources of carbohydrate include renewable feedstocks and biomass, e.g. cellulosic biomass, hemicellulosic biomass and lignin feedstocks. Other renewable feedstocks and biomass will be known to persons of skill in the art.

Biorenewable feedstock sources that may be used in accordance with the present invention include any renewable organic matter that includes a source of carbohydrates. These include, for example, grasses, trees (hardwood and softwood), vegetation and crop residues. Other sources can include, for example, waste materials (e.g., spent paper, green waste, municipal waste, etc.). Suitable carbohydrates, including glucose, may be isolated from biorenewable materials using methods that are known in the art. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007; Furia, *Starch in the Food Industry*, Chapter 8, CRC *Handbook of Food Additives* 2$^{nd}$ Edition CRC Press, 1973. See also chapters devoted to Starch, Sugar and Syrups within *Kirk-Othmer Encyclopedia of Chemical Technology* 5$^{th}$ Edition, John Wiley and Sons 2001. Processes to convert starch to glucose are also well known in the art, see, for example, Schenck, "Glucose and Glucose containing Syrups" in *Ullmann's Encyclopedia of Industrial Chemistry*, Wiley-VCH 2009. Furthermore, methods to convert cellulose to glucose are known in the art, see, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007.

Alternative carbon sources may be crude glycerol obtained from biodiesel production plants, lactic acid obtained from degradation of waste poly-lactic acid, lactose or cheese whey permeate obtained from dairy industry, glucosamine obtained from chitin rich waste. The carbon sources may also be fatty acids and their esters (monoglycerides, diglycerides and triglycerides) obtained from plants or plant products such as canola oil, coconut oil, corn oil, olive oil, palm oil, safflower oil, peanut oil, soybean oil, sesame oil, sunflower oil and combinations thereof.

Another carbon source may be synthesis gas or "syngas", which is primarily a mixture of $H_2$ and CO may contain $CO_2$ and which is a product of the gasification of organic or fossil fuel based carbonaceous materials.

C1 compounds, such as carbon monoxide (CO), carbon dioxide ($CO_2$), and methane ($CH_4$) can be derived as feedstocks from wastes gases from industry such as steel manufacture, oil refining, coal, and natural gas, shale gas, biogas, and methane hydrates, as well as in the form of synthesis gas (or syngas) produced from gasification of sustainable resources such as biomass and domestic waste and agricultural wastes.

Additional sustainable carbon sources can be achieved by using electrochemical reduction of $CO_2$ to formic acid or oxalic acid, and using these compounds as carbon sources in fermentation.

Currently six different pathways are known for carbon fixation: reductive pentose phosphate pathway (Calvin) cycle, reductive acetyl-CoA (Wood-Ljungdahl) pathway, reductive citric acid cycle, 3-hydroxypropionate bicycle, dicarboxylate/4-hydroxybutyrate cycle, and 3-hydroxypropionate/4-hydroxybutyrate cycle [Fuchs G, 2011 Alternative pathways of carbon dioxide fixation: insights into the early evolution of life? Annual Reviews in Microbiology, 65:631-658]. In addition to these pathways, synthetic carbon-fixation pathways can be used which fall within the family of malonyl-CoA-oxaloacetate-glyoxylate (MOG) family of pathways [Bar-Even et al., Design and Analysis of synthetic carbon fixation pathways. Proceedings of National Academy of Sciences USA, 2010, 107:8889-8894].

In one embodiment, the processes as provided may be carried out in a fermenter.

The engineered organism can be cultivated in a variety of reactor systems, and the process can be carried out in different modes of operations. The most commonly used bioreactor is a stirred tank bioreactor or aerated fermenter. The fermenter is equipped with sterile air supply, the mixing of bubble dispersion is achieved by mechanical agitation, and the temperature may be maintained using a jacket or coil that circulates steam or cooling water. For aerated vessels, high height/diameter ratio (>3) may be chosen to increase the contact time between the bubbles and liquid phase. Other variations of bioreactors are airlift bioreactor where mixing is achieved without mechanical agitation, and packed bed or fluidized bed bioreactors which are used when the biocatalyst is immobilized.

The fermentation can be carried out in three different modes: batch, fed-batch and continuous mode. A standard batch bioreactor is considered a "closed" system. In batch mode, all the media components are added to bioreactor while ensuring the sterility. Once the medium has been prepared, the bioreactor is inoculated with an appropriate inoculum and the fermentation is allowed to proceed until the end without any changes to the medium, i.e., without feeding of any additional components. Components such as acid and/or base can, however, be added to maintain the pH, and air/oxygen can be added to maintain the dissolved oxygen levels. In batch fermentation biomass and product concentration change over time until the fermentation is complete. The cells undergo classical lag-phase, exponential growth-phase, stationary phase growth, followed by death phase.

A variation of the batch mode is fed-batch mode where the nutrients including the carbon source is added to the fermenter as the process progresses.

In addition to batch or fed-batch mode, continuous mode of fermentation can also be used. A continuous system is considered to be "open" system in contrast to the batch mode. In continuous mode, defined production medium is added continuously to the bioreactor and equal amount of bioreactor contents are removed at the same rate. Continuous operation can be carried out in a chemostat where the vessel contents, including the cells are removed, or in a bioreactor that uses perfusion culture, which allows recycling of the viable cells back to the bioreactor, allowing high cell densities to be achieved.

The commonly used fermenter designs and different operation modes are very well-established in the literature [Biochemical Engineering Fundamentals, $2^{nd}$ Ed. J. E. Bailey and D. F. Ollis, McGraw Hill, N.Y., 1986; Development of Sustainable Bioprocesses: Modeling and Assessment, E. Heinzle, A. P. Biwer and C. L. Cooney, John Wiley & Sons, Ltd., 2006; Bioprocess Engineering: Basic Concepts, $2^{nd}$ Ed., M. L. Shuler and F. Kargi, Prentice Hall, 2001].

Batch, fed-batch or continuous fermentation procedures may be employed.

In one embodiment, processes as provided herein are carried out in substantially anaerobic conditions. "Substantially anaerobic" when used in reference to a culture or growth condition means, in one embodiment, that the amount of oxygen is less than about 10% of saturation for dissolved oxygen in liquid media. In one embodiment, the term includes sealed chambers of liquid or solid medium maintained with an atmosphere less than about 1% oxygen. In another embodiment, the processes are conducted under substantially aerobic conditions. As used herein the term "substantially aerobic" when used in reference to a culture or growth condition means, in one embodiment, that the amount of oxygen is equal to or greater than about 10% of saturation for dissolved oxygen in liquid media. In one embodiment, the term includes sealed chambers of liquid or solid medium maintained with an atmosphere greater than about 1% oxygen. Methods of maintaining aerobic or anaerobic conditions within a bioreactor are known to those of skill in the art.

As will be understood by a person of skill in the art, various components may be added to the culture medium to support growth of the microorganism and/or the metabolic processes described herein, including, for example, nutrients, pH modifiers, osmoprotectants.

The organisms can be grown in any suitable medium for growth such as Luria-Bertani broth, Terrific broth or yeast extract-peptone-dextrose (YPD) medium. For production, depending up on the choice of the host, synthetic minimal media such as M9 minimal medium, yeast synthetic minimal medium, yeast nitrogen base, BG-11, or variations thereof can be used. A suitable minimal medium must contain at least one carbon source, at least one nitrogen source, salts, cofactors, buffers, and other components required to grow and maintain the recombinant microorganism. The carbon source can be one or more of the carbon sources described previously, the nitrogen source can be an ammonium salt or nitrate salt including but not limited to $(NH_4)_2SO_4$, $NH_4Cl$, $(NH_4)_2HPO_4$, $NH_4OH$, $KNO_3$, $NaNO_3$. The medium may be supplemented with complex or organic nitrogen sources such as urea, yeast extract, casamino acids, peptone, tryptone, soy flour, corn steep liquor, or casein hydrolysate. Additionally, the minimal medium can be supplied with trace metals including but not limited to $H_3BO_3$, $MnCl_2$, $ZnSO_4$, $Na_2MoO_4$, $CuSO_4$, $Co(NO_3)_2$, $CuCl_2$, $ZnCl_2$, $CoCl_2$, $FeCl_3$, KI. The minimal medium may be supplemented with vitamins and/or non-vitamin compounds including but not limited to biotin, pantothanate, folic acid, inositol, nicotinic acid, p-aminobenzoic acid, pyridoxine, riboflavin, thiamine, cyanocobalamin, citric acid, ethylenediamine tetraacetic acid (EDTA), ferric ammonium citrate. The medium can be supplied by carbon dioxide either by direct sparging or in the form of $NaHCO_3$, or $Na_2CO_3$.

Depending upon the host organism used the minimal medium may suitably have a pH range between pH 2.0-pH 10.0.

The fermentation may be carried out in temperature ranging from 25° C. to 42° C. Higher temperature may be used if the host organism chosen is thermophilic where the cultivation temperature could be as high as 80° C.

The fermentation may be carried out under aerobic, microaerobic, or anaerobic conditions. It could also be carried out under two different phases involving aerobic growth-phase and a microaerobic or anaerobic production phase. Sterile air or oxygen may be introduced to maintain the desired dissolved oxygen levels in the medium.

The amount of product in the medium can be determined using methods known in the art such as High Performance Liquid Chromatography (HPLC), Gas Chromatography (GC), Liquid Chromatography-Mass Spectrometry (LC-MS), Gas Chromatography-Mass Spectrometry (GC-MS).

Methods of assaying for the production of 1,3-butanediol are known to those of skill in the art and further are exemplified in Example 3. For example, product, intermediate and byproduct formation can be analyzed by methods such as HPLC (High Performance Liquid Chromatography) equipped with a refractive index and/or photodiode array detector(s), GC-MS (Gas Chromatography-Mass Spectroscopy), GC-FID (Gas Chromatography-Flame Ionization Detector) and LC-MS (Liquid Chromatography-Mass Spectroscopy). Individual enzymatic activities from the exogenous DNA sequences can also be assayed using methods well known in the art.

In some embodiments, processes as disclosed herein further include purifying the product of the processes, for e.g. 1,3-BDO. Such methods of purification are known to those of skill in the art and include e.g. by liquid extraction, filtration, distillation or evaporation. Isolation of compound from the fermentation broth depends on the final purity of the compound required. The separation techniques may include: centrifugation, microfiltration, ultrafiltration, nanofiltration, evaporation, crystallization, distillation, and ion-exchange. Typical downstream processing operation would include a series of processes including separation of cells using centrifugation or microfiltration, removal of additional solids in the broth using ultrafiltration, removal of salts from the broth using nanofiltration, ion-exchange, or evaporative crystallization, and finally purification of 1,3-BDO using distillation.

As will be understood by persons of skill in the art, in one embodiment, microorganisms as described herein may be produced to secrete the resulting product, whether by choosing a host organism with a secretory signal corresponding to the product or by engineering the host organism to provide for the same. For example, membrane-bound transporter proteins can be overexpressed in the host organism to improve the secretion of 1,3-BDO to the fermentation broth, including but not limited to yhjX gene encoding a pyruvate-inducible inner membrane protein and putative transporter which belongs to the major facilitator superfamily of proteins, and the product can be recovered from the culture medium. In other embodiments, the product may be extracted from the microorganism. In one method, the microorganisms may be ruptured and the culture medium or lysate may be centrifuged to remove particulate cell debris, and the membrane and soluble protein fractions may be separated if necessary.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

The embodiments of the invention described above are intended to be exemplary only. The scope of the invention is therefore intended to be limited solely by the scope of the appended claims.

EXAMPLES

The present invention is further described in the following examples. The examples provided are only illustrative of the invention and not in a limiting sense.

The strains and plasmids constructed and used in the examples provided in the document are listed in the following TABLE 6:

TABLE 6

| Strain designation | Genotype |
| --- | --- |
| Wild type | E. coli MG 1655 |
| LMSE-25 | E. coli MG1655 ΔadhE, ΔldhA, ΔpflB |
| LMSE-21 | LMSE-25 with pTrc99A |
| ecBD-5 | LMSE-25 with pBD3 |
| ecBD-6 | Wild type with pBD3 |
| Plasmids | |
| Empty vector | pTrc99A |
| pBD3 | pTrc99A + BH1352 + PA1127 + PDC |

Example 1: Selection of DERA Enzyme for 1,3-Butanediol Pathway

This example describes screening, selection and characterization of enzyme candidates for 1,3-BDO pathway.

The first step in the 1,3-BDO biosynthetic pathway is the condensation of two acetaldehyde molecules by deoxyribose-5-phosphate aldolase to generate 3-hydroxybutanal (3HB). To identify the aldolase that could condense the two acetaldehyde molecules, a list of 72 class I aldolase homologues or putative aldolases was identified based on sequence similarity to E. coli deoxyribose-5-phosphate aldolase (DERA). These 72 putative aldolases are listed in TABLE 7.

TABLE 7

| Target | Genome | Gene ORF | GI | PDB Status |
|---|---|---|---|---|
| AA0111 | *Aquifex aeolicus* | deoC | 15605723 | 1MZH Identity 100% |
| AA1079 | *Aquifex aeolicus* | na | 15606691 | 2QJI Identity 58% |
| AF0108 | *Archaeoglobus fulgidus* | AF0108 | 2650540 | 2QJI Identity 63% |
| AF0230 | *Archaeoglobus fulgidus* | AF0230 | 2650411 | 2QJI Identity 47% |
| APE0011 | *Aeropyrum pernix* | APE0011 | 5103399 | 1OK6 Identity 40% |
| APE2437 | *Aeropyrum pernix* | APE2437 | 5106141 | 1N7K Identity 100% |
| ATC0125 | *Agrobacterium tumefaciens* C58 | deoC | 17934050 | 1P1X Identity 54% |
| ATC0125 | *Agrobacterium tumefaciens* C58 | deoC | 17934050 | 1P1X Identity 53% |
| AU05279 | *Aspergillus fumigatus* | na | 71000527 | 3OA3 Identity 38% |
| AU12363 | *Aspergillus fumigatus* | na | 70986744 | 3NGJ Identity 27% |
| BAS1754 | *Bacillus anthracis* str. Sterne | na | 49184766 | 3NGJ Identity 58% |
| BAS2771 | *Bacillus anthracis* str. Sterne | na | 49185777 | 3GND Identity 42% |
| BCE1975 | *Bacillus cereus* ATCC 10987 | dra | 42781044 | 3NGJ Identity 58% |
| BCE3019 | *Bacillus cereus* ATCC 10987 | na | 42782075 | 3GKF Identity 42% |
| BH1352 | *Bacillus halodurans* | dra | 15613915 | 3NGJ Identity 61% |
| BSU3938 | *Bacillus subtilis* | | 225185466 | 3NGJ Identity 58% |
| CT215 | *Chlamydia trachomatis* | dhnA | 15604935 | 1OK6 Identity 24% |
| CV3701 | *Chromobacterium violaceum* | deoC | 34499156 | 1P1X Identity 68% |
| DHC1073 | *Dehalococcoides* CBDB1 | na | 73749029 | 3KAO Identity 29% |
| DRD1181 | *Deinococcus radiodurans* | DR1205 | 6458945 | 3R13 Identity 54% |
| EC1535 | *Escherichia coli* K12 | deoC | 16132198 | 1P1X Identity 100% |
| EC1726 | *Escherichia coli* K12 | yneB | 16129476 | 3GKF Identity 100% |
| EC1734 | *Escherichia coli* K12 | yihT | 16131721 | 1TO3 Identity 87% |
| EC2144 | *Escherichia coli* K12 | b2097 | 90111385 | 1OK6 Identity 20% |
| HL0239 | *Halobacterium* sp | na | 15789585 | 2QJI Identity 43% |
| HL0521 | *Halobacterium* sp | na | 15789872 | 1OK6 Identity 46% |
| HL1382 | *Halobacterium* sp | deoC | 15790758 | 3R13 Identity 43% |
| LB1413 | *Lactobacillus brevis* | na | na | 3NGJ Identity 49% |
| LMO0539 | *Listeria monocytogenes* | na | 16802582 | 3KAO Identity 52% |
| LMO1995 | *Listeria monocytogenes* | dra | 16804034 | 3NGJ Identity 61% |
| LPG1433 | *Legionella pneumophila* Philadelphia 1 | deoC | 52841663 | 1KTN Identity 32% |
| MG050 | *Mycoplasma genitalium* | MG050 | 1045723 | 3NGJ Identity 40% |
| MJ0404 | *Methanococcus jannaschii* | na | 15668576 | 2QJI Identity 100% |
| MJ1609 | *Methanococcus jannaschii* | na | 15669781 | 4MOZ Identity 53% |
| MTH0579 | *Methanothermobacter thermautotrophicus* | MTH0579 | 2621657 | 2QJI Identity 62% |
| MTH0818 | *Methanothermobacter thermautotrophicus* | MTH0818 | 2621909 | 3R13 Identity 55% |
| PH0082 | *Pyrococcus horikoshii* | PH0082 | 3256468 | 2QJI Identity 34% |
| PS0950 | *Pseudomonas syringae* tomato DC3000 | deoC | 28868193 | 1P1X Identity 38% |
| PSPH0865 | *Pseudomonas syringae* phaseolicola 1448A | deoC | 71733380 | 1P1X Identity 37% |
| RHA06207 | *Rhodococcus* sp. RHA1 | na | 111018361 | 3FOK Identity 57% |
| RHA07557 | *Rhodococcus* sp. RHA1 | na | 111019087 | 3NDO Identity 60% |
| SA0138 | *Staphylococcus aureus* | dra | 15923128 | 3NGJ Identity 53% |
| SA2137 | *Staphylococcus aureus* | na | 15925127 | 3NGJ Identity 52% |
| SA2192 | *Staphylococcus aureus* | lacD | 15925182 | 3KAO Identity 100% |
| SAV3348 | *Streptomyces avermitilis* | deoC | 29829888 | 1KTN Identity 33% |
| SAV5342 | *Streptomyces avermitilis* | na | 29831882 | 3FOK Identity 46% |
| SAV7151 | *Streptomyces avermitilis* | na | 29833691 | 3FOK Identity 51% |
| SC4702 | *Streptomyces coelicolor* | na | 21223288 | 1KTN Identity 33% |
| SC6677 | *Streptomyces coelicolor* | na | 21225263 | 3FOK Identity 50% |
| SF1578 | *Shigella flexneri* 2a | na | 24112949 | 3GKF Identity 98% |
| SF2159 | *Shigella flexneri* 2a | na | 24113475 | 1OK6 Identity 22% |
| SF3953 | *Shigella flexneri* 2a | yihT | 24115171 | 1TO3 Identity 86% |
| SF4413 | *Shigella flexneri* 2a | deoC | 56480609 | 1P1X Identity 99% |
| SM2560 | *Sinorhizobium meliloti* | na | 15966313 | 3NGJ Identity 31% |
| SM5179 | *Sinorhizobium meliloti* | na | 16264228 | 2QJI Identity 30% |
| SM5503 | *Sinorhizobium meliloti* | deoC | 16264552 | 1ktnB00 Identity 31% |
| SO1217 | *Shewanella oneidensis* | deoC | 24372798 | 1P1X Identity 63% |
| SP0843 | *Streptococcus pneumoniae* TIGR4 | na | 15900730 | 3NGJ Identity 59% |
| SP1190 | *Streptococcus pneumoniae* TIGR4 | na | 15901055 | 3KAO Identity 75% |
| SPA0711 | *Salmonella enterica* Paratypi ATCC9150 | fbaB | 56412946 | 1OK6 Identity 16% |
| SPA3863 | *Salmonella enterica* Paratypi ATCC9150 | yihT | 56415868 | 1TO3 Identity 99% |
| SPA3921 | *Salmonella enterica* Paratypi ATCC9150 | yneB | 56415923 | 3GKF Identity 89% |
| SPA4381 | *Salmonella enterica* Paratypi ATCC9150 | deoC | 56416341 | 1P1X Identity 94% |
| SSO3226 | *Sulfolobus solfataricus* | SSO3226 | 13816668 | 2QJI Identity 34% |
| STU0806 | *Streptococcus thermophilus* LMG18311 | na | 55820857 | 3R13 Identity 56% |
| TA0684 | *Thermoplasma acidophilum* | TA0684 | 10639970 | 1VCV Identity 37% |
| TM1559 | *Thermotoga maritima* | TM1559 | 4982126 | 3R13 Identity 100% |
| TSTM2012 | *Salmonella typhimurium* LT2 | fbaB | 16765470 | 1OK6 Identity 16% |
| TSTM3768 | *Salmonella typhimurium* LT2 | yihT | 16767287 | 1TO3 Identity 99% |
| TSTM3821 | *Salmonella typhimurium* LT2 | yneB | 16767344 | 3GKF Identity 89% |
| TSTM4263 | *Salmonella typhimurium* LT2 | deoC | 16767808 | 1P1X Identity 94% |
| TTC0823 | *Thermus thermophilus* HB27 | na | 46199129 | 1UB3 Identity 98% |

Furthermore, three residues in the active site of *E. coli* have been shown to play a crucial role in forming a Schiff-based intermediate with the donor aldehyde that is critical for the aldol condensation to occur. These residues are: Lys167, Lys201, and Asp102 (the number refers to the residue number in *E. coli* DERA). A multiple sequence alignment was performed using MAFFT to find 34 of the 72 enzymes that had the aforementioned residues strictly conserved. The list of these 34 selected enzymes is shown in TABLE 8.

were: N21K, Y49N, A71C or V, K172F, N176H or G (where the first letter and number refer to the residue and its location in EC1535, and the final letter refers to the corresponding residue in TM1559). Based on these residues, the list was narrowed further to 15 enzymes with potential for higher acetaldehyde aldol condensation activity (TM1559 and EC1535 were also included in the list for comparison). A multiple sequence alignment of the fifteen DERAs chosen for further analysis is shown in FIG. 4 and listed in TABLE 9.

TABLE 8

| Target | Genome | Gene ORF | GI | PDB Status |
|---|---|---|---|---|
| AA0111 | *Aquifex aeolicus* | deoC | 15605723 | 1MZH Identity 100% |
| APE2437 | *Aeropyrum pernix* | APE2437 | 5106141 | 1N7K Identity 100% |
| ATC0125 | *Agrobacterium tumefaciens* C58 | deoC | 17934050 | 1P1X Identity 54% |
| AU05279 | *Aspergillus fumigatus* | na | 71000527 | 3OA3 Identity 38% |
| AU12363 | *Aspergillus fumigatus* | na | 70986744 | 3NGJ Identity 27% |
| BAS1754 | *Bacillus anthracis* str. Sterne | na | 49184766 | 3NGJ Identity 58% |
| BCE1975 | *Bacillus cereus* ATCC 10987 | dra | 42781044 | 3NGJ Identity 58% |
| BH1352 | *Bacillus halodurans* | dra | 15613915 | 3NGJ Identity 61% |
| BSU3938 | *Bacillus subtilis* | | 225185466 | 3NGJ Identity 58% |
| CV3701 | *Chromobacterium violaceum* | deoC | 34499156 | 1P1X Identity 68% |
| DRD1181 | *Deinococcus radiodurans* | DR1205 | 6458945 | 3R13 Identity 54% |
| HL1382 | *Halobacterium* sp | deoC | 15790758 | 3R13 Identity 43% |
| LB1413 | *Lactobacillus brevis* | na | na | 3NGJ Identity 49% |
| LMO1995 | *Listeria monocytogenes* | dra | 16804034 | 3NGJ Identity 61% |
| LPG1433 | *Legionella pneumophila* Philadelphia 1 | deoC | 52841663 | 1KTN Identity 32% |
| MG050 | *Mycoplasma genitalium* | MG050 | 1045723 | 3NGJ Identity 40% |
| MTH0818 | *Methanothermobacter thermautotrophicus* | MTH0818 | 2621909 | 3R13 Identity 55% |
| PS0950 | *Pseudomonas syringae* tomato DC3000 | deoC | 28868193 | 1P1X Identity 38% |
| PSPH0865 | *Pseudomonas syringae* phaseolicola 1448A | deoC | 71733380 | 1P1X Identity 37% |
| RHA07557 | *Rhodococcus* sp. RHA1 | na | 111019087 | 3NDO Identity 60% |
| SA0138 | *Staphylococcus aureus* | dra | 15923128 | 3NGJ Identity 53% |
| SA2137 | *Staphylococcus aureus* | na | 15925127 | 3NGJ Identity 52% |
| SAV3348 | *Streptomyces avermitilis* | deoC | 29829888 | 1KTN Identity 33% |
| SC4702 | *Streptomyces coelicolor* | na | 21223288 | 1 KTN Identity 33% |
| SF4413 | *Shigella flexneri* 2a | deoC | 56480609 | 1P1X Identity 99% |
| SM2560 | *Sinorhizobium meliloti* | na | 15966313 | 3NGJ Identity 31% |
| SM5503 | *Sinorhizobium meliloti* | deoC | 16264552 | 1KTN Identity 31% |
| SO1217 | *Shewanella oneidensis* | deoC | 24372798 | 1P1X Identity 63% |
| SP0843 | *Streptococcus pneumoniae* TIGR4 | na | 15900730 | 3NGJ Identity 59% |
| SPA4381 | *Salmonella enterica*Paratypi ATCC9150 | deoC | 56416341 | 1P1X Identity 94% |
| TA0684 | *Thermoplasma acidophilum* | TA0684 | 10639970 | 1VCV Identity 37% |
| TM1559 | *Thermotoga maritima* | TM1559 | 4982126 | 3R13 Identity 100% |
| TSTM4263 | *Salmonella typhimurium* LT2 | deoC | 16767808 | 1P1X Identity 94% |
| TTC0823 | *Thermus thermophilus* HB27 | na | 46199129 | 1UB3 Identity 98% |

To further narrow down the list of potential aldolase enzymes from the 34 enzymes, aldolase from *T. maritima* (TM1559) that was previously shown to exhibit higher aldol condensation activity towards acetaldehyde relative to *E. coli* DERA was chosen. TM1559 thus represented a potentially better DERA than *E. coli*'s. As such, TM1559 was used as a basis to screen for the potential DERAs that had not been previously characterized but that could exhibit higher acetaldehyde aldol condensation activity.

Our further analysis of the crystal structure of DERA from *T. maritima* [Heine, A., Luz, J. G., Wong, C.-H. & Wilson, I. a Analysis of the class I aldolase binding site architecture based on the crystal structure of 2-deoxyribose-5-phosphate aldolase at 0.99 A resolution. *Journal of molecular biology* 343, 1019-34 (2004)] and multiple sequence alignment analysis, revealed interesting residues in the phosphate binding pocket of TM1559 that could have a role to play in aldol condensation activity towards acetaldehyde. These residues were conserved in a few of the DERA enzymes from the 34 remaining enzymes but not in *E. coli* DERA. These residues

TABLE 9

| Internal reference ID | Organism | GI | Expressed and Purified | Stock concentration [mg/mL] |
|---|---|---|---|---|
| APE2437 | *Aeropyrum pernix* | 5106141 | No | n.a. |
| BCE1975 | *Bacillus cereus* ATCC 10987 | 42781044 | Yes | 4.03 |
| BH1352 | *Bacillus halodurans* | 15613915 | Yes | 3.53 |
| BSU3938 | *Bacillus subtilis* | 225185466 | Yes | 1.92 |
| DRD1181 | *Deinococcus radiodurans* | 6458945 | Yes | 5.15 |
| EC1535 | *Escherichia coli* K12 | 16132198 | Yes | 4.1 |
| HL1382 | *Halobacterium* sp. | 15790758 | No | n.a. |
| LB1413 | *Lactobacillus brevis* | na | No | n.a. |
| LMO1995 | *Listeria monocytogenes* | 16804034 | Yes | 3.06 |
| MTH0818 | *Methanothermobacter thermautotrophicus* | 2621909 | Yes | 3.22 |
| SA0138 | *Staphylococcus aureus* | 15923128 | No | n.a. |
| SA2137 | *Staphylococcus aureus* | 15925127 | Yes | 1.97 |
| SP0843 | *Streptococcus pneumoniae* TIGR4 | 15900730 | Yes | 3.53 |

TABLE 9-continued

| Internal reference ID | Organism | GI | Expressed and Purified | Stock concentration [mg/mL] |
|---|---|---|---|---|
| TA0684 | Thermoplasma acidophilum | 10639970 | No | n.a. |
| TM1559 | Thermotoga maritima | 4982126 | Yes | 10.38 |

Example 2: Characterization of DERA Enzymes for Acetaldehyde Aldol Condensation by In Vitro Assay DERA from fifteen species, the thirteen candidates along with DERAs from *T. maritima* and *E. coli*, were each expressed in a host organism, and ten were successfully purified (TABLE 9).

The ten purified DERA enzymes were screened for their activity against acetaldehyde aldol condensation using an enzymatic assay as previously described [Chen, L., Dumas, D. P. & Wong, C. Deoxyribose-5-phosphate Aldolase as a Catalyst in Asymmetric Aldol Condensation. *Journal of the American Chemical Society* 114, 741-748 (1992)]. Briefly, each enzyme was allowed to react with acetaldehyde for five hours. A 20 µL aliquot from each reaction was taken and placed on ice. Then 2.5 µL of the sample was diluted 20 times in water. To assay the amount of acetaldehyde remaining in the reaction, 6 µL of the diluted sample was added to a mixture containing 0.3 mM NADH, 1 mg of yeast alcohol dehydrogenase, in 100 mM triethanolamine buffer (TEA) at pH 7.5 in 96-well plates such that each well contained a final volume of 200 µL. The absorbance of NADH ($\epsilon_{340\,nm}$=6220 $M^{-1} \cdot cm^{-1}$) was monitored at 340 nm using a plate reader where the decrease in absorbance due to NADH consumption was directly proportional to the amount of acetaldehyde remaining in each reaction. As such, the amount of acetaldehyde consumed in each reaction was the difference between the initial amount of acetaldehyde used in each aldol reaction and the amount of NADH consumed in the enzyme assay. The specific activity was determined from the amount of acetaldehyde consumed over 5 hours in a reaction mixture containing 0.8 mg of each enzyme.

Figure 8:
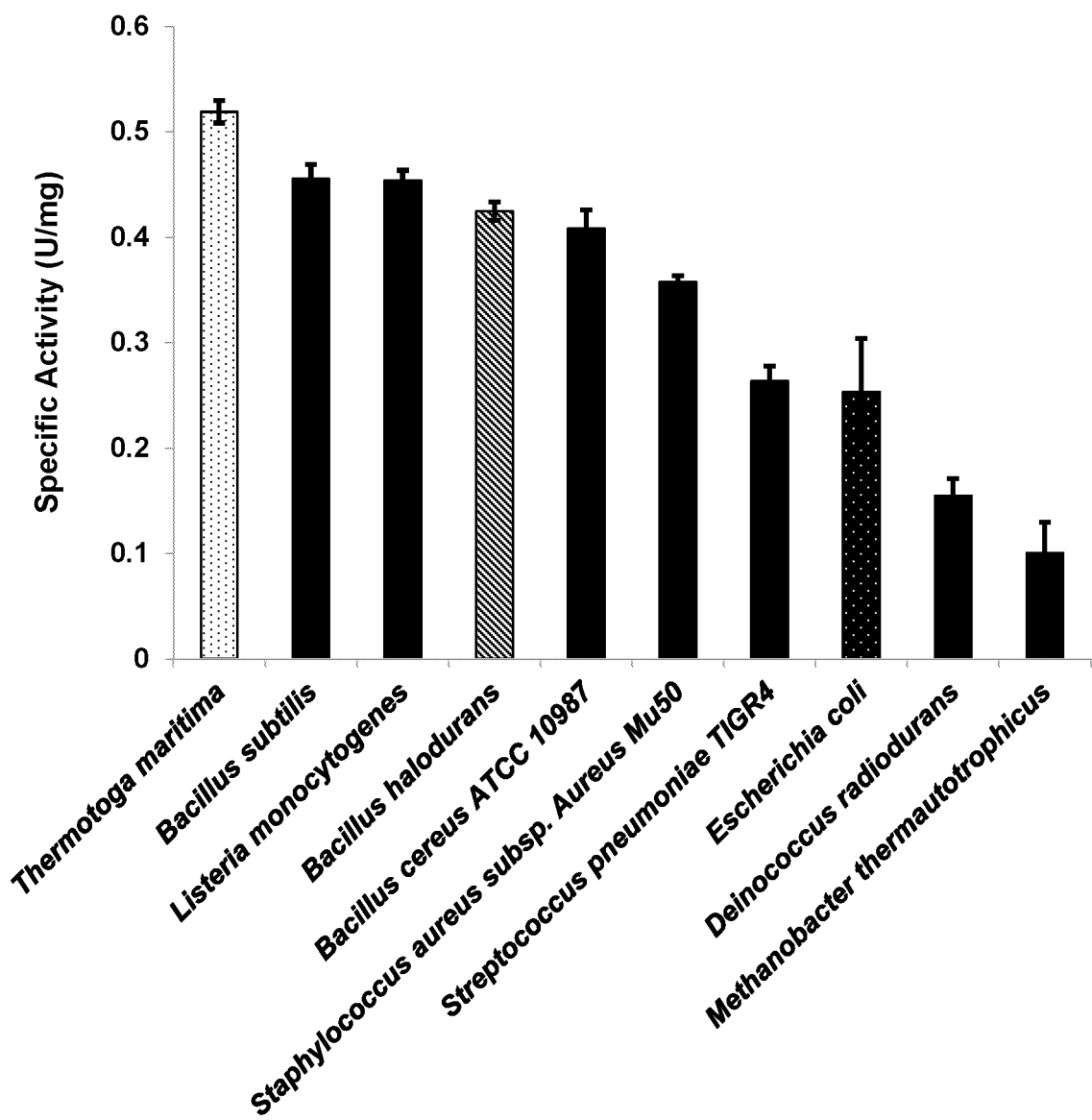
FIG. 8 schematically shows the results from screening ten aldolases, each from a different species, for acetaldehyde aldol condensation. The specific activity was determined from the change in acetaldehyde condensation over 5 hours in a reaction mixture containing 0.8 mg of each enzyme. The screened aldolases include DERA from *E. coli* (EC1535), from *Bacillus cereus* (BCE1975), *Bacillus halodurans* (BH1352), and *Bacillus subtilis* (BSU3938).

The results of the assay are shown in FIG. 8. All 10 enzymes exhibited some activity towards acetaldehyde aldol condensation. DERA from *T. maritima* appears to exhibit the highest activity followed by DERA from six organisms that exhibit higher activity than *E. coli* DERA. These six organisms share strictly conserved residues to TM1559: N21K, Y49N, K172F, N176G, except have A71C instead of A71V (where the first letter and number refer to the residue and its location in EC1535, and the final letter refers to the corresponding residue in TM1559).

Example 3: Identification of the Product from Acetaldehyde Condensation Using DERA In order to identify the product formed from the aldol condensation of acetaldehyde by DERA tested in Example 2, the enzymatic reaction mixture was prepared again in a larger volume and analyzed by high performance liquid chromatography (HPLC).

Briefly, a 6 mL reaction mixture was prepared by adding 20 mM of acetaldehyde and 600 mg of *B. halodurans* DERA in 100 mM triethanolamine buffer at pH 7.5. In parallel, a negative control was prepared similarly to the reaction but acetaldehyde was omitted. The two mixtures were incubated at room temperature. A 500 µL sample was taken from each, every five minutes for one hour. An aliquot of 200 µL of concentrated sulfuric acid was added to each sample to quench the reaction and placed on ice. The samples were then analyzed by HPLC on a Dionex Ultimate 3000 system equipped with a refractive index detector. An HPX-87H column was used to separate the analytes, acetaldehyde and 3HB with the following method: 30° C., 5 mM $H_2SO_4$, 0.8 mL/min, 20 min runtime. The peaks were identified using an RI-detector. The standard of 3-HB eluted at 11.8 min, and acetaldehyde standard at 13.5 min. The enzymes tested using HPLC included those from *B. halodurans* (BH1352), and *E. coli* (EC1535) (results not shown). The reactions using either enzyme resulted in acetaldehyde consumption and synthesis of 3HB. The cocentrations of acetaldehyde and 3HB are summarized in TABLE 10 below:

TABLE 10

| | acetaldehyde concentration | | 3HB concentration | |
|---|---|---|---|---|
| | Time = 0 min | Time = 60 mins | Time = 0 mins | Time = 60 mins |
| Control | 20.07 mM | 19.64 mM | 0 | 0 |
| Sample | 20.56 mM | 16.83 mM | 0.05 mM | 2.12 mM |

Example 4: Selection of Aldo-Ketoreductase Enzyme for 1,3-butanediol Pathways

The second step in the biosynthetic pathway to produce 1,3-butanediol (1,3-BDO) taught herein involves reducing 3HB to 1,3-BDO using an aldo-ketoreductase. Screening of the enzymes required for this reaction was carried out by screening 37 putative candidate aldo-keto reductases (TABLE 11). Substrate specificity on acetaldehyde and 3HB under relaxed conditions was measured spectrophotometrically in 96-well plates at 37° C. for 30 min in a reaction mixture containing $K_2HPO_4$ (50 mM, pH 7.0), KCl (10 mM), EDTA (0.5 mM), NADPH (1 mM), acetaldehyde and 3-hydroxybutanal as substrates (1 mM) and protein (20 µg) in a final volume of 200 µl. Reactions were monitored by following the decrease in absorbance at 340 nm as a measure of the conversion of the co-factor NADPH ($\epsilon_{340\,nm}$=6220 $M^{-1} \cdot cm^{-1}$) to $NADP^+$.

TABLE 11

| Target | Genome | GI | Activity on 3-hydroxybutanal (nmol/10 min) | Activity on acetaldehyde (nmol/10 min) |
|---|---|---|---|---|
| ATC2766 | Agrobacterium tumefaciens C58 | 17936691 | 0.5 | |
| ATC5198 | Agrobacterium tumefaciens C58 | 17938783 | 0.1 | |
| BCE0216 | Bacillus cereus ATCC 10987 | 42779297 | 2.2 | |
| BCE2100 | Bacillus cereus ATCC 10987 | 42781166 | 0.2 | |
| BCE4166 | Bacillus cereus ATCC 10987 | 42783212 | 1.2 | |

TABLE 11-continued

| Target | Genome | GI | Activity on 3-hydroxybutanal (nmol/10 min) | Activity on acetaldehyde (nmol/10 min) |
|---|---|---|---|---|
| BCE5206 | Bacillus cereus ATCC 10987 | 42784252 | 2.3 | |
| BH2158 | Bacillus halodurans | 15614721 | 2.7 | |
| BH3849 | Bacillus halodurans | 15616411 | 5.1 | 0.7 |
| BH3927 | Bacillus halodurans | 15616489 | 0.5 | |
| BSU0278 | Bacillus subtilis | 2632563 | 0.1 | |
| BSU0415 | Bacillus subtilis | 2632715 | 0.2 | |
| BSU0953 | Bacillus subtilis | 2633288 | 6.6 | 0.2 |
| BSU2901 | Bacillus subtilis | 2635370 | 1.7 | |
| BSU3337 | Bacillus subtilis | 2635853 | 3.1 | |
| BSU3974 | Bacillus subtilis | 2636524 | −0.3 | |
| HP1173 | Helicobacter pylori | 15645807 | −1.6 | |
| LB0084 | Lactobacillus brevis | na | 5.7 | 1.0 |
| LB0246 | Lactobacillus brevis | na | 5.0 | 1.0 |
| LB0352 | Lactobacillus brevis | na | 0.5 | |
| LB0782 | Lactobacillus brevis | na | 1.0 | |
| LB1055 | Lactobacillus brevis | na | 0.8 | |
| LB1274 | Lactobacillus brevis | na | 0.5 | |
| LB1646 | Lactobacillus brevis | na | 0.9 | |
| LB1760 | Lactobacillus brevis | na | 0.2 | |
| LB1888 | Lactobacillus brevis | na | 0.3 | |
| PA1127 | Pseudomonas aeruginosa | 15596324 | 10.7 | 0.4 |
| PA2535 | Pseudomonas aeruginosa | 15597731 | 0.2 | |
| PA3795 | Pseudomonas aeruginosa | 15598990 | 0.4 | |
| PP3637 | Pseudomonas putida KT2440 | 26990382 | 0.6 | |
| PS0338 | Pseudomonas syringae tomato DC3000 | 28867581 | 3.0 | |
| PS3111 | Pseudomonas syringae tomato DC3000 | 28870354 | 0.1 | |
| PS3612 | Pseudomonas syringae tomato DC3000 | 28870855 | 1.2 | |
| PS5316 | Pseudomonas syringae tomato DC3000 | 28872559 | −0.5 | |
| RP2139 | Rhodopseudomonas palustris CGA009 | 39935219 | 2.1 | |
| TSTM2268 | Salmonella typhimurium LT2 | 16765732 | 1.7 | |
| YST4865 | Saccharomyces cerevisiae | 6322556 | 0.4 | |
| YST7394 | Saccharomyces cerevisiae | 6325384 | 0.5 | |

A candidate reductase from *Pseudomonas aeroginosa* (PA1127) was chosen because it showed significant activity against 3HB but no activity against acetaldehyde.

The product of the PA1127 reductase-catalyzed reaction was identified using HPLC according to the following method: HPX-87H column, 60° C., 0.4 mL/min, and 5 mM $H_2SO_4$. The peaks were detected using an RI detector. The following standards were first ran: 1,3-BDO eluted at 28.46 min, acetaldehyde at 27.46 min, and 3HB at 23.35 min. A reaction mixture was prepared by mixing 55 mM of 3HB, also containing about 38 mM of acetaldehyde, and the reductase enzyme 60 mg of PA1127 in 100 mM TEA buffer at pH 7.5. At various time points, an aliquot of the reaction mixture was analyzed using HPLC. In presence of the enzyme PA1127, 3HB was consumed over time with a simultaneous increase in 1,3-BDO concentration, while acetaldehyde concentration remained constant. No conversion of 3HB to 1,3-BDO was detected in the negative control (TABLE 12), thus verifying the specificity of PA1127 towards 3HB.

Example 5: In Vitro Validation of 1,3-BDO Pathway

In order to test the activity of the aldolase and reductase enzymes together, a coupled enzyme reaction was performed using the following method: DERA from *B. halodurans* and reductase from *P. aeroginosa* were tested in a 0.6 mL reaction mixture containing 25 mM acetaldehyde, 60 mg of DERA, 60 mg of reductase, and 20 mM of NADPH in 100 mM TEA buffer at pH 7.5. At various time points, aliquots of each reaction mixture were analyzed using HPLC similarly to the method described in Example 4. The results are summarized in TABLE 13.

Acetaldehyde concentration decreased over time with a simultaneous increase in 1,3-BDO. No reaction products, either 3HB or 1,3-BDO, were identified in the negative control without enzymes. Due to the high volatility of acetaldehyde, some was lost during the reaction. The remaining reacted acetaldehyde may have been converted to the double, sequential aldol condensation product (2,4,6-trideoxy-D-erythro-hexapyranoside), which could not be identified by HPLC due to the lack of available standard for verification.

TABLE 12

| | acetaldehyde concentration | | 3HB concentration | | 1,3-BDO concentration | |
|---|---|---|---|---|---|---|
| | t = 0 min | t = 190 mins | t = 0 min | t = 190 mins | t = 0 mins | t = 190 mins |
| Control | 38.51 mM | 38.05 mM | 58.40 mM | 60.16 mM | 0 | 0 |
| Sample | 36.92 mM | 36.29 mM | 54.49 mM | 28.25 mM | 0.85 mM | 20.43 mM |

TABLE 13

| | acetaldehyde concentration | | 1,3-BDO concentration | |
|---|---|---|---|---|
| | t = 0 min | t = 150 mins | t = 0 mins | t = 150 mins |
| Control | 40.42 mM | 38.20 mM | 0 | 0 |
| Sample | 38.14 mM | 25.18 mM | 0 | 3.27 mM |

Example 6: In Vivo Validation of 1,3-BDO Pathway in Wild Type *E. coli*

The vector backbone used for the expression of the 1,3-BDO pathway genes was pTrc99a with inducible lacI promoter and with ampicillin resistance. Three genes, required for expression of PDC, DERA, and AKR, were assembled into the expression vector. Each DNA part was flanked with unique nucleotide sequences (UNS) [Orella, J. P., Lienert, F., Boehm, C. R., Chen, J.-H., Way, J. C., & Silver, P. a. (2014). Unique nucleotide sequence-guided assembly of repetitive DNA parts for synthetic biology applications. Nature Protocols, 9(9), 2075-89]. The primers used to amplify each part is listed in TABLE 14. The DNA parts were then assembled by ligasae cycling reaction (LCR) as described in [Kok, S. De, Stanton, L. H., Slaby, T., Durot, M., Holmes, V. F., Patel, K. G., Chandran, S. S. (2014). Rapid and Reliable DNA Assembly via Ligase Cycling Reaction. ACS, 3, 97-106] using ssDNA bridging oligos that have a 5' homologous region to the 3' UNS of one part, and a 3' homologous region to the 5; UNS of the consecutive DNA part. Briefly, the DNA parts were first amplified by PCR using Q5© high-fidelity DNA polymerase (New England Biolabs) following manufacturer's protocol. The PCR products were then digested with DpnI to digest the template plasmid by adding 1 μL of DpnI enzyme to each 50 μL reaction mixture and incubating at 37° C. for 1 hour, then at 85° C. for 20 min. The PCR product were then purified using a PCR purification kit purchased from Thermo Scientific and performed according to manufacturer's protocol. After purification, the DNA parts were phosphorylated using T4 polynucleotide kinase (PNK) (New England Biolabs). (Alternatively, one can order phosphorylated primers to avoid this step). Briefly, a 20 μL phosphorylation reaction was prepared containing 10 U of T4 PNK, 100 fmol of each purified DNA part, 5 mM ATP, in ampligase thermostable reaction buffer diluted to 1× in water. The reaction mixture was incubated at 37° C. for 1 hour then at 65° C. for 20 min. Following phosphorylation, a 25 μL of ligase cycling reaction mixture was prepared by adding 15 μL of phosphorylation mixture, 1 μL of ampligase thermostable reaction buffer, 30 nM of each oligo bridge, 8% v/v DMSO, 0.45M betaine, 0.3 U/μL of Ampligase thermostable DNA ligase, diluted in water to make up 25 μL. The following temperature cycle was used: 2 min at 94° C., 50 cycles of: 10 s at 94° C., 30 s at 55° C., 60 s at 66° C., then 4° C. forever. Transformation of 50 μL chemically competent (alternatively, electrocompetent cells may also be used) *E. coli* DH10β cells was performed with 5 uL of LCR mix. Colonies were then screened for correct plasmid by PCR, restriction digest, and/or sequencing. The plasmid was designated as pBD3. The constructed plasmid was introduced into the wild type *E. coli* MG1655. The resulting strain was designated as ecBD-6.

The ecBD-6 strain was characterized in triplicates by two-phase, fed-batch fermentation. The seed cultures were prepared by inoculating 5 mL of LB (supplemented with 100 μg/mL carbencillin) with a single colony then grown over night at 37° C. on a rotary shaker set to 250 rpm. Then 50 mL of TB supplemented with 100 μg/mL of carbenicillin was inoculated with the overnight culture and grown aerobically at 30° C. until the optical density at 600 nm reached 0.6. Protein expression was then induced with 1 mM IPTG. After five hours of protein expression, the cells were pelleted and re-suspended in 25 mL of minimal salts media (M9 salts media) containing 3% (w/v) glucose at a high cell density. The fermentation was carried out in sealed 250 mL baffled flasks at 37° C. Glucose was fed again at a concentration of 15 g/L at 20 and 50 hours from the start of fermentation. At various time points, samples were taken to determine the cell optical density at 600 nm. The concentration of substrate and products were determined by HPLC analysis using Dionex Ultimate-3000 HPLC system equipped with UV and refractive index detectors. The column used was Aminex HPX-87H with 5 mM $H_2SO_4$ as the eluent and operated at 36° C. After 93 hours of fermentation, ecBD-6 produced 1.42 g/L of 1,3-butanediol.

TABLE 14 shows primers used for assembly of plasmid pBD3 expressing the 1,3-BDO pathway genes, including PDC from *Zymomonas mobilis*, DERA from *Bacillus halodurans*, and AKR from *Pseudomonas aeruginosa*. The vector backbone, pTRC99a was also amplified with primers containing UNS. The four DNA parts were then assembled by ligase cycling reaction.

TABLE 14

| Primer name | Sequence ID |
|---|---|
| F-pTrc-UNS8 | 29 |
| R-pTrc-UNS1 | 30 |
| F-BH1352-UNS2 | 31 |
| R-DERA-UNS3 | 32 |
| F-PA1127-UNS4 | 33 |
| R-PA1127-UNS5 | 34 |
| F-PDC-UNS6 | 35 |
| R-PDC-UNS7 | 36 |

Example 7: Construction of Pyruvate-Accumulating Strain

As pyruvate is the first metabolite in the 1,3-butanediol pathway, increasing 1,3-butanediol production requires a host organism that can accumulate pyruvate. The latter represents a key metabolite in the central carbon metabolism of most common microorganisms. In *E. coli*, pyruvate is the main precursor to several native fermentative by-products (FIG. 2). To produce high titres of pyruvate in *E. coli*, pathways draining pyruvate to fermentative products were deleted. Accordingly, three genes, adhE (encoding alcohol dehydrogenase), IdhA (encoding lactate dehydrogenase), and pflB (encoding pyruvate formate lyase), were deleted from *E. coli* to eliminate formation of ethanol, lactate, and formate, respectively FIG. 2). The gene deletions were sequentially transferred from the corresponding single gene deletion mutants from KEIO collection to the wild type strain using P1 transduction method. The gene deletions were confirmed using PCR using the primers provided in the sequence listing: F-adhE-check and R-adhE-check (Sequence ID 37 and 38), F-IdhA-check and R-IdhA-check (Sequence ID 39 and 40), F-pflB-check and R-pflA-check (Sequence ID 41 and 42). The resultant strain with three gene deletions was designated as LMSE-25.

The strain LMSE-25 was characterized on mineral medium containing 15 g/L glucose, 3.5 g/L of $(NH_4)_2HPO_4$, 5 g/L of $K_2HPO_4$, and 3.5 g/L of $KH_2PO_4$, 0.25 g of $MgSO_4.7H_2O$, 15 mg $CaCl_2.2H_2O$, 0.5 mg of thiamine, and 1 ml of trace metal stock. The trace metal stock was prepared in 0.1 M HCl and consisted of per liter: 1.6 g of $FeCl_3$, 0.2 g of $CoCl_2.6H_2O$, 0.1 g of $CuCl_2$, 0.2 g of $ZnCl_2.4H_2O$, 0.2 g of $NaMoO_4$, and 0.05 g of $H_3BO_3$ (Causey, T. B., Zhou, S., Shanmugam, K. T. & Ingram, L. O. (2003) Proc. Natl. Acad. Sci. USA100, 825-832). The characterization was carried out in 500 ml fermenters with pH controlled at 7.0 using 4 M KOH and air sparging for dissolved oxygen control (>70%).

The control wild-type *E. coli* did not accumulate detectable amount of pyruvate, whereas the mutant strain produced a maximum titer of 0.67 g/L in 5 hours representing a 20% of the maximum theoretical yield from glucose.

Example 8: Construction of Strain ecBD-5

The strain ecBD-5 was constructed by introducing the plasmid pBD3 in the pyruvate producing strain LMSE-25. The 1,3-butanediol-producing *E. coli* strain (ecBD-5) thus produced was characterized by fed-batch fermentation using glucose as the carbon source and performed under semi-aerobic conditions. The strain was first cultivated at 30° C. in 50 mL of rich medium (Terrific Broth) in 250 mL baffled flasks to express the pathway proteins. After five hours of protein expression, the cells were pelleted and re-suspended in 25 mL of minimal salts media (M9 salts media) containing 3% (w/v) glucose at a high cell density. The fermentation was carried out in sealed 250 mL baffled flasks at 37° C. Glucose was fed again at a concentration of 15 g/L at 20 and 50 hours from the start of fermentation. This experiment was performed in triplicates.

At various time points, samples were taken to determine the cell optical density at 600 nm. The concentration of substrate and products were determined by HPLC analysis using Dionex Ultimate-3000 HPLC system equipped with UV and refractive index detectors. The column used was Aminex HPX-87H with 5 mM $H_2SO_4$ as the eluent and operated at 36° C.

After 93 hours of fermentation, ecBD-5 produced 2.1 g/L of 1,3-BDO, whereas the control ecBD-6 produced 1.42 g/L of 1,3-BDO.

What is claimed is:

1. A method for producing 1,3-butanediol (1,3-BDO), the method comprising:
   (a) providing recombinant bacteria engineered to produce 1,3-BDO from (i) condensation of two acetaldehydes to produce 3-hydroxybutanal, and (ii) reduction of the 3-hydroxybutanal to 1,3-BDO, the recombinant bacteria being engineered to express at least one exogenous nucleic acid encoding a deoxyribose-5-phosphate aldolase (DERA) comprising an amino acid sequence at least 90% identical to the amino acid sequence of SEQ ID NO: 22 that catalyzes reaction (i), and to express at least one further exogenous nucleic acid encoding an aldo-keto reductase (AKR) comprising an amino acid sequence at least 90% identical to the amino acid sequence of SEQ ID NO: 25 that catalyzes reaction (ii); and
   (b) culturing the recombinant bacteria under conditions and for a sufficient period of time to produce 1,3-BDO.

2. The method of claim 1, wherein said DERA comprises residues D102, K167, and K201, with respect to the amino acid numbering of the *E. coli* DERA of SEQ ID NO: 20.

3. The method of claim 2, wherein said DERA further comprises residue D16, with respect to the amino acid numbering of the *E. coli* DERA of SEQ ID NO: 20.

4. The method of claim 1, wherein said DERA comprises residues K21, N49, C71 or V71, F172, and H176 or G176, with respect to the amino acid numbering of the *E. coli* DERA of SEQ ID NO: 20.

5. The method of claim 4, wherein said DERA comprises residues D102, K167, and K201, with respect to the amino acid numbering of the *E. coli* DERA of SEQ ID NO: 20.

6. The method of claim 5, wherein said DERA further comprises residue D16, with respect to the amino acid numbering of the *E. coli* DERA of SEQ ID NO: 20.

7. The method of claim 1, wherein said DERA comprises an amino acid sequence at least 95% identical to the amino acid sequence of SEQ ID NO: 22.

8. The method of claim 1, wherein the recombinant bacteria is engineered to express at least one further exogenous nucleic acid encoding an oxidoreductase, aldehyde reductase, or alcohol dehydrogenase.

9. The method of claim 1, wherein said AKR comprises the residues R214, R227, R281, Q285, G279, and R208, with respect to the amino acid numbering of SEQ ID NO: 25.

10. The method of claim 1, wherein said AKR comprises an amino acid sequence at least 95% identical to the amino acid sequence of SEQ ID NO: 25.

11. The method of claim 1, wherein the recombinant bacteria is further engineered to express at least one further exogenous nucleic acid encoding a decarboxylase that catalyzes the decarboxylation of pyruvate to yield acetaldehyde and carbon dioxide.

12. The method of claim 11, wherein the decarboxylase is pyruvate decarboxylase (PDC), benzoylformate decarboxylase (BFD), or alpha-ketoacid decarboxylase (KDC).

13. The method of claim 12, wherein the PDC comprises an amino acid sequence at least 90% identical to SEQ ID NO: 26, the BFD comprises an amino acid sequence at least 90% identical to SEQ ID NO: 27, or the KDC comprises an amino acid sequence at least 90% identical to SEQ ID NO: 28.

14. The method of claim 1, wherein the recombinant bacteria is further genetically modified to delete or disrupt an enzyme that utilizes pyruvate, as compared to a corresponding non-recombinant bacteria.

15. The method of claim 1, wherein the recombinant bacteria is further engineered to increase acetaldehyde production, as compared to a corresponding non-recombinant bacteria.

16. The method of claim 1, wherein the recombinant bacteria produces enantiopure (R)-1,3-BDO.

17. A method for producing 1,3-butanediol (1,3-BDO), the method comprising:
   (a) providing recombinant bacteria engineered to produce 1,3-BDO from (i) condensation of two acetaldehydes to produce 3-hydroxybutanal, and (ii) reduction of the 3-hydroxybutanal to 1,3-BDO, the recombinant bacteria being engineered to express at least one exogenous nucleic acid encoding a deoxyribose-5-phosphate aldolase (DERA) that catalyzes reaction (i), and to express at least one further exogenous nucleic acid encoding an aldo-keto reductase (AKR) that catalyzes reaction (ii); and
   (b) culturing the recombinant bacteria under conditions and for a sufficient period of time to produce 1,3-BDO,
   wherein said DERA comprises an amino acid sequence at least 90% identical to the amino acid sequence of SEQ ID NO: 22 and comprises residues K21, N49, C71 or V71, F172, and H176 or G176, with respect to the amino acid numbering of the *E. coli* DERA of SEQ ID NO: 20; and
   wherein said AKR comprises an amino acid sequence at least 90% identical to the amino acid sequence of SEQ ID NO: 25.

18. The method of claim 17, wherein said DERA further comprises residues D102, K167, and K201, with respect to the amino acid numbering of the *E. coli* DERA of SEQ ID NO: 20.

19. The method of claim 18, wherein said DERA further comprises residue D16, with respect to the amino acid numbering of the *E. coli* DERA of SEQ ID NO: 20.

20. A method for producing 1,3-butanediol (1,3-BDO), the method comprising:
   (a) providing recombinant bacteria engineered to produce 1,3-BDO from (i) condensation of two acetaldehydes to produce 3-hydroxybutanal, and (ii) reduction of the 3-hydroxybutanal to 1,3-BDO, the recombinant bacteria being engineered to express at least one exogenous nucleic acid encoding a deoxyribose-5-phosphate aldolase (DERA) that catalyzes reaction (i), and to express at least one further exogenous nucleic acid encoding an aldo-keto reductase (AKR) that catalyzes reaction (ii); and (b) culturing the recombinant bacteria under conditions and for a sufficient period of time to produce 1,3-BDO, wherein said DERA is a variant of a *Bacillus halodurans* DERA, said *Bacillus halodurans* DERA comprising an amino acid sequence at least 95% identical to the amino acid sequence of SEQ ID NO: 22; and wherein said AKR is a variant of a *Pseudomonas aeruginosa* AKR, said *Pseudomonas aeruginosa* AKR comprising an amino acid sequence at least 95% identical to the amino acid sequence of SEQ ID NO: 25.

21. The method of claim 20, wherein said DERA comprises residues K21, N49, C71 or V71, F172, and H176 or G176, with respect to the amino acid numbering of the aldolase of SEQ ID NO: 20.

22. The method of claim 20, wherein said DERA comprises residues D102, K167, and K201, with respect to the amino acid numbering of the *E. coli* DERA of SEQ ID NO: 20.

23. The method of claim 22, wherein said DERA further comprises residue D16, with respect to the amino acid numbering of the *E. coli* DERA of SEQ ID NO: 20.

* * * * *

```
                       SEQUENCE LISTING

<160> NUMBER OF SEQ ID NOS: 59

<210> SEQ ID NO 1
<211> LENGTH: 672
<212> TYPE: DNA
<213> ORGANISM: Bacillus cereus ATCC 10987
<300> PUBLICATION INFORMATION:
<308> DATABASE ACCESSION NUMBER: AE017194.1
<309> DATABASE ENTRY DATE: 2014-01-31
<313> RELEVANT RESIDUES IN SEQ ID NO: (1909205)..(1909876)

<400> SEQUENCE: 1
atgaacattg caaagttaat tgaccataca attttaaaag ctaatactac taaagaagat      60
gttatgaaag taatcgaaga agcaaaggaa tataaattcg cttctgtttg tattaatcct     120
acatgggtaa agctagctgc tgaggaatta gctggacatg atgtagatgt ttgtactgta     180
atcggtttcc cattaggcgc aagtactact gaaacaaaag cttttcgaaac aaaagatgct     240 atcgcaaaag gtgcaactga agttgacatg gtaatcaacg taggcgcttt aaaagatggc     300
gacgacgaac ttgttgaaaa agacatttat gaagtagtac aagcagcaaa aggaaaagct     360
cttgtaaaag taatcattga aacttgccta ttaacagatg aagagaaagt acgcgcttgt     420
gaattatcag taaaagctgg ggctgatttc gtaaaaactt caactggatt ctcaactggc     480
ggagcaactg ctgaagatat cgcattaatg cgtaaaacag ttggaccaaa cgttggtgta     540
aaagcatctg gtggcgttcg tacacgtgaa gatgcagaaa aatggtagc tgctggagct     600 tctcgcgttg gagcaagtgc tagtgttgca atcgtattaa atgatgcaaa aggtgctaca     660
gataactact aa                                                        672

<210> SEQ ID NO 2
<211> LENGTH: 780
<212> TYPE: DNA
<213> ORGANISM: Escherichia coli K12
<300> PUBLICATION INFORMATION:
<308> DATABASE ACCESSION NUMBER: CP009685
<309> DATABASE ENTRY DATE: 2014-12-15
<313> RELEVANT RESIDUES IN SEQ ID NO: (3719004)..(3719783)

<400> SEQUENCE: 2
atgactgatc tgaaagcaag cagcctgcgt gcactgaaat tgatggacct gaccaccctg      60
```

| | | |
|---|---|---|
| aatgacgacg acaccgacga gaaagtgatc gccctgtgtc atcaggccaa aactccggtc | 120 |
| ggcaataccg ccgctatctg tatctatcct cgctttatcc cgattgctcg caaaactctg | 180 |
| aaagagcagg gcaccccgga atccgtatc gctacggtaa ccaacttccc acacggtaac | 240 |
| gacgacatcg acatcgcgct ggcagaaacc cgtgcggcaa tcgcctacgg tgctgatgaa | 300 |
| gttgacgttg tgttcccgta ccgcgcgctg atggcgggta acgagcaggt tggttttgac | 360 |
| ctggtgaaag cctgtaaaga ggcttgcgcg cagcgaatg tactgctgaa agtgatcatc | 420 |
| gaaaccggcg aactgaaaga cgaagcgctg atccgtaaag cgtctgaaat ctccatcaaa | 480 |
| gcgggtgcgg acttcatcaa aacctctacc ggtaaagtgg ctgtgaacgc gacgccggaa | 540 |
| agcgcgcgca tcatgatgga agtgatccgt gatatgggcg tagaaaaaac cgttggtttc | 600 |
| aaaccggcgg gcggcgtgcg tactgcggaa gatgcgcaga aatatctcgc cattgcagat | 660 |
| gaactgttcg gtgctgactg ggcagatgcg cgtcactacc gctttggcgc ttccagcctg | 720 |
| ctggcaagcc tgctgaaagc gctgggtcac ggcgacggta gagcgccag cagctactaa | 780 |

<210> SEQ ID NO 3
<211> LENGTH: 675
<212> TYPE: DNA
<213> ORGANISM: Bacillus halodurans C-125
<300> PUBLICATION INFORMATION:
<308> DATABASE ACCESSION NUMBER: BA000004
<309> DATABASE ENTRY DATE: 2009-04-16
<313> RELEVANT RESIDUES IN SEQ ID NO: (1438985)..(1439659)

<400> SEQUENCE: 3

| | | |
|---|---|---|
| atgtcacgtt cgattgcaca atgattgat catacgctac ttaaaccaaa tacaacagaa | 60 |
| gaccaaattg taaagctctg tgaggaagca aggaatatt catttgcatc tgtttgtgtg | 120 |
| aatcctactt gggtcgctct tgctgcgcag ttgctaaaag atgcacctga tgtgaaagta | 180 |
| tgtacagtta tcggctttcc gttaggggca acgactccgg aagtgaaagc gtttgaaacg | 240 |
| actaatgcca ttgaaaatgg agcgacagaa gtggacatgg tcattaacat tggagcgtta | 300 |
| aaagataaac aatacgagct tgttggacgc gacattcaag cggttgttaa agcagcagaa | 360 |
| gggaaagcat taacgaaagt aatcattgaa acatcgttat taacggagga agagaagaag | 420 |
| gctgcgtgtg agcttgccgt aaaagcagga gccgactttg tcaaaacgtc gactggattc | 480 |
| tctggcggag gtgctacggc tgaggatatc gcgctcatgc gaaaagtggt cggaccaaat | 540 |
| ttaggagtca aagcttctgg aggtgttaga gatctgtccg acgcgaaagc gatgattgat | 600 |
| gctggtgcta ctcggattgg tgcgagtgct ggggtggcga ttgttaacgg ggagcgtagc | 660 |
| gaagggagtt attaa | 675 |

<210> SEQ ID NO 4
<211> LENGTH: 672
<212> TYPE: DNA
<213> ORGANISM: Bacillus subtilis subsp. subtilis str. 168
<300> PUBLICATION INFORMATION:
<308> DATABASE ACCESSION NUMBER: AL009126.3
<309> DATABASE ENTRY DATE: 2015-02-27
<313> RELEVANT RESIDUES IN SEQ ID NO: (4051602)..(4052273)

<400> SEQUENCE: 4

| | | |
|---|---|---|
| atgtcattag ccaacataat tgatcataca gctttgaaac cgcatacaca aaaagcggac | 60 |
| attctaaaac taattgaaga agcgaaaaca tacaaatttg cttcagtatg tgtcaatccg | 120 |
| acatgggtgg agcttgctgc aaaagagctt aagggaactg gagtcgacgt ttgtacggtc | 180 |

| | |
|---|---|
| atcggcttcc cgctcggtgc caatacaact gaaacaaaag cgttcgaaac aaaagacgcc | 240 |
| atttcaaaag cgccactgaa gtggatatg gtcattaata ttgccgcttt aaaagacaag | 300 |
| gaagacgatg tggtggaagc tgatatccgc ggtgtagtgg aagctgtagc cggaaaagcg | 360 |
| cttgtcaaag tcattatcga aacgtgcctt ctgactgatg aagaaaaaga acgtgcatgc | 420 |
| cgtttagcgg tgtctgcggg agcggatttc gtaaaaacat caacaggctt ttctacaggc | 480 |
| ggcgcaacga aggaagatat cgccttaatg cgcaaaacag tagggcctga tatcggcgtg | 540 |
| aaagcatctg gcggcgtcag aacgaaagaa gatgtagaca caatggtaga ggccggagca | 600 |
| agccgaattg gcgccagcgc aggcgtttct atcgtaaaag agaaaatgc atcaggcgga | 660 |
| gacaactatt aa | 672 |

<210> SEQ ID NO 5
<211> LENGTH: 747
<212> TYPE: DNA
<213> ORGANISM: Thermotoga maritima
<300> PUBLICATION INFORMATION:
<308> DATABASE ACCESSION NUMBER: CP011108
<309> DATABASE ENTRY DATE: 2015-04-24
<313> RELEVANT RESIDUES IN SEQ ID NO: (1550526)..(1551270)

<400> SEQUENCE: 5

| | |
|---|---|
| atgatagagt acaggattga ggaggcagta gcgaagtaca gagagttcta cgaattcaag | 60 |
| cccgtcagag aaagcgcagg tattgaagat gtgaaaagtg ctatagagca cacgaatctg | 120 |
| aaaccgtttg ccacaccaga cgatataaaa aaactctgtc ttgaagcaag ggaaaatcgt | 180 |
| ttccatggag tctgtgtgaa tccgtgttat gtgaaactgg ctcgtgaaga actcgaagga | 240 |
| accgatgtga aagtcgtcac cgttgttggt tttccactgg gagcgaacga aactcggacg | 300 |
| aaagcccatg aggcgatttt cgctgttgag agtggagccg atgagatcga tatggtcatc | 360 |
| aacgttggca tgctcaaggc aaaggagtgg gagtacgttt acgaggatat aagaagtgtt | 420 |
| gtcgaatcgg tgaaaggaaa agttgtgaag gtgatcatcg aaacgtgcta tctggatacg | 480 |
| gaagagaaga tagcggcgtg tgtcattcc aaacttgctg gagctcattt cgtgaagact | 540 |
| tccacgggat ttggaacagg aggggcgacc gcagaagacg ttcatctcat gaaatggatc | 600 |
| gtgggagatg agatgggtgt aaaagcttcc ggagggatca gaaccttcga ggacgctgtt | 660 |
| aaaatgatca tgtacggtgc tgatagaata ggaacgagtt cgggagttaa gatcgttcag | 720 |
| gggggagaag agagatatgg aggttaa | 747 |

<210> SEQ ID NO 6
<211> LENGTH: 675
<212> TYPE: DNA
<213> ORGANISM: Methanothermobacter thermautrophicus
<300> PUBLICATION INFORMATION:
<308> DATABASE ACCESSION NUMBER: AP011952
<309> DATABASE ENTRY DATE: 2015-03-03
<313> RELEVANT RESIDUES IN SEQ ID NO: (720590)..(721263)

<400> SEQUENCE: 6

| | |
|---|---|
| gtggttaaaa tgaatgtgga gacaagggag gaacttgcat cacttataga ccacaccaat | 60 |
| gtgagggctg atgcaacaga aaatgatatt gagaggctat gcaggaggc ggtcagctac | 120 |
| ggcttcaggt gcgcggtggt cacacccacc aatgtcaggc tggcggctga actccttgag | 180 |
| gggaccgatg tgacggtctg ctcagttgtt ggtttcccgg caggcgtcag tacaccccgc | 240 |
| gttaaggccc ttgaagcctc tgaggccgtt gagaacgggg ccggtgaggt ggacatggtc | 300 |
| atgaatatcg gggccatgaa gtcaggcaat agggagctcg tatacaggga tatcagcggc | 360 |

```
gttgttgatg ccgccggcgt ccccgtcaag gttatacttg aaacagccta tctcacagac    420
aaggagaagg ttgaagcctg ccttataagt aaagaggccg gtgcggcatt tgttaaaaca    480
tcaacagcct atggtggact agccggcgcc acagttgagg atgtgatgct catgcggaaa    540
acggtgggtg atgagatggg agtcaaggca tctgggggaa taaggatct tgaaacagcc     600 cttgcgatga tagatgctgg ggcagacagg atcgggacat caaccggtgt acagataatc    660
gagggatgga ggtaa                                                     675

<210> SEQ ID NO 7
<211> LENGTH: 663
<212> TYPE: DNA
<213> ORGANISM: Deinococcus radiodurans
<300> PUBLICATION INFORMATION:
<308> DATABASE ACCESSION NUMBER: AE000513
<309> DATABASE ENTRY DATE: 2014-01-31
<313> RELEVANT RESIDUES IN SEQ ID NO: (1215027)..(1215687)

<400> SEQUENCE: 7
atgtcactcg cctcctacat cgaccacacg ctgcttaagg ccaccgccac gctcgccgac     60
atccgcacgc tgtgtgagga agcccgcgag cactcgttct acgcggtgtg catcaacccg    120
gtctttattc cccacgcccg cgcctggctc gaaggcagcg acgtgaaggt cgccaccgtc    180
tgcggctttc ccctcggcgc catcagctcc gagcagaaag ctctggaagc ccgcctgagc    240
gccgaaacgg gcgccgacga aatcgatatg gtcatccaca tcggctcggc gcttgccggc    300
gactgggacg cggtggaagc cgacgtgcgg gcagtgcgcc gcgcggtgcc cgagcaggtg    360
ctcaaggtga ttatcgaaac ctgctacctg accgacgagc aaaagcgctt ggcgactgag    420
gtcgccgtac agggcggcgc cgacttcgtt aagacgagca caggcttcgg caccggcggc    480
gccaccgtgg acgacgtgcg cctgatggcg gaagtgatcg ggggccgcgc cggactcaag    540
gcggcgggcg gcgtccgcac tcctgccgac gcgcaagcca tgatcgaggc gggcgcgacc    600
cggctgggca cctcgggcgg cgtgggtctg gtgtcgggcg gcgaaaacgg agccggctac    660
taa                                                                  663

<210> SEQ ID NO 8
<211> LENGTH: 663
<212> TYPE: DNA
<213> ORGANISM: Staphylococcus aureus subsp. aureus Mu50
<300> PUBLICATION INFORMATION:
<308> DATABASE ACCESSION NUMBER: BA000017
<309> DATABASE ENTRY DATE: 2009-01-09
<313> RELEVANT RESIDUES IN SEQ ID NO: (2265358)..(2266020)

<400> SEQUENCE: 8
atgaatagtg caaaattgat tgatcacact ttattgaagc tgagtcaac acgtacgcaa      60 atcgatcaaa tcatcgatga agcgaaagca taccatttta atctgtatg tgtgaatcca     120 acgcatgtta aatatgcagc agagcgacta gctgattcag aggtgttagt ttgtacggta    180
ataggattcc cattaggtgc atcgacaact gcgacgaaag catttgaaac agaagatgcg    240
attcaaaatg gtgcagatga aattgacatg gtcatcaaca tcggcgcatt aaaagatgga    300
cgttttgatg atgtacaaca agacattgaa gcagtggtga agctgcgaa aggtcacaca    360 gtaaaagtga ttattgagac ggtattgttg gaccatgacg aaatcgtaaa agcgagtgaa    420
ttaacaaaag tggctggtgc ggacttcgtt aaaacttcaa caggttttgc aggtggcggt    480
gcgactgcag aagacgttaa attaatgaaa gatacagtag gtgctgatgt agaagtaaaa    540
```

```
gcatcaggtg gcgtacgtaa tttagaagat tcaataaaa tggttgaagc aggtgcgaca    600
cgtattggtg cgagcgcagg cgttcaaatt atgcaaggtt tagaagcaga ttcagattac    660
taa                                                                  663
```

<210> SEQ ID NO 9
<211> LENGTH: 672
<212> TYPE: DNA
<213> ORGANISM: Listeria monocytogenes EGD-e
<300> PUBLICATION INFORMATION:
<308> DATABASE ACCESSION NUMBER: HG421741
<309> DATABASE ENTRY DATE: 2015-02-27
<313> RELEVANT RESIDUES IN SEQ ID NO: (2068136)..(2068807)

<400> SEQUENCE: 9

```
atgacaattg ctaaaatgat cgatcatact gctttaaaac cagacacaac gaaagaacaa    60
attttaaccc taacaaaaga agcaagagaa tacggctttg catccgtatg tgtgaaccca    120
acttgggtaa aactatccgc tgaacaactt gctggagcag aatccgtagt atgtactgtt    180
atcggtttcc cactaggagc gaataccccct gaagtaaaag catttgaagt gaaagatgcc    240
atccaaaacg gcgcgaaaga agtcgatatg gttatcaata tcggtgcact taaagacaag    300
gacgacgaat tagtagaacg cgatattcgc gctgttgtcg atgttgctaa aggcaaagca    360
ttagtaaaag taattatcga aacttgccta ttaacagacg aagaaaaagt gcgcgcatgc    420
gaaatcgctg taaaagcagg aacagacttc gttaaaacat ctacaggatt ttcaacaggt    480
ggcgcaactg ccgaagatat cgccttgatg cgtaaaacag ttggaccgaa catcggtgta    540
aaagcatctg tgggggttcg tacgaaagaa gactagaaaa aatgatcga agcaggcgca    600 actcgtatcg gcgcaagtgc aggcgttgca attgtttccg gcgaaaaacc agctaaacct    660
gataattact aa                                                        672
```

<210> SEQ ID NO 10
<211> LENGTH: 663
<212> TYPE: DNA
<213> ORGANISM: Streptococcus pneumoniae TIGR4
<300> PUBLICATION INFORMATION:
<308> DATABASE ACCESSION NUMBER: AE005672
<309> DATABASE ENTRY DATE: 2014-01-31
<313> RELEVANT RESIDUES IN SEQ ID NO: (790292)..(790952)

<400> SEQUENCE: 10

```
atgaaattaa ataaatatat agatcatacg cttttaaaac aagatgcaaa gaaaaaacaa    60
attgatagtt tgttgtctga ggctagagag tatgactttg ccagtgtttg cgttaatccg    120 acctggggttg aacatgctaa aaaggacttg aaggcacag atgttaaggt ttgcacagta    180
gtaggtttcc ctttgggagc aacaacttca gccgtgaaag catttgagac aaaagaagct    240
atccaaaatg gtgcagatga gattgatatg gtgatcaatg ttggagctct caaatcaggt    300
aatttagcct tggttgagtc agatattcgc gcagtagtgg aagcaagtgg tgataagtta    360
gtgaaagtca ttattgaagc ttgccttctg acagaccaag aaaaagttgt tgtttgccaa    420
ttggcccaaa aagctggggc tgactttgtc aaaacatcta ctggcttttc aactggtggt    480
gctacgatag cagatgttac attaatgcgt gaaacagttg gatctgatat gggtgtcaag    540
gccgccggtg gagctcgttc ttatgcagat gctcttgcct ttgtcgaagc aggtgcgacc    600
cgtatcggaa cgtcagctgg ggtagctatt ttaaaaggag aattggcaga tggcgactac    660
taa                                                                  663
```

```
<210> SEQ ID NO 11
<211> LENGTH: 990
<212> TYPE: DNA
<213> ORGANISM: Pseudomonas aeruginosa
<300> PUBLICATION INFORMATION:
<308> DATABASE ACCESSION NUMBER: AE004091.2
<309> DATABASE ENTRY DATE: 2014-01-31
<313> RELEVANT RESIDUES IN SEQ ID NO: (1219623)..(1220610)

<400> SEQUENCE: 11
atgagcgttg aaagcattcg catcgagggt atcgacacgc cggtctcgcg catcggcctc      60
ggcacctggg ccatcggcgg ctggatgtgg ggcggcgctg acgacgcgac gtcggtggaa     120
accatccggc gtgcggtgga atccgggatc aacctgatcg acaccgcgcc ggtctatggc     180
ttcggccatt ccgaagaggt cgtcggcaag gccttgcagg gcctgcgcga caaggcggtg     240
atcgccacca aggcggcgct ggagtggagc acgcgggca tccaccgcaa cgcctccgcc      300
gcacgcatcc gccgggaggt cgaggactcg ctgcggcggc tgaagaccga tcgtatcgac     360
ctgtaccaga ttcactggcc ggacccgctg gtggcgcacg aggaaaccgc cggcgaactg     420
gagcgcctgc gccgcgacgg caagatcctc gccatcggcg tgagcaacta ttcgccggaa     480
cagatggacg ggttccgcca gttcgctccg ctggccagcg tgcagccacc ctacaacctg     540
ttcgagcgcg ccatcgacgc cgacgtgctg ccctacgccg agcgtaacgg catcgtcgtg     600
ctggcctacg agcgctgtg ccgcggcctg ctttccggac ggatgaacgc cgagacccgc     660
ttcgatggcg acgacctgcg caagtccgac ccgaagttcc agcagcccg cttcgcccag      720
tacctggcag cggtcgcgca actggaggaa ctggctcgcg agcgctatgg caagtcggtg     780
ctggccctgg ccatccgctg gattctcgat cgcggcccta cggtggcgct gtgggggcg      840
cgcaagccgg agcagttgaa cggcatcgcc gacgccttcg gctggcgcct ggacgacgag     900
gccatggccc gcatcgagcg gatcctcgcc gagaccatca aggatccggt cggtcccgag     960
ttcatggcgc cgcccagccg caacgcctaa                                      990

<210> SEQ ID NO 12
<211> LENGTH: 1707
<212> TYPE: DNA
<213> ORGANISM: Zymomonas mobilis
<300> PUBLICATION INFORMATION:
<308> DATABASE ACCESSION NUMBER: AE008692.2
<309> DATABASE ENTRY DATE: 2014-01-31
<313> RELEVANT RESIDUES IN SEQ ID NO: (1373366)..(1375072)

<400> SEQUENCE: 12
atgagttata ctgtcggtac ctatttagcg gagcggcttg tccagattgg tctcaagcat      60
cacttcgcag tcgcgggcga ctacaacctc gtccttcttg acaacctgct tttgaacaaa     120
aacatggagc aggtttattg ctgtaacgaa ctgaactgcg gtttcagtgc agaaggttat     180
gctcgtgcca aggcgcagc agcagccgtc gttacctaca gcgtcggtgc gctttccgca      240
tttgatgcta tcggtggcgc ctatgcagaa aaccttccgg ttatcctgat ctccggtgct     300
ccgaacaaca tgatcacgc tgctggtcac gtgttgcatc acgctcttgg caaaaccgac     360
tatcactatc agttggaaat ggccaagaac atcacggccg ccgctgaagc gatttacacc     420
ccggaagaag ctccggctaa aatcgatcac gtgattaaaa ctgctcttcg tgagaagaag     480
ccggtttatc tcgaaatcgc ttgcaacatt gcttccatgc cctgcgccgc tcctggaccg     540
gcaagcgcat tgttcaatga cgaagccagc gacgaagctt ctttgaatgc agcggttgaa     600
gaaacccctga aattcatcgc caaccgcgac aaagttgccg tcctcgtcgg cagcaagctg     660
```

```
cgcgcagctg gtgctgaaga agctgctgtc aaatttgctg atgctctcgg tggcgcagtt      720
gctaccatgg ctgctgcaaa aagcttcttc ccagaagaaa acccgcatta tccggcacc       780 tcatggggtg aagtcagcta tccgggcgtt gaaaagacga tgaaagaagc cgatgcggtt      840
atcgctctgg ctcctgtctt caacgactac tccaccactg gttggacgga tattcctgat      900
cctaagaaac tggttctcgc tgaaccgcgt tctgtcgtcg ttaacggcat tcgcttcccc      960
agcgtccatc tgaaagacta tctgacccgt ttggctcaga agtttccaa gaaaaccggt      1020 gcattggact tcttcaaatc cctcaatgca ggtgaactga agaaagccgc tccggctgat     1080
ccgagtgctc cgttggtcaa cgcagaaatc gcccgtcagg tcgaagctct tctgaccccg     1140
aacacgacgg ttattgctga aaccggtgac tcttggttca atgctcagcg catgaagctc     1200
ccgaacggtg ctcgcgttga atatgaaatg cagtggggtc acattggttg gtccgttcct     1260
gccgccttcg gttatgccgt cggtgctccg gaacgtcgca acatcctcat ggttggtgat     1320
ggttccttcc agctgacggc tcaggaagtc gctcagatgg ttcgcctgaa actgccggtt     1380
atcatcttct tgatcaataa ctatggttac accatcgaag ttatgatcca tgatggtccg     1440
tacaacaaca tcaagaactg ggattatgcc ggtctgatgg aagtgttcaa cggtaacggt     1500
ggttatgaca gcggtgctgg taaaggcctg aaggctaaaa ccggtggcga actggcagaa     1560
gctatcaagg ttgctctggc aaacaccgac ggcccaaccc tgatcgaatg cttcatcggt     1620
cgtgaagact gcactgaaga attggtcaaa tggggtaagc gcgttgctgc cgccaacagc     1680
cgtaagcctg ttaacaagct cctctag                                         1707

<210> SEQ ID NO 13
<211> LENGTH: 1587
<212> TYPE: DNA
<213> ORGANISM: Pseudomonas putida
<300> PUBLICATION INFORMATION:
<308> DATABASE ACCESSION NUMBER: AP013070.1
<309> DATABASE ENTRY DATE: 2014-03-01
<313> RELEVANT RESIDUES IN SEQ ID NO: (5446976)..(5448562)

<400> SEQUENCE: 13
atggcttcgg tacacggcac cacatacgaa ctcttgcgac gtcaaggcat cgatacggtc       60
ttcggcaatc ctggctcgaa cgagctcccg tttttgaagg actttccaga ggactttcga     120
tacatcctgg ctttgcagga agcgtgtgtg gtgggcattg cagacggcta tgcgcaagcc     180
agtcggaagc cggctttcat taacctgcat tctgctgctg gtaccggcaa tgctatgggt     240
gcactcagta acgcctggaa ctcacattcc ccgctgatcg tcactgccgg ccagcagacc     300
agggcgatga ttggcgttga agctctgctg accaacgtcg atgccgccaa cctgccacga     360
ccacttgtca atggagctcg gagcccgca agcgcagcag aagtccctca tgcgatgagc      420
agggctatcc atatggcaag catggcgcca caaggccctg tctatctttc ggtgccatat     480
gacgattggg ataaggatgc tgatcctcag tcccaccacc ttttgatcg ccatgtcagt      540 tcatcagtac gcctgaacga ccaggatctc gatattctgg tgaaagctct caacagcgca     600
tccaacccgg cgatcgtcct gggcccggac gtcgacgcag caaatgcgaa cgcagactgc     660
gtcatgttgg ccgaacgcct caaagctccg gtttgggttg cgccatccgc tccacgctgc     720
ccattcccta cccgtcatcc ttgcttccgt ggattgatgc cagctggcat cgcagcgatt     780
tctcagctgc tcgaaggtca cgatgtggtt ttggtaatcg cgctccagt gttccgttac      840 caccaatacg acccaggtca atatctcaaa cctggcacgc gattgatttc ggtgacctgc     900
gacccgctcg aagctgcacg cgcgccaatg ggcgatgcga tcgtggcaga cattggtgcg     960
```

```
atggctagcg ctcttgccaa cttggttgaa gagagcagcc gccagctccc aactgcagct    1020
ccggaacccg cgaaggttga ccaagacgct ggccgacttc acccagagac agtgttcgac    1080
acactgaacg acatggcccc ggagaatgcg atttacctga cgagtcgac ttcaacgacc     1140 gcccaaatgt ggcagcgcct gaacatgcgc aaccctggta gctactactt ctgtgcagct    1200
ggcggactgg gcttcgccct gcctgcagca attggcgttc aactcgcaga cccgagcga    1260 caagtcatcg ccgtcattgg cgacggatcg gcgaactaca gcattagtgc gttgtggact    1320
gcagctcagt acaacatccc cactatcttc gtgatcatga caacggcac ctacggtgcg     1380 ttgcgatggt ttgccggcgt tctcgaagca gaaaacgttc ctgggctgga tgtgccaggg    1440
atcgacttcc gcgcactcgc caagggctat ggtgtccaag cgctgaaagc cgacaacctt    1500
gagcagctca agggttcgct acaagaagcg ctttctgcca aaggcccggt acttatcgaa    1560
gtaagcaccg taagcccggt gaagtga                                        1587

<210> SEQ ID NO 14
<211> LENGTH: 1644
<212> TYPE: DNA
<213> ORGANISM: Lactococcus lactis
<300> PUBLICATION INFORMATION:
<308> DATABASE ACCESSION NUMBER: AY548760.1
<309> DATABASE ENTRY DATE: 2004-12-27
<313> RELEVANT RESIDUES IN SEQ ID NO: (100)..(1743)

<400> SEQUENCE: 14
atgtatacag taggagatta cctgttagac cgattacacg agttgggaat tgaagaaatt     60
tttggagttc ctggtgacta taacttacaa tttttagatc aaattatttc acgcgaagat    120
atgaaatgga ttgaaatgc taatgaatta aatgcttctt atatggctga tggttatgct     180
cgtactaaaa aagctgccgc atttctcacc acatttggag tcggcgaatt gagtgcgatc    240
aatggactgg caggaagtta tgccgaaaat ttaccagtag tagaaattgt tggttcacca    300
acttcaaaag tacaaaatga cggaaaattt gtccatcata cactagcaga tggtgatttt    360
aaacacttta tgaagatgca tgaacctgtt acagcagcgc ggactttact gacagcagaa    420
aatgccacat atgaaattga ccgagtactt tctcaattac taaaagaaag aaaaccagtc    480
tatattaact taccagtcga tgttgctgca gcaaaagcag agaagcctgc attatcttta    540 gaaaagaaa gctctacaac aaatacaact gaacaagtga ttttgagtaa gattgaagaa    600
agtttgaaaa atgcccaaaa accagtagtg attgcaggac acgaagtaat tagttttggt    660
ttagaaaaaa cggtaactca gtttgtttca gaaacaaaac taccgattac gacactaaat    720
tttggtaaaa gtgctgttga tgaatctttg ccctcatttt taggaatata taacgggaaa    780
ctttcagaaa tcagtcttaa aaattttgtg gagtccgcag actttatcct aatgcttgga    840
gtgaagctta cggactcctc aacaggtgca ttcacacatc atttagatga aaataaaatg    900
atttcactaa acatagatga aggaataatt tcaataaag tggtagaaga ttttgatttt    960
agagcagtgg tttcttcttt atcagaatta aaaggaatag aatatgaagg acaatatatt    1020
gataagcaat atgaagaatt tattccatca agtgctccct tatcacaaga ccgtctatgg    1080
caggcagttg aaagtttgac tcaaagcaat gaaacaatcg ttgctgaaca aggaacctca    1140 tttttttggag cttcaacaat tttcttaaaa tcaaatagtc gttttattgg acaacccttta   1200 tggggttcta ttggatatac ttttccagcg gctttaggaa gccaaattgc ggataaagag    1260
agcagacacc tttatttat tggtgatggt tcacttcaac ttaccgtaca agaattagga     1320
```

```
ctatcaatca gagaaaaact caatccaatt tgttttatca taaataatga tggttataca    1380
gttgaaagag aaatccacgg acctactcaa agttataacg acattccaat gtggaattac    1440
tcgaaattac cagaaacatt tggagcaaca gaagatcgtg tagtatcaaa aattgttaga    1500
acagagaatg aatttgtgtc tgtcatgaaa gaagcccaag cagatgtcaa tagaatgtat    1560
tggatagaac tagttttgga aaagaagat gcgccaaaat tactgaaaaa aatgggtaaa    1620
ttatttgctg agcaaaataa atag                                          1644
```

```
<210> SEQ ID NO 15
<211> LENGTH: 248
<212> TYPE: PRT
<213> ORGANISM: Thermotoga maritima
<300> PUBLICATION INFORMATION:
<308> DATABASE ACCESSION NUMBER: AAD36625.1
<309> DATABASE ENTRY DATE: 2014-01-31
<313> RELEVANT RESIDUES IN SEQ ID NO: (1)..(248)

<400> SEQUENCE: 15
```

Met Ile Glu Tyr Arg Ile Glu Glu Ala Val Ala Lys Tyr Arg Glu Phe
1               5                   10                  15

Tyr Glu Phe Lys Pro Val Arg Glu Ser Ala Gly Ile Glu Asp Val Lys
            20                  25                  30

Ser Ala Ile Glu His Thr Asn Leu Lys Pro Phe Ala Thr Pro Asp Asp
        35                  40                  45

Ile Lys Lys Leu Cys Leu Glu Ala Arg Glu Asn Arg Phe His Gly Val
    50                  55                  60

Cys Val Asn Pro Cys Tyr Val Lys Leu Ala Arg Glu Glu Leu Glu Gly
65                  70                  75                  80

Thr Asp Val Lys Val Val Thr Val Val Gly Phe Pro Leu Gly Ala Asn
                85                  90                  95

Glu Thr Arg Thr Lys Ala His Glu Ala Ile Phe Ala Val Glu Ser Gly
            100                 105                 110

Ala Asp Glu Ile Asp Met Val Ile Asn Val Gly Met Leu Lys Ala Lys
        115                 120                 125

Glu Trp Glu Tyr Val Tyr Glu Asp Ile Arg Ser Val Val Glu Ser Val
    130                 135                 140

Lys Gly Lys Val Val Lys Val Ile Glu Thr Cys Tyr Leu Asp Thr
145                 150                 155                 160

Glu Glu Lys Ile Ala Ala Cys Val Ile Ser Lys Leu Ala Gly Ala His
                165                 170                 175

Phe Val Lys Thr Ser Thr Gly Phe Gly Thr Gly Gly Ala Thr Ala Glu
            180                 185                 190

Asp Val His Leu Met Lys Trp Ile Val Gly Asp Glu Met Gly Val Lys
        195                 200                 205

Ala Ser Gly Gly Ile Arg Thr Phe Glu Asp Ala Val Lys Met Ile Met
    210                 215                 220

Tyr Gly Ala Asp Arg Ile Gly Thr Ser Ser Gly Val Lys Ile Val Gln
225                 230                 235                 240

Gly Gly Glu Glu Arg Tyr Gly Gly
                245

```
<210> SEQ ID NO 16
<211> LENGTH: 224
<212> TYPE: PRT
<213> ORGANISM: Methanothermobacter thermautotrophicus
<300> PUBLICATION INFORMATION:
<308> DATABASE ACCESSION NUMBER: AAB85318.1
```

<309> DATABASE ENTRY DATE: 2014-01-30
<313> RELEVANT RESIDUES IN SEQ ID NO: (1)..(224)

<400> SEQUENCE: 16

Met Val Lys Met Asn Val Glu Thr Arg Glu Leu Ala Ser Leu Ile
1               5                   10                  15

Asp His Thr Asn Val Arg Ala Asp Ala Thr Glu Asn Asp Ile Glu Arg
            20                  25                  30

Leu Cys Arg Glu Ala Val Ser Tyr Gly Phe Arg Cys Ala Val Val Thr
        35                  40                  45

Pro Thr Asn Val Arg Leu Ala Ala Glu Leu Leu Glu Gly Thr Asp Val
50                  55                  60

Thr Val Cys Ser Val Val Gly Phe Pro Ala Gly Val Ser Thr Pro Arg
65                  70                  75                  80

Val Lys Ala Leu Glu Ala Ser Glu Ala Val Asn Gly Ala Gly Glu
                85                  90                  95

Val Asp Met Val Met Asn Ile Gly Ala Met Lys Ser Gly Asn Arg Glu
            100                 105                 110

Leu Val Tyr Arg Asp Ile Ser Gly Val Val Asp Ala Ala Gly Val Pro
        115                 120                 125

Val Lys Val Ile Leu Glu Thr Ala Tyr Leu Thr Asp Lys Glu Lys Val
    130                 135                 140

Glu Ala Cys Leu Ile Ser Lys Glu Ala Gly Ala Ala Phe Val Lys Thr
145                 150                 155                 160

Ser Thr Ala Tyr Gly Gly Leu Ala Gly Ala Thr Val Glu Asp Val Met
                165                 170                 175

Leu Met Arg Lys Thr Val Gly Asp Glu Met Gly Val Lys Ala Ser Gly
            180                 185                 190

Gly Ile Arg Asp Leu Glu Thr Ala Leu Ala Met Ile Asp Ala Gly Ala
        195                 200                 205

Asp Arg Ile Gly Thr Ser Thr Gly Val Gln Ile Ile Glu Gly Trp Arg
    210                 215                 220

<210> SEQ ID NO 17
<211> LENGTH: 220
<212> TYPE: PRT
<213> ORGANISM: Deinococcus radiodurans
<300> PUBLICATION INFORMATION:
<308> DATABASE ACCESSION NUMBER: AAF10775.1
<309> DATABASE ENTRY DATE: 2014-01-31
<313> RELEVANT RESIDUES IN SEQ ID NO: (1)..(220)

<400> SEQUENCE: 17

Met Ser Leu Ala Ser Tyr Ile Asp His Thr Leu Leu Lys Ala Thr Ala
1               5                   10                  15

Thr Leu Ala Asp Ile Arg Thr Leu Cys Glu Glu Ala Arg Glu His Ser
            20                  25                  30

Phe Tyr Ala Val Cys Ile Asn Pro Val Phe Ile Pro His Ala Arg Ala
        35                  40                  45

Trp Leu Glu Gly Ser Asp Val Lys Val Ala Thr Val Cys Gly Phe Pro
    50                  55                  60

Leu Gly Ala Ile Ser Ser Glu Gln Lys Ala Leu Glu Ala Arg Leu Ser
65                  70                  75                  80

Ala Glu Thr Gly Ala Asp Glu Ile Asp Met Val Ile His Ile Gly Ser
                85                  90                  95

Ala Leu Ala Gly Asp Trp Asp Ala Val Glu Ala Asp Val Arg Ala Val
            100                 105                 110

-continued

Arg Arg Ala Val Pro Glu Gln Val Leu Lys Val Ile Ile Glu Thr Cys
        115                 120                 125

Tyr Leu Thr Asp Glu Gln Lys Arg Leu Ala Thr Glu Val Ala Val Gln
    130                 135                 140

Gly Gly Ala Asp Phe Val Lys Thr Ser Thr Gly Phe Gly Thr Gly Gly
145                 150                 155                 160

Ala Thr Val Asp Asp Val Arg Leu Met Ala Glu Val Ile Gly Gly Arg
                165                 170                 175

Ala Gly Leu Lys Ala Ala Gly Gly Val Arg Thr Pro Ala Asp Ala Gln
            180                 185                 190

Ala Met Ile Glu Ala Gly Ala Thr Arg Leu Gly Thr Ser Gly Gly Val
        195                 200                 205

Gly Leu Val Ser Gly Gly Glu Asn Gly Ala Gly Tyr
    210                 215                 220

<210> SEQ ID NO 18
<211> LENGTH: 220
<212> TYPE: PRT
<213> ORGANISM: Staphylococcus aureus subsp. aureus Mu50
<300> PUBLICATION INFORMATION:
<308> DATABASE ACCESSION NUMBER: WP_001083318.1
<309> DATABASE ENTRY DATE: 2015-04-27
<313> RELEVANT RESIDUES IN SEQ ID NO: (1)..(220)

<400> SEQUENCE: 18

Met Asn Ser Ala Lys Leu Ile Asp His Thr Leu Leu Lys Pro Glu Ser
1               5                   10                  15

Thr Arg Thr Gln Ile Asp Gln Ile Ile Asp Glu Ala Lys Ala Tyr His
            20                  25                  30

Phe Lys Ser Val Cys Val Asn Pro Thr His Val Lys Tyr Ala Ala Glu
        35                  40                  45

Arg Leu Ala Asp Ser Glu Val Leu Val Cys Thr Val Ile Gly Phe Pro
    50                  55                  60

Leu Gly Ala Ser Thr Thr Ala Thr Lys Ala Phe Glu Thr Glu Asp Ala
65                  70                  75                  80

Ile Gln Asn Gly Ala Asp Glu Ile Asp Met Val Ile Asn Ile Gly Ala
                85                  90                  95

Leu Lys Asp Gly Arg Phe Asp Asp Val Gln Gln Asp Ile Glu Ala Val
            100                 105                 110

Val Lys Ala Ala Lys Gly His Thr Val Lys Val Ile Glu Thr Val
        115                 120                 125

Leu Leu Asp His Asp Glu Ile Val Lys Ala Ser Glu Leu Thr Lys Val
    130                 135                 140

Ala Gly Ala Asp Phe Val Lys Thr Ser Thr Gly Phe Ala Gly Gly Gly
145                 150                 155                 160

Ala Thr Ala Glu Asp Val Lys Leu Met Lys Asp Thr Val Gly Ala Asp
                165                 170                 175

Val Glu Val Lys Ala Ser Gly Gly Val Arg Asn Leu Glu Asp Phe Asn
            180                 185                 190

Lys Met Val Glu Ala Gly Ala Thr Arg Ile Gly Ala Ser Ala Gly Val
        195                 200                 205

Gln Ile Met Gln Gly Leu Glu Ala Asp Ser Asp Tyr
    210                 215                 220

<210> SEQ ID NO 19
<211> LENGTH: 220

<212> TYPE: PRT
<213> ORGANISM: Streptococcus pneumoniae TIGR4
<300> PUBLICATION INFORMATION:
<308> DATABASE ACCESSION NUMBER: WP_000773677.1
<309> DATABASE ENTRY DATE: 2013-05-15
<313> RELEVANT RESIDUES IN SEQ ID NO: (1)..(220)

<400> SEQUENCE: 19

Met Lys Leu Asn Lys Tyr Ile Asp His Thr Leu Leu Lys Gln Asp Ala
1               5                   10                  15

Lys Lys Lys Gln Ile Asp Ser Leu Leu Ser Glu Ala Arg Glu Tyr Asp
            20                  25                  30

Phe Ala Ser Val Cys Val Asn Pro Thr Trp Val Glu His Ala Lys Lys
        35                  40                  45

Gly Leu Glu Gly Thr Asp Val Lys Val Cys Thr Val Gly Phe Pro
    50                  55                  60

Leu Gly Ala Thr Thr Ser Ala Val Lys Ala Phe Glu Thr Lys Glu Ala
65                  70                  75                  80

Ile Gln Asn Gly Ala Asp Glu Ile Asp Met Val Ile Asn Val Gly Ala
                85                  90                  95

Leu Lys Ser Gly Asn Leu Ala Leu Val Glu Ser Asp Ile Arg Ala Val
            100                 105                 110

Val Glu Ala Ser Gly Asp Lys Leu Val Lys Val Ile Glu Ala Cys
        115                 120                 125

Leu Leu Thr Asp Gln Glu Lys Val Val Val Cys Gln Leu Ala Gln Lys
130                 135                 140

Ala Gly Ala Asp Phe Val Lys Thr Ser Thr Gly Phe Ser Thr Gly Gly
145                 150                 155                 160

Ala Thr Ile Ala Asp Val Thr Leu Met Arg Glu Thr Val Gly Ser Asp
                165                 170                 175

Met Gly Val Lys Ala Ala Gly Gly Ala Arg Ser Tyr Ala Asp Ala Leu
            180                 185                 190

Ala Phe Val Glu Ala Gly Ala Thr Arg Ile Gly Thr Ser Ala Gly Val
        195                 200                 205

Ala Ile Leu Lys Gly Glu Leu Ala Asp Gly Asp Tyr
210                 215                 220

<210> SEQ ID NO 20
<211> LENGTH: 259
<212> TYPE: PRT
<213> ORGANISM: Escherichia coli K12
<300> PUBLICATION INFORMATION:
<308> DATABASE ACCESSION NUMBER: NP_418798.1
<309> DATABASE ENTRY DATE: 2014-12-16
<313> RELEVANT RESIDUES IN SEQ ID NO: (1)..(259)

<400> SEQUENCE: 20

Met Thr Asp Leu Lys Ala Ser Ser Leu Arg Ala Leu Lys Leu Met Asp
1               5                   10                  15

Leu Thr Thr Leu Asn Asp Asp Thr Asp Lys Val Ile Ala Leu
            20                  25                  30

Cys His Gln Ala Lys Thr Pro Val Gly Asn Thr Ala Ala Ile Cys Ile
        35                  40                  45

Tyr Pro Arg Phe Ile Pro Ile Ala Arg Lys Thr Leu Lys Glu Gln Gly
    50                  55                  60

Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr

-continued

```
                85                  90                  95
Gly Ala Asp Glu Val Asp Val Val Phe Pro Tyr Arg Ala Leu Met Ala
            100                 105                 110
Gly Asn Glu Gln Val Gly Phe Asp Leu Val Lys Ala Cys Lys Glu Ala
            115                 120                 125
Cys Ala Ala Ala Asn Val Leu Leu Lys Val Ile Ile Glu Thr Gly Glu
            130                 135                 140
Leu Lys Asp Glu Ala Leu Ile Arg Lys Ala Ser Glu Ile Ser Ile Lys
145                 150                 155                 160
Ala Gly Ala Asp Phe Ile Lys Thr Ser Thr Gly Lys Val Ala Val Asn
                165                 170                 175
Ala Thr Pro Glu Ser Ala Arg Ile Met Met Glu Val Ile Arg Asp Met
            180                 185                 190
Gly Val Glu Lys Thr Val Gly Phe Lys Pro Ala Gly Gly Val Arg Thr
            195                 200                 205
Ala Glu Asp Ala Gln Lys Tyr Leu Ala Ile Ala Asp Glu Leu Phe Gly
            210                 215                 220
Ala Asp Trp Ala Asp Ala Arg His Tyr Arg Phe Gly Ala Ser Ser Leu
225                 230                 235                 240
Leu Ala Ser Leu Leu Lys Ala Leu Gly His Gly Asp Gly Lys Ser Ala
                245                 250                 255
Ser Ser Tyr
```

<210> SEQ ID NO 21
<211> LENGTH: 223
<212> TYPE: PRT
<213> ORGANISM: Listeria monocytogenes EGD-e
<300> PUBLICATION INFORMATION:
<308> DATABASE ACCESSION NUMBER: NP_465519.1
<309> DATABASE ENTRY DATE: 2014-12-17
<313> RELEVANT RESIDUES IN SEQ ID NO: (1)..(223)

<400> SEQUENCE: 21

```
Met Thr Ile Ala Lys Met Ile Asp His Thr Ala Leu Lys Pro Asp Thr
1               5                   10                  15
Thr Lys Glu Gln Ile Leu Thr Leu Thr Lys Gly Ala Arg Glu Tyr Gly
            20                  25                  30
Phe Ala Ser Val Cys Val Asn Pro Thr Trp Val Lys Leu Ser Ala Glu
        35                  40                  45
Gln Leu Ala Gly Ala Glu Ser Val Val Cys Thr Val Ile Gly Phe Pro
    50                  55                  60
Leu Gly Ala Asn Thr Pro Glu Val Lys Ala Phe Glu Val Lys Asp Ala
65                  70                  75                  80
Ile Gln Asn Gly Ala Lys Glu Val Asp Met Val Ile Asn Ile Gly Ala
                85                  90                  95
Leu Lys Asp Lys Asp Glu Leu Val Glu Arg Asp Ile Arg Ala Val
            100                 105                 110
Val Asp Val Ala Lys Gly Lys Ala Leu Val Lys Val Ile Ile Glu Thr
            115                 120                 125
Cys Leu Leu Thr Asp Glu Glu Lys Val Arg Ala Cys Glu Ile Ala Val
            130                 135                 140
Lys Ala Gly Thr Asp Phe Val Lys Thr Ser Thr Gly Phe Ser Thr Gly
145                 150                 155                 160
Gly Ala Thr Ala Glu Asp Ile Ala Leu Met Arg Lys Thr Val Gly Pro
                165                 170                 175
```

```
Asn Ile Gly Val Lys Ala Ser Gly Gly Val Arg Thr Lys Glu Asp Val
            180                 185                 190

Glu Lys Met Ile Glu Ala Gly Ala Thr Arg Ile Gly Ala Ser Ala Gly
        195                 200                 205

Val Ala Ile Val Ser Gly Glu Lys Pro Ala Lys Pro Asp Asn Tyr
    210                 215                 220
```

<210> SEQ ID NO 22
<211> LENGTH: 224
<212> TYPE: PRT
<213> ORGANISM: Bacillus halodurans C-125
<300> PUBLICATION INFORMATION:
<308> DATABASE ACCESSION NUMBER: WP_010897517.1
<309> DATABASE ENTRY DATE: 2013-05-15
<313> RELEVANT RESIDUES IN SEQ ID NO: (1)..(224)

<400> SEQUENCE: 22

```
Met Ser Arg Ser Ile Ala Gln Met Ile Asp His Thr Leu Leu Lys Pro
1               5                   10                  15

Asn Thr Thr Glu Asp Gln Ile Val Lys Leu Cys Glu Glu Ala Lys Glu
            20                  25                  30

Tyr Ser Phe Ala Ser Val Cys Val Asn Pro Thr Trp Val Ala Leu Ala
        35                  40                  45

Ala Gln Leu Leu Lys Asp Ala Pro Asp Val Lys Val Cys Thr Val Ile
    50                  55                  60

Gly Phe Pro Leu Gly Ala Thr Thr Pro Glu Val Lys Ala Phe Glu Thr
65                  70                  75                  80

Thr Asn Ala Ile Glu Asn Gly Ala Thr Glu Val Asp Met Val Ile Asn
                85                  90                  95

Ile Gly Ala Leu Lys Asp Lys Gln Tyr Glu Leu Val Gly Arg Asp Ile
            100                 105                 110

Gln Ala Val Val Lys Ala Ala Glu Gly Lys Ala Leu Thr Lys Val Ile
        115                 120                 125

Ile Glu Thr Ser Leu Leu Thr Glu Glu Lys Lys Ala Ala Cys Glu
    130                 135                 140

Leu Ala Val Lys Ala Gly Ala Asp Phe Val Lys Thr Ser Thr Gly Phe
145                 150                 155                 160

Ser Gly Gly Gly Ala Thr Ala Glu Asp Ile Ala Leu Met Arg Lys Val
                165                 170                 175

Val Gly Pro Asn Leu Gly Val Lys Ala Ser Gly Gly Val Arg Asp Leu
            180                 185                 190

Ser Asp Ala Lys Ala Met Ile Asp Ala Gly Ala Thr Arg Ile Gly Ala
        195                 200                 205

Ser Ala Gly Val Ala Ile Val Asn Gly Glu Arg Ser Glu Gly Ser Tyr
    210                 215                 220
```

<210> SEQ ID NO 23
<211> LENGTH: 223
<212> TYPE: PRT
<213> ORGANISM: Bacillus cereus ATCC 10987
<300> PUBLICATION INFORMATION:
<308> DATABASE ACCESSION NUMBER: WP_001017443.1
<309> DATABASE ENTRY DATE: 2013-08-28
<313> RELEVANT RESIDUES IN SEQ ID NO: (1)..(223)

<400> SEQUENCE: 23

```
Met Asn Ile Ala Lys Leu Ile Asp His Thr Ile Leu Lys Ala Asn Thr
1               5                   10                  15

Thr Lys Glu Asp Val Met Lys Val Ile Glu Glu Ala Lys Glu Tyr Lys
```

```
            20                  25                  30
Phe Ala Ser Val Cys Ile Asn Pro Thr Trp Val Lys Leu Ala Ala Glu
            35                  40                  45

Glu Leu Ala Gly His Asp Val Asp Val Cys Thr Val Ile Gly Phe Pro
        50                  55                  60

Leu Gly Ala Ser Thr Thr Glu Thr Lys Ala Phe Glu Thr Lys Asp Ala
 65                 70                  75                  80

Ile Ala Lys Gly Ala Thr Glu Val Asp Met Val Ile Asn Val Gly Ala
                85                  90                  95

Leu Lys Asp Gly Asp Asp Glu Leu Val Glu Lys Asp Ile Tyr Glu Val
            100                 105                 110

Val Gln Ala Ala Lys Gly Lys Ala Leu Val Lys Val Ile Ile Glu Thr
        115                 120                 125

Cys Leu Leu Thr Asp Glu Glu Lys Val Arg Ala Cys Glu Leu Ser Val
    130                 135                 140

Lys Ala Gly Ala Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Pro
                165                 170                 175

Asn Val Gly Val Lys Ala Ser Gly Gly Val Arg Thr Arg Glu Asp Ala
            180                 185                 190

Glu Lys Met Val Ala Ala Gly Ala Ser Arg Val Gly Ala Ser Ala Ser
        195                 200                 205

Val Ala Ile Val Leu Asn Asp Ala Lys Gly Ala Thr Asp Asn Tyr
    210                 215                 220

<210> SEQ ID NO 24
<211> LENGTH: 223
<212> TYPE: PRT
<213> ORGANISM: Bacillus subtilis subsp. subtilis str. 168
<300> PUBLICATION INFORMATION:
<308> DATABASE ACCESSION NUMBER: CAB15978.2
<309> DATABASE ENTRY DATE: 2015-02-27
<313> RELEVANT RESIDUES IN SEQ ID NO: (1)..(223)

<400> SEQUENCE: 24

Met Ser Leu Ala Asn Ile Ile Asp His Thr Ala Leu Lys Pro His Thr
 1               5                  10                  15

Gln Lys Ala Asp Ile Leu Lys Leu Ile Glu Glu Ala Lys Thr Tyr Lys
            20                  25                  30

Phe Ala Ser Val Cys Val Asn Pro Thr Trp Val Glu Leu Ala Ala Lys
            35                  40                  45

Glu Leu Lys Gly Thr Gly Val Asp Val Cys Thr Val Ile Gly Phe Pro
        50                  55                  60

Leu Gly Ala Asn Thr Thr Glu Thr Lys Ala Phe Glu Thr Lys Asp Ala
 65                 70                  75                  80

Ile Ser Lys Gly Ala Thr Glu Val Asp Met Val Ile Asn Ile Ala Ala
                85                  90                  95

Leu Lys Asp Lys Glu Asp Val Val Glu Ala Asp Ile Arg Gly Val
            100                 105                 110

Val Glu Ala Val Ala Gly Lys Ala Leu Val Lys Val Ile Ile Glu Thr
        115                 120                 125

Cys Leu Leu Thr Asp Glu Glu Lys Glu Arg Ala Cys Arg Leu Ala Val
    130                 135                 140

Ser Ala Gly Ala Asp Phe Val Lys Thr Ser Thr Gly Phe Ser Thr Gly
145                 150                 155                 160
```

```
Gly Ala Thr Lys Glu Asp Ile Ala Leu Met Arg Lys Thr Val Gly Pro
                165                 170                 175

Asp Ile Gly Val Lys Ala Ser Gly Gly Val Arg Thr Lys Glu Asp Val
            180                 185                 190

Asp Thr Met Val Glu Ala Gly Ala Ser Arg Ile Gly Ala Ser Ala Gly
        195                 200                 205

Val Ser Ile Val Lys Gly Glu Asn Ala Ser Gly Gly Asp Asn Tyr
    210                 215                 220

<210> SEQ ID NO 25
<211> LENGTH: 329
<212> TYPE: PRT
<213> ORGANISM: Pseudomonas aeruginosa
<300> PUBLICATION INFORMATION:
<308> DATABASE ACCESSION NUMBER: NP_249818.1
<309> DATABASE ENTRY DATE: 2015-04-20
<313> RELEVANT RESIDUES IN SEQ ID NO: (1)..(329)

<400> SEQUENCE: 25

Met Ser Val Glu Ser Ile Arg Ile Glu Gly Ile Asp Thr Pro Val Ser
1               5                   10                  15

Arg Ile Gly Leu Gly Thr Trp Ala Ile Gly Gly Trp Met Trp Gly Gly
            20                  25                  30

Ala Asp Asp Ala Thr Ser Val Glu Thr Ile Arg Arg Ala Val Glu Ser
        35                  40                  45

Gly Ile Asn Leu Ile Asp Thr Ala Pro Val Tyr Gly Phe Gly His Ser
    50                  55                  60

Glu Glu Val Val Gly Lys Ala Leu Gln Gly Leu Arg Asp Lys Ala Val
65                  70                  75                  80

Ile Ala Thr Lys Ala Ala Leu Glu Trp Ser Asp Ala Gly Ile His Arg
                85                  90                  95

Asn Ala Ser Ala Ala Arg Ile Arg Arg Glu Val Glu Asp Ser Leu Arg
            100                 105                 110

Arg Leu Lys Thr Asp Arg Ile Asp Leu Tyr Gln Ile His Trp Pro Asp
        115                 120                 125

Pro Leu Val Ala His Glu Glu Thr Ala Gly Glu Leu Glu Arg Leu Arg
    130                 135                 140

Arg Asp Gly Lys Ile Leu Ala Ile Gly Val Ser Asn Tyr Ser Pro Glu
145                 150                 155                 160

Gln Met Asp Gly Phe Arg Gln Phe Ala Pro Leu Ala Ser Val Gln Pro
                165                 170                 175

Pro Tyr Asn Leu Phe Glu Arg Ala Ile Asp Ala Asp Val Leu Pro Tyr
            180                 185                 190

Ala Glu Arg Asn Gly Ile Val Val Leu Ala Tyr Gly Ala Leu Cys Arg
        195                 200                 205

Gly Leu Leu Ser Gly Arg Met Asn Ala Glu Thr Arg Phe Asp Gly Asp
    210                 215                 220

Asp Leu Arg Lys Ser Asp Pro Lys Phe Gln Gln Pro Arg Phe Ala Gln
225                 230                 235                 240

Tyr Leu Ala Ala Val Ala Gln Leu Glu Glu Leu Ala Arg Glu Arg Tyr
                245                 250                 255

Gly Lys Ser Val Leu Ala Leu Ala Ile Arg Trp Ile Leu Asp Arg Gly
            260                 265                 270

Pro Thr Val Ala Leu Trp Gly Ala Arg Lys Pro Glu Gln Leu Asn Gly
        275                 280                 285
```

Ile Ala Asp Ala Phe Gly Trp Arg Leu Asp Asp Glu Ala Met Ala Arg
290                 295                 300

Ile Glu Arg Ile Leu Ala Glu Thr Ile Gln Asp Pro Val Gly Pro Glu
305                 310                 315                 320

Phe Met Ala Pro Pro Ser Arg Asn Ala
                325

<210> SEQ ID NO 26
<211> LENGTH: 568
<212> TYPE: PRT
<213> ORGANISM: Zymomonas mobilis
<300> PUBLICATION INFORMATION:
<308> DATABASE ACCESSION NUMBER: WP_011241152.1
<309> DATABASE ENTRY DATE: 2015-04-27
<313> RELEVANT RESIDUES IN SEQ ID NO: (1)..(568)

<400> SEQUENCE: 26

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Asn Leu Leu Leu Asn Lys Asn Met Glu Gln Val Tyr Cys Cys
            35                  40                  45

Asn Glu Leu Asn Cys Gly Phe Ser Ala Glu Gly Tyr Ala Arg Ala Lys
        50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
210                 215                 220

Ala Glu Glu Ala Ala Val Lys Phe Ala Asp Ala Leu Gly Gly Ala Val
225                 230                 235                 240

Ala Thr Met Ala Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
290                 295                 300

Val Leu Ala Glu Pro Arg Ser Val Val Val Asn Gly Ile Arg Phe Pro

```
            305                 310                 315                 320
    Ser Val His Leu Lys Asp Tyr Leu Thr Arg Leu Ala Gln Lys Val Ser
                    325                 330                 335

Lys Lys Thr Gly Ala Leu Asp Phe Phe Lys Ser Leu Asn Ala Gly Glu
                    340                 345                 350

Leu Lys Lys Ala Ala Pro Ala Asp Pro Ser Ala Pro Leu Val Asn Ala
                    355                 360                 365

Glu Ile Ala Arg Gln Val Glu Ala Leu Leu Thr Pro Asn Thr Thr Val
                    370                 375                 380

Ile Ala Glu Thr Gly Asp Ser Trp Phe Asn Ala Gln Arg Met Lys Leu
    385                 390                 395                 400

Pro Asn Gly Ala Arg Val Glu Tyr Glu Met Gln Trp Gly His Ile Gly
                    405                 410                 415

Trp Ser Val Pro Ala Ala Phe Gly Tyr Ala Val Gly Ala Pro Glu Arg
                    420                 425                 430

Arg Asn Ile Leu Met Val Gly Asp Gly Ser Phe Gln Leu Thr Ala Gln
                    435                 440                 445

Glu Val Ala Gln Met Val Arg Leu Lys Leu Pro Val Ile Ile Phe Leu
                    450                 455                 460

Ile Asn Asn Tyr Gly Tyr Thr Ile Glu Val Met Ile His Asp Gly Pro
    465                 470                 475                 480

Tyr Asn Asn Ile Lys Asn Trp Asp Tyr Ala Gly Leu Met Glu Val Phe
                    485                 490                 495

Asn Gly Asn Gly Gly Tyr Asp Ser Gly Ala Gly Lys Gly Leu Lys Ala
                    500                 505                 510

Lys Thr Gly Gly Glu Leu Ala Glu Ala Ile Lys Val Ala Leu Ala Asn
                    515                 520                 525

Thr Asp Gly Pro Thr Leu Ile Glu Cys Phe Ile Gly Arg Glu Asp Cys
                    530                 535                 540

Thr Glu Glu Leu Val Lys Trp Gly Lys Arg Val Ala Ala Ala Asn Ser
    545                 550                 555                 560

Arg Lys Pro Val Asn Lys Leu Leu
                    565

<210> SEQ ID NO 27
<211> LENGTH: 528
<212> TYPE: PRT
<213> ORGANISM: Pseudomonas putida
<300> PUBLICATION INFORMATION:
<308> DATABASE ACCESSION NUMBER: WP_016501746.1
<309> DATABASE ENTRY DATE: 2015-04-27
<313> RELEVANT RESIDUES IN SEQ ID NO: (1)..(528)

<400> SEQUENCE: 27

Met Ala Ser Val His Gly Thr Thr Tyr Glu Leu Leu Arg Arg Gln Gly
    1               5                   10                  15

Ile Asp Thr Val Phe Gly Asn Pro Gly Ser Asn Glu Leu Pro Phe Leu
                    20                  25                  30

Lys Asp Phe Pro Glu Asp Phe Arg Tyr Ile Leu Ala Leu Gln Glu Ala
                    35                  40                  45

Cys Val Val Gly Ile Ala Asp Gly Tyr Ala Gln Ala Ser Arg Lys Pro
                    50                  55                  60

Ala Phe Ile Asn Leu His Ser Ala Ala Gly Thr Gly Asn Ala Met Gly
    65                  70                  75                  80

Ala Leu Ser Asn Ala Trp Asn Ser His Ser Pro Leu Ile Val Thr Ala
                    85                  90                  95
```

-continued

Gly Gln Gln Thr Arg Ala Met Ile Gly Val Glu Ala Leu Leu Thr Asn
            100                 105                 110

Val Asp Ala Ala Asn Leu Pro Arg Pro Leu Val Lys Trp Ser Tyr Glu
            115                 120                 125

Pro Ala Ser Ala Ala Glu Val Pro His Ala Met Ser Arg Ala Ile His
            130                 135                 140

Met Ala Ser Met Ala Pro Gln Gly Pro Val Tyr Leu Ser Val Pro Tyr
145                 150                 155                 160

Asp Asp Trp Asp Lys Asp Ala Asp Pro Gln Ser His His Leu Phe Asp
                165                 170                 175

Arg His Val Ser Ser Val Arg Leu Asn Asp Gln Asp Leu Asp Ile
            180                 185                 190

Leu Val Lys Ala Leu Asn Ser Ala Ser Asn Pro Ala Ile Val Leu Gly
            195                 200                 205

Pro Asp Val Asp Ala Ala Asn Ala Asn Ala Asp Cys Val Met Leu Ala
            210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Val Val Leu Val
            260                 265                 270

Ile Gly Ala Pro Val Phe Arg Tyr His Gln Tyr Asp Pro Gly Gln Tyr
            275                 280                 285

Leu Lys Pro Gly Thr Arg Leu Ile Ser Val Thr Cys Asp Pro Leu Glu
            290                 295                 300

Ala Ala Arg Ala Pro Met Gly Asp Ala Ile Val Ala Asp Ile Gly Ala
305                 310                 315                 320

Met Ala Ser Ala Leu Ala Asn Leu Val Glu Glu Ser Ser Arg Gln Leu
                325                 330                 335

Pro Thr Ala Ala Pro Glu Pro Ala Lys Val Asp Gln Asp Ala Gly Arg
            340                 345                 350

Leu His Pro Glu Thr Val Phe Asp Thr Leu Asn Asp Met Ala Pro Glu
            355                 360                 365

Asn Ala Ile Tyr Leu Asn Glu Ser Thr Ser Thr Thr Ala Gln Met Trp
370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Glu Arg Gln Val Ile Ala Val Ile Gly Asp Gly Ser Ala Asn
            420                 425                 430

Tyr Ser Ile Ser Ala Leu Trp Thr Ala Ala Gln Tyr Asn Ile Pro Thr
            435                 440                 445

Ile Phe Val Ile Met Asn Asn Gly Thr Tyr Gly Ala Leu Arg Trp Phe
            450                 455                 460

Ala Gly Val Leu Glu Ala Glu Asn Val Pro Gly Leu Asp Val Pro Gly
465                 470                 475                 480

Ile Asp Phe Arg Ala Leu Ala Lys Gly Tyr Gly Val Gln Ala Leu Lys
                485                 490                 495

Ala Asp Asn Leu Glu Gln Leu Lys Gly Ser Leu Gln Glu Ala Leu Ser
            500                 505                 510

```
Ala Lys Gly Pro Val Leu Ile Glu Val Ser Thr Val Ser Pro Val Lys
        515                 520                 525

<210> SEQ ID NO 28
<211> LENGTH: 547
<212> TYPE: PRT
<213> ORGANISM: Lactococcus lactis
<300> PUBLICATION INFORMATION:
<308> DATABASE ACCESSION NUMBER: WP_046124870.1
<309> DATABASE ENTRY DATE: 2015-04-08
<313> RELEVANT RESIDUES IN SEQ ID NO: (1)..(547)

<400> SEQUENCE: 28

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
```

```
                    340                 345                 350
Pro Leu Ser Gln Asp Arg Leu Trp Gln Ala Val Glu Ser Leu Thr Gln
                355                 360                 365
Ser Asn Glu Thr Ile Val Ala Glu Gln Gly Thr Ser Phe Phe Gly Ala
            370                 375                 380
Ser Thr Ile Phe Leu Lys Ser Asn Ser Arg Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ser Ile Arg Glu Lys Leu Asn
        435                 440                 445
Pro Ile Cys Phe Ile Ile Asn Asn Asp Gly Tyr Thr Val Glu Arg Glu
            450                 455                 460
Ile His Gly Pro Thr Gln Ser Tyr Asn Asp Ile Pro Met Trp Asn Tyr
465                 470                 475                 480
Ser Lys Leu Pro Glu Thr Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
Gln Ala Asp Val Asn Arg Met Tyr Trp Ile Glu Leu Val Leu Glu Lys
        515                 520                 525
Glu Asp Ala Pro Lys Leu Leu Lys Lys Met Gly Lys Leu Phe Ala Glu
    530                 535                 540
Gln Asn Lys
545

<210> SEQ ID NO 29
<211> LENGTH: 49
<212> TYPE: DNA
<213> ORGANISM: ARTIFICIAL SEQUENCE
<220> FEATURE:
<223> OTHER INFORMATION: Primer

<400> SEQUENCE: 29
cctcgtctca accaaagcaa tcaacccatc agtcgacctg caggcatgc              49

<210> SEQ ID NO 30
<211> LENGTH: 53
<212> TYPE: DNA
<213> ORGANISM: ARTIFICIAL SEQUENCE
<220> FEATURE:
<223> OTHER INFORMATION: Primer

<400> SEQUENCE: 30
cgagacagcc tgagaatgga tgcgagtaat gcgagctcga attccatggt ctg          53

<210> SEQ ID NO 31
<211> LENGTH: 63
<212> TYPE: DNA
<213> ORGANISM: ARTIFICIAL SEQUENCE
<220> FEATURE:
<223> OTHER INFORMATION: Primer

<400> SEQUENCE: 31
gctgggagtt cgtagacgga aacaaacgca aggaggtatt gcacatgtca cgttcgattg    60
cac                                                                  63
```

<210> SEQ ID NO 32
<211> LENGTH: 51
<212> TYPE: DNA
<213> ORGANISM: ARTIFICIAL SEQUENCE
<220> FEATURE:
<223> OTHER INFORMATION: Primer

<400> SEQUENCE: 32
gtttccagtg cgattgagga ccttcagtgc ttaataactc ccttcgctac g            51

<210> SEQ ID NO 33
<211> LENGTH: 65
<212> TYPE: DNA
<213> ORGANISM: ARTIFICIAL SEQUENCE
<220> FEATURE:
<223> OTHER INFORMATION: Primer

<400> SEQUENCE: 33
ctgacctcct gccagcaata gtaagacaac aggaggtatc gggcatgagc gttgaaagca      60
ttcgc                                                                 65

<210> SEQ ID NO 34
<211> LENGTH: 49
<212> TYPE: DNA
<213> ORGANISM: ARTIFICIAL SEQUENCE
<220> FEATURE:
<223> OTHER INFORMATION: Primer

<400> SEQUENCE: 34
acttgagtga ggttgtaaag ggagttggct cttaggcgtt gcggctggg              49

<210> SEQ ID NO 35
<211> LENGTH: 66
<212> TYPE: DNA
<213> ORGANISM: ARTIFICIAL SEQUENCE
<220> FEATURE:
<223> OTHER INFORMATION: Primer

<400> SEQUENCE: 35
ctcgttcgct gccacctaag aatactctac gaggaggtat tcgccatgag ttatactgtc     60
ggtacc                                                               66

<210> SEQ ID NO 36
<211> LENGTH: 51
<212> TYPE: DNA
<213> ORGANISM: ARTIFICIAL SEQUENCE
<220> FEATURE:
<223> OTHER INFORMATION: Primer

<400> SEQUENCE: 36
agtagcggaa atgtcagagc cagcgtcttg ctagaggagc ttgttaacag g            51

<210> SEQ ID NO 37
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 37
ggtcaactaa tccttaactg atcg                                         24

<210> SEQ ID NO 38
<211> LENGTH: 23

-continued

```
<212> TYPE: DNA
<213> ORGANISM: ARTIFICIAL SEQUENCE
<220> FEATURE:
<223> OTHER INFORMATION: Primer

<400> SEQUENCE: 38
aagcaaatca tcaccgcact gac                                              23

<210> SEQ ID NO 39
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 39
caggcttagc gcaacaaacg                                                  20

<210> SEQ ID NO 40
<211> LENGTH: 19
<212> TYPE: DNA
<213> ORGANISM: ARTIFICIAL SEQUENCE
<220> FEATURE:
<223> OTHER INFORMATION: Primer

<400> SEQUENCE: 40
ggttgcgcct acactaagc                                                   19

<210> SEQ ID NO 41
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 41
tccacttaag aaggtaggtg ttac                                             24

<210> SEQ ID NO 42
<211> LENGTH: 23
<212> TYPE: DNA
<213> ORGANISM: ARTIFICIAL SEQUENCE
<220> FEATURE:
<223> OTHER INFORMATION: Primer

<400> SEQUENCE: 42
aaagttgccg ctttacgggg aaa                                              23

<210> SEQ ID NO 43
<211> LENGTH: 193
<212> TYPE: PRT
<213> ORGANISM: Aeropyrum pernix
<300> PUBLICATION INFORMATION:
<308> DATABASE ACCESSION NUMBER: BAA81452.2
<309> DATABASE ENTRY DATE: 2004-12-08
<313> RELEVANT RESIDUES IN SEQ ID NO: (1)..(193)

<400> SEQUENCE: 43

Met Arg Glu Ala Ser Asp Tyr Gly Phe Arg Cys Ala Val Leu Thr Pro
1               5                   10                  15

Val Tyr Thr Val Lys Ile Ser Gly Leu Ala Glu Lys Leu Gly Val Lys
            20                  25                  30

Leu Cys Ser Val Ile Gly Phe Pro Leu Gly Gln Ala Pro Leu Glu Val
        35                  40                  45

Lys Leu Val Glu Ala Gln Thr Val Leu Glu Ala Gly Ala Thr Glu Leu
```

```
            50                  55                  60
Asp Val Pro His Leu Ser Leu Gly Pro Glu Ala Val Tyr Arg Glu
 65                  70                  75                  80

Val Ser Gly Ile Val Lys Leu Ala Lys Ser Tyr Gly Ala Val Lys
                     85                  90                  95

Val Ile Leu Glu Ala Pro Leu Trp Asp Lys Thr Leu Ser Leu Leu
                    100                 105                 110

Val Asp Ser Ser Arg Arg Ala Gly Ala Asp Ile Val Lys Thr Ser Thr
                    115                 120                 125

Gly Val Tyr Thr Lys Gly Gly Asp Pro Val Thr Val Phe Arg Leu Ala
                    130                 135                 140

Ser Leu Ala Lys Pro Leu Gly Met Gly Val Lys Ala Ser Gly Gly Ile
145                 150                 155                 160

Arg Ser Gly Ile Asp Ala Val Leu Ala Val Gly Ala Gly Ala Asp Ile
                    165                 170                 175

Ile Gly Thr Ser Ser Ala Val Lys Val Leu Glu Ser Phe Lys Ser Leu
                    180                 185                 190

Val
```

<210> SEQ ID NO 44
<211> LENGTH: 223
<212> TYPE: PRT
<213> ORGANISM: Bacillus cereus ATCC 10987
<300> PUBLICATION INFORMATION:
<308> DATABASE ACCESSION NUMBER: NP_978291.1
<309> DATABASE ENTRY DATE: 2014-12-17
<313> RELEVANT RESIDUES IN SEQ ID NO: (1)..(223)

<400> SEQUENCE: 44

```
Met Asn Ile Ala Lys Leu Ile Asp His Thr Ile Leu Lys Ala Asn Thr
 1                   5                  10                  15

Thr Lys Glu Asp Val Met Lys Val Ile Glu Glu Ala Lys Glu Tyr Lys
                    20                  25                  30

Phe Ala Ser Val Cys Ile Asn Pro Thr Trp Val Lys Leu Ala Ala Glu
                    35                  40                  45

Glu Leu Ala Gly His Asp Val Asp Val Cys Thr Val Ile Gly Phe Pro
                    50                  55                  60

Leu Gly Ala Ser Thr Thr Glu Thr Lys Ala Phe Glu Thr Lys Asp Ala
 65                  70                  75                  80

Ile Ala Lys Gly Ala Thr Glu Val Asp Met Val Ile Asn Val Gly Ala
                    85                  90                  95

Leu Lys Asp Gly Asp Asp Glu Leu Val Glu Lys Asp Ile Tyr Glu Val
                    100                 105                 110

Val Gln Ala Ala Lys Gly Lys Ala Leu Val Lys Val Ile Ile Glu Thr
                    115                 120                 125

Cys Leu Leu Thr Asp Glu Glu Lys Val Arg Ala Cys Glu Leu Ser Val
                    130                 135                 140

Lys Ala Gly Ala Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Pro
                    165                 170                 175

Asn Val Gly Val Lys Ala Ser Gly Gly Val Arg Thr Arg Glu Asp Ala
                    180                 185                 190

Glu Lys Met Val Ala Ala Gly Ala Ser Arg Val Gly Ala Ser Ala Ser
                    195                 200                 205
```

```
Val Ala Ile Val Leu Asn Asp Ala Lys Gly Ala Thr Asp Asn Tyr
    210                 215                 220
```

<210> SEQ ID NO 45
<211> LENGTH: 223
<212> TYPE: PRT
<213> ORGANISM: Listeria monocytogenes
<300> PUBLICATION INFORMATION:
<308> DATABASE ACCESSION NUMBER: NP_465519.1
<309> DATABASE ENTRY DATE: 2016-08-28
<313> RELEVANT RESIDUES IN SEQ ID NO: (1)..(223)

<400> SEQUENCE: 45

```
Met Thr Ile Ala Lys Met Ile Asp His Thr Ala Leu Lys Pro Asp Thr
1               5                   10                  15

Thr Lys Glu Gln Ile Leu Thr Leu Thr Lys Glu Ala Arg Glu Tyr Gly
            20                  25                  30

Phe Ala Ser Val Cys Val Asn Pro Thr Trp Val Lys Leu Ser Ala Glu
        35                  40                  45

Gln Leu Ala Gly Ala Glu Ser Val Val Cys Thr Val Ile Gly Phe Pro
    50                  55                  60

Leu Gly Ala Asn Thr Pro Glu Val Lys Ala Phe Glu Val Lys Asp Ala
65                  70                  75                  80

Ile Gln Asn Gly Ala Lys Glu Val Asp Met Val Ile Asn Ile Gly Ala
                85                  90                  95

Leu Lys Asp Lys Asp Asp Glu Leu Val Glu Arg Asp Ile Arg Ala Val
            100                 105                 110

Val Asp Val Ala Lys Gly Lys Ala Leu Val Lys Val Ile Ile Glu Thr
        115                 120                 125

Cys Leu Leu Thr Asp Glu Glu Lys Val Arg Ala Cys Glu Ile Ala Val
    130                 135                 140

Lys Ala Gly Thr Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Pro
                165                 170                 175

Asn Ile Gly Val Lys Ala Ser Gly Gly Val Arg Thr Lys Glu Asp Val
            180                 185                 190

Glu Lys Met Ile Glu Ala Gly Ala Thr Arg Ile Gly Ala Ser Ala Gly
        195                 200                 205

Val Ala Ile Val Ser Gly Glu Lys Pro Ala Lys Pro Asp Asn Tyr
    210                 215                 220
```

<210> SEQ ID NO 46
<211> LENGTH: 223
<212> TYPE: PRT
<213> ORGANISM: Bacillus subtilis
<300> PUBLICATION INFORMATION:
<308> DATABASE ACCESSION NUMBER: CAB15978.2
<309> DATABASE ENTRY DATE: 2018-02-08
<313> RELEVANT RESIDUES IN SEQ ID NO: (1)..(223)

<400> SEQUENCE: 46

```
Met Ser Leu Ala Asn Ile Ile Asp His Thr Ala Leu Lys Pro His Thr
1               5                   10                  15

Gln Lys Ala Asp Ile Leu Lys Leu Ile Glu Glu Ala Lys Thr Tyr Lys
            20                  25                  30

Phe Ala Ser Val Cys Val Asn Pro Thr Trp Val Glu Leu Ala Ala Lys
        35                  40                  45

Glu Leu Lys Gly Thr Gly Val Asp Val Cys Thr Val Ile Gly Phe Pro
```

```
                    50                  55                  60

Leu Gly Ala Asn Thr Thr Glu Thr Lys Ala Phe Glu Thr Lys Asp Ala
 65                  70                  75                  80

Ile Ser Lys Gly Ala Thr Glu Val Asp Met Val Ile Asn Ile Ala Ala
                     85                  90                  95

Leu Lys Asp Lys Glu Asp Val Val Glu Ala Asp Ile Arg Gly Val
                100                 105                 110

Val Glu Ala Val Ala Gly Lys Ala Leu Val Lys Val Ile Glu Thr
                115                 120                 125

Cys Leu Leu Thr Asp Glu Glu Lys Glu Arg Ala Cys Arg Leu Ala Val
                130                 135                 140

Ser Ala Gly Ala Asp Phe Val Lys Thr Ser Thr Gly Phe Ser Thr Gly
145                 150                 155                 160

Gly Ala Thr Lys Glu Asp Ile Ala Leu Met Arg Lys Thr Val Gly Pro
                165                 170                 175

Asp Ile Gly Val Lys Ala Ser Gly Gly Val Arg Thr Lys Glu Asp Val
                180                 185                 190

Asp Thr Met Val Glu Ala Gly Ala Ser Arg Ile Gly Ala Ser Ala Gly
                195                 200                 205

Val Ser Ile Val Lys Gly Glu Asn Ala Ser Gly Gly Asp Asn Tyr
                210                 215                 220
```

<210> SEQ ID NO 47
<211> LENGTH: 224
<212> TYPE: PRT
<213> ORGANISM: Bacillus halodurans
<300> PUBLICATION INFORMATION:
<308> DATABASE ACCESSION NUMBER: NP_242218.1
<309> DATABASE ENTRY DATE: 2014-12-16
<313> RELEVANT RESIDUES IN SEQ ID NO: (1)..(224)

<400> SEQUENCE: 47

```
Met Ser Arg Ser Ile Ala Gln Met Ile Asp His Thr Leu Leu Lys Pro
  1               5                  10                  15

Asn Thr Thr Glu Asp Gln Ile Val Lys Leu Cys Glu Glu Ala Lys Glu
                 20                  25                  30

Tyr Ser Phe Ala Ser Val Cys Val Asn Pro Thr Trp Val Ala Leu Ala
                 35                  40                  45

Ala Gln Leu Leu Lys Asp Ala Pro Asp Val Lys Val Cys Thr Val Ile
 50                  55                  60

Gly Phe Pro Leu Gly Ala Thr Thr Pro Glu Val Lys Ala Phe Glu Thr
 65                  70                  75                  80

Thr Asn Ala Ile Glu Asn Gly Ala Thr Glu Val Asp Met Val Ile Asn
                 85                  90                  95

Ile Gly Ala Leu Lys Asp Lys Gln Tyr Glu Leu Val Gly Arg Asp Ile
                100                 105                 110

Gln Ala Val Val Lys Ala Ala Glu Gly Lys Ala Leu Thr Lys Val Ile
                115                 120                 125

Ile Glu Thr Ser Leu Leu Thr Glu Glu Glu Lys Lys Ala Ala Cys Glu
                130                 135                 140

Leu Ala Val Lys Ala Gly Ala Asp Phe Val Lys Thr Ser Thr Gly Phe
145                 150                 155                 160

Ser Gly Gly Gly Ala Thr Ala Glu Asp Ile Ala Leu Met Arg Lys Val
                165                 170                 175

Val Gly Pro Asn Leu Gly Val Lys Ala Ser Gly Gly Val Arg Asp Leu
                180                 185                 190
```

Ser Asp Ala Lys Ala Met Ile Asp Ala Gly Ala Thr Arg Ile Gly Ala
        195                  200                  205

Ser Ala Gly Val Ala Ile Val Asn Gly Glu Arg Ser Glu Gly Ser Tyr
    210                  215                  220

<210> SEQ ID NO 48
<211> LENGTH: 220
<212> TYPE: PRT
<213> ORGANISM: Streptococcus pneumoniae TIGR4
<300> PUBLICATION INFORMATION:
<308> DATABASE ACCESSION NUMBER: NP_345334.1
<309> DATABASE ENTRY DATE: 2014-12-17
<313> RELEVANT RESIDUES IN SEQ ID NO: (1)..(220)

<400> SEQUENCE: 48

Met Lys Leu Asn Lys Tyr Ile Asp His Thr Leu Leu Lys Gln Asp Ala
1              5                  10                 15

Lys Lys Lys Gln Ile Asp Ser Leu Leu Ser Glu Ala Arg Glu Tyr Asp
        20                 25               30

Phe Ala Ser Val Cys Val Asn Pro Thr Trp Val Glu His Ala Lys Lys
            35               40              45

Gly Leu Glu Gly Thr Asp Val Lys Val Cys Thr Val Val Gly Phe Pro
    50                  55                  60

Leu Gly Ala Thr Thr Ser Ala Val Lys Ala Phe Glu Thr Lys Glu Ala
65               70                 75                 80

Ile Gln Asn Gly Ala Asp Glu Ile Asp Met Val Ile Asn Val Gly Ala
               85               90               95

Leu Lys Ser Gly Asn Leu Ala Leu Val Glu Ser Asp Ile Arg Ala Val
        100                105              110

Val Glu Ala Ser Gly Asp Lys Leu Val Lys Val Ile Ile Glu Ala Cys
         115                120              125

Leu Leu Thr Asp Gln Glu Lys Val Val Cys Gln Leu Ala Gln Lys
    130                135              140

Ala Gly Ala Asp Phe Val Lys Thr Ser Thr Gly Phe Ser Thr Gly Gly
145             150                 155                160

Ala Thr Ile Ala Asp Val Thr Leu Met Arg Glu Thr Val Gly Ser Asp
         165                170              175

Met Gly Val Lys Ala Ala Gly Gly Ala Arg Ser Tyr Ala Asp Ala Leu
        180                185              190

Ala Phe Val Glu Ala Gly Ala Thr Arg Ile Gly Thr Ser Ala Gly Val
         195                200              205

Ala Ile Leu Lys Gly Glu Leu Ala Asp Gly Asp Tyr
    210                215                220

<210> SEQ ID NO 49
<211> LENGTH: 220
<212> TYPE: PRT
<213> ORGANISM: Staphylococcus aureus
<300> PUBLICATION INFORMATION:
<308> DATABASE ACCESSION NUMBER: NP_370662.1
<309> DATABASE ENTRY DATE: 2014-12-16
<313> RELEVANT RESIDUES IN SEQ ID NO: (1)..(220)

<400> SEQUENCE: 49

Met Lys Phe Glu Lys Tyr Ile Asp His Thr Leu Leu Lys Pro Glu Ser
1              5                  10                 15

Thr Arg Thr Gln Ile Asp Gln Ile Asp Glu Ala Lys Ala Tyr Asn
        20                 25               30

Phe Lys Ser Val Cys Val Asn Pro Thr His Val Lys Tyr Ala Ala Glu
            35                  40                  45

Arg Leu Ala Asp Ser Glu Val Leu Val Cys Thr Val Ile Gly Phe Pro
 50                  55                  60

Leu Gly Ala Ser Thr Thr Ala Thr Lys Ala Phe Glu Thr Glu Asp Ala
 65                  70                  75                  80

Ile Gln Asn Gly Ala Asp Glu Ile Asp Met Val Ile Asn Ile Gly Ala
                 85                  90                  95

Leu Lys Asp Gly Arg Phe Asp Asp Val Gln Gln Asp Ile Glu Ala Val
            100                 105                 110

Val Lys Ala Ala Lys Gly His Thr Val Lys Val Ile Ile Glu Thr Val
            115                 120                 125

Leu Leu Asp His Asp Glu Ile Val Lys Ala Ser Glu Leu Thr Lys Ala
            130                 135                 140

Ala Gly Ala Asp Phe Val Lys Thr Ser Thr Gly Phe Ala Gly Gly Gly
145                 150                 155                 160

Ala Thr Ala Glu Asp Val Lys Leu Met Lys Asp Thr Val Gly Ala Asp
                165                 170                 175

Val Glu Val Lys Ala Ser Gly Gly Val Arg Asn Leu Glu Asp Phe Asn
            180                 185                 190

Lys Met Val Glu Ala Gly Ala Thr Arg Ile Gly Ala Ser Ala Gly Val
            195                 200                 205

Gln Ile Met Gln Gly Leu Glu Ala Asp Ser Asp Tyr
            210                 215                 220

<210> SEQ ID NO 50
<211> LENGTH: 220
<212> TYPE: PRT
<213> ORGANISM: Staphylococcus aureus
<300> PUBLICATION INFORMATION:
<308> DATABASE ACCESSION NUMBER: NP_372661.1
<309> DATABASE ENTRY DATE: 2014-12-16
<313> RELEVANT RESIDUES IN SEQ ID NO: (1)..(220)

<400> SEQUENCE: 50

Met Asn Ser Ala Lys Leu Ile Asp His Thr Leu Leu Lys Pro Glu Ser
 1               5                  10                  15

Thr Arg Thr Gln Ile Asp Gln Ile Ile Asp Glu Ala Lys Ala Tyr His
                 20                  25                  30

Phe Lys Ser Val Cys Val Asn Pro Thr His Val Lys Tyr Ala Ala Glu
            35                  40                  45

Arg Leu Ala Asp Ser Glu Val Leu Val Cys Thr Val Ile Gly Phe Pro
 50                  55                  60

Leu Gly Ala Ser Thr Thr Ala Thr Lys Ala Phe Glu Thr Glu Asp Ala
 65                  70                  75                  80

Ile Gln Asn Gly Ala Asp Glu Ile Asp Met Val Ile Asn Ile Gly Ala
                 85                  90                  95

Leu Lys Asp Gly Arg Phe Asp Asp Val Gln Gln Asp Ile Glu Ala Val
            100                 105                 110

Val Lys Ala Ala Lys Gly His Thr Val Lys Val Ile Ile Glu Thr Val
            115                 120                 125

Leu Leu Asp His Asp Glu Ile Val Lys Ala Ser Glu Leu Thr Lys Val
            130                 135                 140

Ala Gly Ala Asp Phe Val Lys Thr Ser Thr Gly Phe Ala Gly Gly Gly
145                 150                 155                 160

Ala Thr Ala Glu Asp Val Lys Leu Met Lys Asp Thr Val Gly Ala Asp 165                 170                 175
Val Glu Val Lys Ala Ser Gly Gly Val Arg Asn Leu Glu Asp Phe Asn
            180                 185                 190

Lys Met Val Glu Ala Gly Ala Thr Arg Ile Gly Ala Ser Ala Gly Val
        195                 200                 205

Gln Ile Met Gln Gly Leu Glu Ala Asp Ser Asp Tyr
    210                 215                 220

<210> SEQ ID NO 51
<211> LENGTH: 220
<212> TYPE: PRT
<213> ORGANISM: Deinococcus radiodurans
<300> PUBLICATION INFORMATION:
<308> DATABASE ACCESSION NUMBER: AAF10775.1
<309> DATABASE ENTRY DATE: 2014-01-31
<313> RELEVANT RESIDUES IN SEQ ID NO: (1)..(220)

<400> SEQUENCE: 51

Met Ser Leu Ala Ser Tyr Ile Asp His Thr Leu Leu Lys Ala Thr Ala
1               5                   10                  15

Thr Leu Ala Asp Ile Arg Thr Leu Cys Glu Glu Ala Arg Glu His Ser
            20                  25                  30

Phe Tyr Ala Val Cys Ile Asn Pro Val Phe Ile Pro His Ala Arg Ala
        35                  40                  45

Trp Leu Glu Gly Ser Asp Val Lys Val Ala Thr Val Cys Gly Phe Pro
    50                  55                  60

Leu Gly Ala Ile Ser Ser Glu Gln Lys Ala Leu Glu Ala Arg Leu Ser
65                  70                  75                  80

Ala Glu Thr Gly Ala Asp Glu Ile Asp Met Val Ile His Ile Gly Ser
                85                  90                  95

Ala Leu Ala Gly Asp Trp Asp Ala Val Glu Ala Asp Val Arg Ala Val
            100                 105                 110

Arg Arg Ala Val Pro Glu Gln Val Leu Lys Val Ile Glu Thr Cys
        115                 120                 125

Tyr Leu Thr Asp Glu Gln Lys Arg Leu Ala Thr Glu Val Ala Val Gln
    130                 135                 140

Gly Gly Ala Asp Phe Val Lys Thr Ser Thr Gly Phe Gly Thr Gly Gly
145                 150                 155                 160

Ala Thr Val Asp Asp Val Arg Leu Met Ala Glu Val Ile Gly Gly Arg
                165                 170                 175

Ala Gly Leu Lys Ala Ala Gly Gly Val Arg Thr Pro Ala Asp Ala Gln
            180                 185                 190

Ala Met Ile Glu Ala Gly Ala Thr Arg Leu Gly Thr Ser Gly Gly Val
        195                 200                 205

Gly Leu Val Ser Gly Gly Glu Asn Gly Ala Gly Tyr
    210                 215                 220

<210> SEQ ID NO 52
<211> LENGTH: 229
<212> TYPE: PRT
<213> ORGANISM: Lactobacillus brevis
<300> PUBLICATION INFORMATION:
<308> DATABASE ACCESSION NUMBER: WP_011668298.1
<309> DATABASE ENTRY DATE: 2019-06-20
<313> RELEVANT RESIDUES IN SEQ ID NO: (1)..(229)

<400> SEQUENCE: 52

Met Thr Leu Thr Thr Glu Gln Leu Ala Lys Tyr Ile Asp His Thr Asn
1               5                   10                  15

```
Leu Lys Ala Asp Ala Thr Glu Ala Asp Ile Lys Gln Thr Cys Asp Glu
            20                  25                  30

Ala Lys Lys Phe Asn Thr Ala Ser Val Cys Val Asn Ser Tyr Trp Ile
        35                  40                  45

Pro Phe Val Thr Glu Gln Leu Lys Gly Thr Asp Val Asn Pro Ile Ala
 50                  55                  60

Val Val Gly Phe Pro Leu Gly Ala Met Ala Thr Glu Ser Glu Ile Phe
 65                  70                  75                  80

Glu Ala Thr Thr Ala Ile Asp Gln Gly Ala Glu Ile Asp Met Val
                85                  90                  95

Leu Asn Val Gly Glu Leu Lys Gly Gly Asn Asp Glu Lys Val Leu Ala
                100                 105                 110

Asp Ile Gln Gly Leu Ala Asp Ala Val His Ala Lys Gly Lys Ile Leu
            115                 120                 125

Lys Val Ile Leu Glu Asn Ala Leu Leu Thr Lys Asp Glu Ile Val Arg
 130                 135                 140

Ala Cys Gln Leu Ser Glu Lys Ala Gly Ala Asp Phe Val Lys Thr Ser
 145                 150                 155                 160

Thr Gly Phe Ser Thr Ser Gly Ala Lys Val Glu Asp Val Lys Leu Met
                165                 170                 175

Arg Glu Thr Val Gly Asp Arg Leu Gly Val Lys Ala Ser Gly Gly Ile
                180                 185                 190

His Ser Arg Glu Glu Ala Leu Ala Met Ile Asp Ala Gly Ala Ser Arg
            195                 200                 205

Met Gly Val Ser Ala Thr Val Ala Ile Leu Thr Gly Asp Asp Ser His
 210                 215                 220

Ala Lys Ala Gly Tyr
 225

<210> SEQ ID NO 53
<211> LENGTH: 248
<212> TYPE: PRT
<213> ORGANISM: Thermotoga maritima
<300> PUBLICATION INFORMATION:
<308> DATABASE ACCESSION NUMBER: AAD36625.1
<309> DATABASE ENTRY DATE: 2014-01-31
<313> RELEVANT RESIDUES IN SEQ ID NO: (1)..(248)

<400> SEQUENCE: 53

Met Ile Glu Tyr Arg Ile Glu Glu Ala Val Ala Lys Tyr Arg Glu Phe
 1               5                   10                  15

Tyr Glu Phe Lys Pro Val Arg Glu Ser Ala Gly Ile Glu Asp Val Lys
            20                  25                  30

Ser Ala Ile Glu His Thr Asn Leu Lys Pro Phe Ala Thr Pro Asp Asp
        35                  40                  45

Ile Lys Lys Leu Cys Leu Glu Ala Arg Glu Asn Arg Phe His Gly Val
 50                  55                  60

Cys Val Asn Pro Cys Tyr Val Lys Leu Ala Arg Glu Glu Leu Glu Gly
 65                  70                  75                  80

Thr Asp Val Lys Val Val Thr Val Val Gly Phe Pro Leu Gly Ala Asn
                85                  90                  95

Glu Thr Arg Thr Lys Ala His Glu Ala Ile Phe Ala Val Glu Ser Gly
            100                 105                 110

Ala Asp Glu Ile Asp Met Val Ile Asn Val Gly Met Leu Lys Ala Lys
            115                 120                 125
```

```
Glu Trp Glu Tyr Val Tyr Glu Asp Ile Arg Ser Val Val Glu Ser Val
130                 135                 140
Lys Gly Lys Val Val Lys Val Ile Ile Glu Thr Cys Tyr Leu Asp Thr
145                 150                 155                 160
Glu Glu Lys Ile Ala Ala Cys Val Ile Ser Lys Leu Ala Gly Ala His
                165                 170                 175
Phe Val Lys Thr Ser Thr Gly Phe Gly Thr Gly Ala Thr Ala Glu
                180                 185                 190
Asp Val His Leu Met Lys Trp Ile Val Gly Asp Glu Met Gly Val Lys
                195                 200                 205
Ala Ser Gly Gly Ile Arg Thr Phe Glu Asp Ala Val Lys Met Ile Met
210                 215                 220
Tyr Gly Ala Asp Arg Ile Gly Thr Ser Ser Gly Val Lys Ile Val Gln
225                 230                 235                 240
Gly Gly Glu Glu Arg Tyr Gly Gly
                245

<210> SEQ ID NO 54
<211> LENGTH: 224
<212> TYPE: PRT
<213> ORGANISM: Methanobacterium thermoautotrophicum
<300> PUBLICATION INFORMATION:
<308> DATABASE ACCESSION NUMBER: AAB85318.1
<309> DATABASE ENTRY DATE: 2014-01-30
<313> RELEVANT RESIDUES IN SEQ ID NO: (1)..(224)

<400> SEQUENCE: 54

Met Val Lys Met Asn Val Glu Thr Arg Glu Glu Leu Ala Ser Leu Ile
1               5                   10                  15
Asp His Thr Asn Val Arg Ala Asp Ala Thr Glu Asn Asp Ile Glu Arg
                20                  25                  30
Leu Cys Arg Glu Ala Val Ser Tyr Gly Phe Arg Cys Ala Val Val Thr
            35                  40                  45
Pro Thr Asn Val Arg Leu Ala Ala Glu Leu Leu Glu Gly Thr Asp Val
        50                  55                  60
Thr Val Cys Ser Val Val Gly Phe Pro Ala Gly Val Ser Thr Pro Arg
65                  70                  75                  80
Val Lys Ala Leu Glu Ala Ser Glu Ala Val Glu Asn Gly Ala Gly Glu
                85                  90                  95
Val Asp Met Val Met Asn Ile Gly Ala Met Lys Ser Gly Asn Arg Glu
                100                 105                 110
Leu Val Tyr Arg Asp Ile Ser Gly Val Val Asp Ala Ala Gly Val Pro
            115                 120                 125
Val Lys Val Ile Leu Glu Thr Ala Tyr Leu Thr Asp Lys Glu Lys Val
130                 135                 140
Glu Ala Cys Leu Ile Ser Lys Glu Ala Gly Ala Ala Phe Val Lys Thr
145                 150                 155                 160
Ser Thr Ala Tyr Gly Gly Leu Ala Gly Ala Thr Val Glu Asp Val Met
                165                 170                 175
Leu Met Arg Lys Thr Val Gly Asp Glu Met Gly Val Lys Ala Ser Gly
                180                 185                 190
Gly Ile Arg Asp Leu Glu Thr Ala Leu Ala Met Ile Asp Ala Gly Ala
                195                 200                 205
Asp Arg Ile Gly Thr Ser Thr Gly Val Gln Ile Ile Glu Gly Trp Arg
210                 215                 220
```

<210> SEQ ID NO 55
<211> LENGTH: 212
<212> TYPE: PRT
<213> ORGANISM: Halobacterium sp.
<300> PUBLICATION INFORMATION:
<308> DATABASE ACCESSION NUMBER: NP_280582.1
<309> DATABASE ENTRY DATE: 2014-12-16
<313> RELEVANT RESIDUES IN SEQ ID NO: (1)..(212)

<400> SEQUENCE: 55

Met Asp Arg Glu Thr Leu Ala Ala Arg Ile Asp His Thr Val Leu Gly
1               5                   10                  15

Pro Thr Thr Thr Arg Ala Asp Val Leu Ser Val Val Asp Asp Ala Glu
            20                  25                  30

Ala His Gly Met Asn Val Cys Ile Pro Pro Cys Tyr Val Ala Asp Ala
        35                  40                  45

Arg Asp His Ala Ser Ala Asp Arg Thr Ile Ala Thr Val Ile Gly Phe
    50                  55                  60

Pro His Gly Thr Gln Ala Thr Ser Val Lys Val Ala Ala Glu His
65                  70                  75                  80

Ala His Ala Asp Gly Ala Asp Glu Leu Asp Leu Val Ile Pro Ile Gly
                85                  90                  95

Arg Leu Lys Gly Gly Asp His Glu Ala Val Thr Ala Glu Ile Ala Ala
            100                 105                 110

Val Asn Asp Ala Thr Pro Leu Pro Val Lys Val Ile Ile Glu Thr Pro
        115                 120                 125

Val Leu Thr Asp Ala Glu Lys His Ala Ala Cys Glu Ala Ala Ala Asp
    130                 135                 140

Ala Asp Ala Ala Met Val Lys Thr Ala Thr Gly Phe Thr Asp Gly Gly
145                 150                 155                 160

Ala Thr Val Pro Asp Val Ser Leu Met Ser Glu Tyr Leu Pro Val Lys
                165                 170                 175

Ala Ser Gly Gly Val Gly Thr Tyr Ala Asp Ala Ala Met Phe Asp
            180                 185                 190

Ala Gly Ala Val Arg Ile Gly Ala Ser Ser Gly Val Asp Ile Val Ala
        195                 200                 205

Ser Phe Ala Glu
    210

<210> SEQ ID NO 56
<211> LENGTH: 246
<212> TYPE: PRT
<213> ORGANISM: Thermoplasma acidophilum
<300> PUBLICATION INFORMATION:
<308> DATABASE ACCESSION NUMBER: CAC11822.1
<309> DATABASE ENTRY DATE: 2015-02-27
<313> RELEVANT RESIDUES IN SEQ ID NO: (1)..(246)

<400> SEQUENCE: 56

Met Lys Tyr Ser Ile Glu Gln Val Met Arg Leu Val Asp His Ser Gly
1               5                   10                  15

Leu Lys Pro Tyr Leu Thr Glu Lys Asp Ile Ala Arg Leu Ile Glu Glu
            20                  25                  30

Ala Lys Asp Met Gly Asn Tyr Ala Val Cys Ile Glu Pro Ile Tyr Gly
        35                  40                  45

Lys Phe Ala Lys Glu Tyr Leu Asp Glu Lys Arg Tyr Lys Val Lys Leu
    50                  55                  60

Asp Val Thr Ile Asp Phe Pro Phe Gly Ser Leu Ala Thr Ser Ser Arg
65                  70                  75                  80

```
Lys Lys Ile Ile Glu Asp Ser Asp Tyr Ala Asp Glu Val Asp Ile Val
                85                  90                  95

Val Pro Met Gly Tyr Val Lys Ser His Arg Trp Asp Tyr Val Asp Gln
            100                 105                 110

Asp Leu Thr Asp Val Val Lys Ile Ala Lys Asp His Asp Leu Val Ile
            115                 120                 125

Lys Ile Ile Thr Glu Asp Gly Tyr Leu Thr Gln Asp Glu Lys Asp Arg
        130                 135                 140

Leu Tyr Arg Ser Val Ile Arg Ala Lys Pro Asp Phe Ile Lys Thr Ser
145                 150                 155                 160

Thr Gly Phe Ala Asn Lys Asp Tyr Cys Ala Ser Leu Gly Asn Ala Ala
                165                 170                 175

Gly Ala Thr Pro Asp Asn Val Ser Leu Met Ser Arg Ile Ala Glu Glu
            180                 185                 190

Leu Gly Ser Asp Ile Gly Ile Lys Ala Ala Gly Gly Ile His Thr Tyr
            195                 200                 205

Arg Glu Ile Glu Ser Ile Ile Asp Ala Ala Lys Arg Pro Ile Asp Pro
        210                 215                 220

Glu Lys Leu Arg Ile Gly Met Ser Gly Thr Gly Lys Val Phe Glu Glu
225                 230                 235                 240

Met Lys Lys Ile Lys Lys
                245

<210> SEQ ID NO 57
<211> LENGTH: 259
<212> TYPE: PRT
<213> ORGANISM: Escherichia coli K12
<300> PUBLICATION INFORMATION:
<308> DATABASE ACCESSION NUMBER: NP_418798.1
<309> DATABASE ENTRY DATE: 2018-10-11
<313> RELEVANT RESIDUES IN SEQ ID NO: (1)..(259)

<400> SEQUENCE: 57

Met Thr Asp Leu Lys Ala Ser Ser Leu Arg Ala Leu Lys Leu Met Asp
1               5                   10                  15

Leu Thr Thr Leu Asn Asp Asp Thr Asp Lys Val Ile Ala Leu
            20                  25                  30

Cys His Gln Ala Lys Thr Pro Val Gly Asn Thr Ala Ala Ile Cys Ile
            35                  40                  45

Tyr Pro Arg Phe Ile Pro Ile Ala Arg Lys Thr Leu Lys Glu Gln Gly
        50                  55                  60

Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr
                85                  90                  95

Gly Ala Asp Glu Val Asp Val Val Phe Pro Tyr Arg Ala Leu Met Ala
            100                 105                 110

Gly Asn Glu Gln Val Gly Phe Asp Leu Val Lys Ala Cys Lys Glu Ala
            115                 120                 125

Cys Ala Ala Ala Asn Val Leu Leu Lys Val Ile Ile Glu Thr Gly Glu
            130                 135                 140

Leu Lys Asp Glu Ala Leu Ile Arg Lys Ala Ser Glu Ile Ser Ile Lys
145                 150                 155                 160

Ala Gly Ala Asp Phe Ile Lys Thr Ser Thr Gly Lys Val Ala Val Asn
                165                 170                 175
```

```
Ala Thr Pro Glu Ser Ala Arg Ile Met Met Glu Val Ile Arg Asp Met
            180                 185                 190

Gly Val Glu Lys Thr Val Gly Phe Lys Pro Ala Gly Val Arg Thr
        195                 200                 205

Ala Glu Asp Ala Gln Lys Tyr Leu Ala Ile Ala Asp Glu Leu Phe Gly
    210                 215                 220

Ala Asp Trp Ala Asp Ala Arg His Tyr Arg Phe Gly Ala Ser Ser Leu
225                 230                 235                 240

Leu Ala Ser Leu Leu Lys Ala Leu Gly His Gly Asp Gly Lys Ser Ala
            245                 250                 255

Ser Ser Tyr

<210> SEQ ID NO 58
<211> LENGTH: 331
<212> TYPE: PRT
<213> ORGANISM: Bacillus subtilis
<300> PUBLICATION INFORMATION:
<308> DATABASE ACCESSION NUMBER: CAB12792.1
<309> DATABASE ENTRY DATE: 2018-02-08
<313> RELEVANT RESIDUES IN SEQ ID NO: (1)..(331)

<400> SEQUENCE: 58

Met Glu Tyr Thr Ser Ile Ala Asp Thr Gly Ile Glu Ala Ser Arg Ile
1               5                   10                  15

Gly Leu Gly Thr Trp Ala Ile Gly Gly Thr Met Trp Gly Gly Thr Asp
            20                  25                  30

Glu Lys Thr Ser Ile Glu Thr Ile Arg Ala Ala Leu Asp Gln Gly Ile
        35                  40                  45

Thr Leu Ile Asp Thr Ala Pro Ala Tyr Gly Phe Gly Gln Ser Glu Glu
    50                  55                  60

Ile Val Gly Lys Ala Ile Lys Glu Tyr Gly Lys Arg Asp Gln Val Ile
65                  70                  75                  80

Leu Ala Thr Lys Thr Ala Leu Asp Trp Lys Asn Asn Gln Leu Phe Arg
                85                  90                  95

His Ala Asn Arg Ala Arg Ile Val Glu Glu Val Glu Asn Ser Leu Lys
            100                 105                 110

Arg Leu Gln Thr Asp Tyr Ile Asp Leu Tyr Gln Val His Trp Pro Asp
        115                 120                 125

Pro Leu Val Pro Ile Glu Glu Thr Ala Glu Val Met Lys Glu Leu Tyr
    130                 135                 140

Asp Ala Gly Lys Ile Arg Ala Ile Gly Val Ser Asn Phe Ser Ile Glu
145                 150                 155                 160

Gln Met Asp Thr Phe Arg Ala Val Ala Pro Leu His Thr Ile Gln Pro
                165                 170                 175

Pro Tyr Asn Leu Phe Glu Arg Glu Met Glu Ser Val Leu Pro Tyr
            180                 185                 190

Ala Lys Asp Asn Lys Ile Thr Thr Leu Leu Tyr Gly Ser Leu Cys Arg
        195                 200                 205

Gly Leu Leu Thr Gly Lys Met Thr Glu Glu Tyr Thr Phe Glu Gly Asp
    210                 215                 220

Asp Leu Arg Asn His Asp Pro Lys Phe Gln Lys Pro Arg Phe Lys Glu
225                 230                 235                 240

Tyr Leu Ser Ala Val Asn Gln Leu Asp Lys Leu Ala Lys Thr Arg Tyr
                245                 250                 255

Gly Lys Ser Val Ile His Leu Ala Val Arg Trp Ile Leu Asp Gln Pro
            260                 265                 270
```

-continued

Gly Ala Asp Ile Ala Leu Trp Gly Ala Arg Lys Pro Gly Gln Leu Glu
                275                 280                 285

Ala Leu Ser Glu Ile Thr Gly Trp Thr Leu Asn Ser Glu Asp Gln Lys
        290                 295                 300

Asp Ile Asn Thr Ile Leu Glu Asn Thr Ile Ser Asp Pro Val Gly Pro
305                 310                 315                 320

Glu Phe Met Ala Pro Pro Thr Arg Glu Glu Ile
                325                 330

<210> SEQ ID NO 59
<211> LENGTH: 329
<212> TYPE: PRT
<213> ORGANISM: Pseudomonas aeruginosa
<300> PUBLICATION INFORMATION:
<308> DATABASE ACCESSION NUMBER: NP_249818.1
<309> DATABASE ENTRY DATE: 2019-01-24
<313> RELEVANT RESIDUES IN SEQ ID NO: (1)..(329)

<400> SEQUENCE: 59

Met Ser Val Glu Ser Ile Arg Ile Glu Gly Ile Asp Thr Pro Val Ser
1               5                   10                  15

Arg Ile Gly Leu Gly Thr Trp Ala Ile Gly Gly Trp Met Trp Gly Gly
            20                  25                  30

Ala Asp Asp Ala Thr Ser Val Glu Thr Ile Arg Arg Ala Val Glu Ser
        35                  40                  45

Gly Ile Asn Leu Ile Asp Thr Ala Pro Val Tyr Gly Phe Gly His Ser
    50                  55                  60

Glu Glu Val Val Gly Lys Ala Leu Gln Gly Leu Arg Asp Lys Ala Val
65                  70                  75                  80

Ile Ala Thr Lys Ala Ala Leu Glu Trp Ser Asp Ala Gly Ile His Arg
                85                  90                  95

Asn Ala Ser Ala Ala Arg Ile Arg Arg Glu Val Glu Asp Ser Leu Arg
            100                 105                 110

Arg Leu Lys Thr Asp Arg Ile Asp Leu Tyr Gln Ile His Trp Pro Asp
        115                 120                 125

Pro Leu Val Ala His Glu Glu Thr Ala Gly Glu Leu Glu Arg Leu Arg
    130                 135                 140

Arg Asp Gly Lys Ile Leu Ala Ile Gly Val Ser Asn Tyr Ser Pro Glu
145                 150                 155                 160

Gln Met Asp Gly Phe Arg Gln Phe Ala Pro Leu Ala Ser Val Gln Pro
                165                 170                 175

Pro Tyr Asn Leu Phe Glu Arg Ala Ile Asp Ala Asp Val Leu Pro Tyr
            180                 185                 190

Ala Glu Arg Asn Gly Ile Val Val Leu Ala Tyr Gly Ala Leu Cys Arg
        195                 200                 205

Gly Leu Leu Ser Gly Arg Met Asn Ala Glu Thr Arg Phe Asp Gly Asp
    210                 215                 220

Asp Leu Arg Lys Ser Asp Pro Lys Phe Gln Gln Pro Arg Phe Ala Gln
225                 230                 235                 240

Tyr Leu Ala Ala Val Ala Gln Leu Glu Glu Leu Ala Arg Glu Arg Tyr
                245                 250                 255

Gly Lys Ser Val Leu Ala Leu Ala Ile Arg Trp Ile Leu Asp Arg Gly
            260                 265                 270

Pro Thr Val Ala Leu Trp Gly Ala Arg Lys Pro Glu Gln Leu Asn Gly
        275                 280                 285

```
Ile Ala Asp Ala Phe Gly Trp Arg Leu Asp Asp Glu Ala Met Ala Arg
    290                 295                 300

Ile Glu Arg Ile Leu Ala Glu Thr Ile Gln Asp Pro Val Gly Pro Glu
305             310                 315                 320

Phe Met Ala Pro Pro Ser Arg Asn Ala
                    325
```